(12) United States Patent
Fischer et al.

(10) Patent No.: US 12,280,091 B2
(45) Date of Patent: Apr. 22, 2025

(54) ETCH SELECTIVITY CONTROL IN ATOMIC LAYER ETCHING

(71) Applicant: Lam Research Corporation, Fremont, CA (US)

(72) Inventors: Andreas Fischer, Castro Valley, CA (US); Thorsten Bernd Lill, Kalaheo, HI (US)

(73) Assignee: Lam Research Corporation, Fremont, CA (US)

( * ) Notice: Subject to any disclaimer, the term of this patent is extended or adjusted under 35 U.S.C. 154(b) by 0 days.

(21) Appl. No.: 18/003,246

(22) PCT Filed: Dec. 10, 2021

(86) PCT No.: PCT/US2021/062793
§ 371 (c)(1),
(2) Date: Dec. 23, 2022

(87) PCT Pub. No.: WO2022/169509
PCT Pub. Date: Aug. 11, 2022

(65) Prior Publication Data
US 2023/0326761 A1    Oct. 12, 2023

Related U.S. Application Data

(60) Provisional application No. 63/199,932, filed on Feb. 3, 2021.

(51) Int. Cl.
*H01L 21/67*    (2006.01)
*A61K 38/17*    (2006.01)
(Continued)

(52) U.S. Cl.
CPC .......... *A61K 38/1716* (2013.01); *C09K 13/08* (2013.01); *H01J 37/32449* (2013.01);
(Continued)

(58) Field of Classification Search
None
See application file for complete search history.

(56) References Cited

U.S. PATENT DOCUMENTS

| 4,313,782 A | 2/1982 | Sokoloski |
| 4,414,069 A | 11/1983 | Cuomo |

(Continued)

FOREIGN PATENT DOCUMENTS

| CN | 101631894 A | 1/2010 |
| CN | 102934208 A | 2/2013 |

(Continued)

OTHER PUBLICATIONS

Athavale et al. (1995) "Molecular dynamics simulation of atomic layer etching of silicon," J. Vac. Sci. Technol. A, 13(3):966-971.
(Continued)

*Primary Examiner* — Shamim Ahmed
(74) *Attorney, Agent, or Firm* — Weaver Austin Villeneuve & Sampson LLP

(57) ABSTRACT

Apparatuses and methods are provided. Some methods may include providing a substrate to a processing chamber, the substrate having a first material adjacent to and covering a surface of a second material, modifying a layer of the first material by flowing a first process gas onto the substrate and thereby creating a modified layer of the first material, removing the modified layer of the first material by flowing a second process gas onto the substrate, and converting, when the surface of the second material is uncovered via removal of the modified layer, the surface to a converted layer of the second material by flowing a third process gas onto the substrate, in which the first and second process gases are less reactive with the converted layer than with the first material and the second material.

30 Claims, 18 Drawing Sheets

(51) Int. Cl.
  *C09K 13/08* (2006.01)
  *H01J 37/32* (2006.01)
  *H01L 21/311* (2006.01)

(52) U.S. Cl.
  CPC .. *H01L 21/31122* (2013.01); *H01L 21/67069* (2013.01); *H01J 37/32091* (2013.01); *H01J 2237/334* (2013.01)

(56) References Cited

U.S. PATENT DOCUMENTS

| | | |
|---|---|---|
| 4,695,327 A | 9/1987 | Grebinski |
| 4,756,794 A | 7/1988 | Yoder |
| 5,030,319 A | 7/1991 | Nishino et al. |
| 5,078,832 A | 1/1992 | Tanaka |
| 5,234,540 A | 8/1993 | Grant et al. |
| 5,268,069 A | 12/1993 | Chapple-Sokol et al. |
| 5,271,800 A | 12/1993 | Koontz et al. |
| 5,282,925 A | 2/1994 | Jeng et al. |
| 5,431,772 A | 7/1995 | Babie et al. |
| 5,439,553 A | 8/1995 | Grant et al. |
| 5,474,641 A | 12/1995 | Otsuki et al. |
| 5,482,802 A | 1/1996 | Celler et al. |
| 5,505,816 A | 4/1996 | Barnes et al. |
| 5,527,425 A | 6/1996 | Hobson et al. |
| 5,620,559 A | 4/1997 | Kikuchi |
| 5,635,102 A | 6/1997 | Mehta |
| 5,636,320 A | 6/1997 | Yu et al. |
| 5,766,971 A | 6/1998 | Ahlgren et al. |
| 5,789,265 A | 8/1998 | Nitta et al. |
| 5,792,275 A | 8/1998 | Natzle et al. |
| 5,814,239 A | 9/1998 | Kaneko et al. |
| 5,838,055 A | 11/1998 | Kleinhenz et al. |
| 5,858,830 A | 1/1999 | Yoo et al. |
| 5,876,879 A | 3/1999 | Kleinhenz et al. |
| 5,880,032 A | 3/1999 | Doi et al. |
| 5,913,140 A | 6/1999 | Roche et al. |
| 5,922,624 A | 7/1999 | Verhaverbeke et al. |
| 5,968,279 A | 10/1999 | Macleish et al. |
| 5,976,973 A | 11/1999 | Ohira et al. |
| 5,990,019 A | 11/1999 | Torek et al. |
| 5,994,240 A | 11/1999 | Thakur |
| 6,030,881 A | 2/2000 | Papasouliotis et al. |
| 6,069,092 A | 5/2000 | Imai et al. |
| 6,071,815 A | 6/2000 | Kleinhenz et al. |
| 6,074,951 A | 6/2000 | Kleinhenz et al. |
| 6,146,970 A | 11/2000 | Witek et al. |
| 6,204,198 B1 | 3/2001 | Banerjee et al. |
| 6,265,302 B1 | 7/2001 | Lim et al. |
| 6,335,261 B1 | 1/2002 | Natzle et al. |
| 6,483,154 B1 | 11/2002 | Ngo et al. |
| 6,573,181 B1 | 6/2003 | Srinivas et al. |
| 6,635,965 B1 | 10/2003 | Lee et al. |
| 6,652,713 B2 | 11/2003 | Brown et al. |
| 6,693,050 B1 | 2/2004 | Cui et al. |
| 6,706,334 B1 | 3/2004 | Kobayashi et al. |
| 6,716,691 B1 | 4/2004 | Evans et al. |
| 6,726,805 B2 | 4/2004 | Brown et al. |
| 6,740,247 B1 | 5/2004 | Han et al. |
| 6,774,000 B2 | 8/2004 | Natzle et al. |
| 6,776,874 B2 | 8/2004 | Kobayashi et al. |
| 6,790,733 B1 | 9/2004 | Natzle et al. |
| 6,803,309 B2 | 10/2004 | Chou et al. |
| 6,817,776 B2 | 11/2004 | Colgan et al. |
| 6,837,968 B2 | 1/2005 | Brown et al. |
| 6,844,258 B1 | 1/2005 | Fair et al. |
| 6,852,584 B1 | 2/2005 | Chen et al. |
| 6,858,532 B2 | 2/2005 | Natzle et al. |
| 6,905,965 B2 | 6/2005 | Subrahmanyan et al. |
| 6,926,843 B2 | 8/2005 | Cantell et al. |
| 6,933,242 B1 | 8/2005 | Srinivasan et al. |
| 6,949,481 B1 | 9/2005 | Halliyal et al. |
| 6,951,821 B2 | 10/2005 | Hamelin et al. |
| 6,967,167 B2 | 11/2005 | Geiss et al. |
| 6,992,011 B2 | 1/2006 | Nemoto et al. |
| 7,005,372 B2 | 2/2006 | Levy et al. |
| 7,029,536 B2 | 4/2006 | Hamelin et al. |
| 7,033,909 B2 | 4/2006 | Kim et al. |
| 7,052,941 B2 | 5/2006 | Lee |
| 7,079,760 B2 | 7/2006 | Hamelin et al. |
| 7,141,494 B2 | 11/2006 | Lee et al. |
| 7,163,899 B1 | 1/2007 | Cho et al. |
| 7,416,989 B1 | 8/2008 | Liu et al. |
| 7,435,661 B2 | 10/2008 | Miller et al. |
| 7,589,017 B2 | 9/2009 | Chan et al. |
| 7,651,922 B2 | 1/2010 | Matsuda |
| 7,772,114 B2 | 8/2010 | Chan et al. |
| 7,955,972 B2 | 6/2011 | Chan et al. |
| 7,977,249 B1 | 7/2011 | Liu et al. |
| 7,981,763 B1 | 7/2011 | Van Schravendijk et al. |
| 8,043,972 B1 | 10/2011 | Liu et al. |
| 8,048,805 B2 | 11/2011 | Chan et al. |
| 8,058,170 B2 | 11/2011 | Chandrashekar et al. |
| 8,058,179 B1 | 11/2011 | Draeger et al. |
| 8,124,505 B1 | 2/2012 | Burnham et al. |
| 8,124,531 B2 | 2/2012 | Chandrashekar et al. |
| 8,187,486 B1 | 5/2012 | Liu et al. |
| 8,551,885 B2 | 10/2013 | Chen et al. |
| 8,617,348 B1 | 12/2013 | Liu et al. |
| 8,808,561 B2 | 8/2014 | Kanarik |
| 8,883,028 B2 | 11/2014 | Kanarik |
| 8,993,352 B2 | 3/2015 | Nishimura et al. |
| 9,230,818 B2 | 1/2016 | Moustakas et al. |
| 9,362,163 B2 | 6/2016 | Danek et al. |
| 9,378,970 B2 | 6/2016 | Joubert et al. |
| 9,425,041 B2 | 8/2016 | Berry, III et al. |
| 9,431,268 B2 | 8/2016 | Lill et al. |
| 9,443,701 B2 | 9/2016 | Watanabe |
| 9,570,317 B2 | 2/2017 | Posseme et al. |
| 9,570,600 B2 | 2/2017 | Lu et al. |
| 9,576,811 B2 | 2/2017 | Kanarik et al. |
| 9,647,206 B2 | 5/2017 | Hashimoto et al. |
| 9,773,683 B2 | 9/2017 | Gupta et al. |
| 9,806,252 B2 | 10/2017 | Tan et al. |
| 9,991,128 B2 | 6/2018 | Tan et al. |
| 10,056,264 B2 | 8/2018 | Yang et al. |
| 10,096,487 B2 | 10/2018 | Yang et al. |
| 10,381,227 B2 | 8/2019 | George et al. |
| 10,566,212 B2 | 2/2020 | Kanarik |
| 10,566,213 B2 | 2/2020 | Kanarik et al. |
| 10,679,868 B2 | 6/2020 | Berry, III et al. |
| 11,239,094 B2 | 2/2022 | Kanarik |
| 11,380,556 B2 | 7/2022 | Panagopoulos et al. |
| 11,935,758 B2 * | 3/2024 | Yang ................ H01L 21/32139 |
| 2001/0016226 A1 | 8/2001 | Natzle et al. |
| 2002/0106908 A1 | 8/2002 | Cohen et al. |
| 2003/0015704 A1 | 1/2003 | Curless |
| 2003/0029568 A1 | 2/2003 | Brown et al. |
| 2003/0134038 A1 | 7/2003 | Paranjpe |
| 2004/0018740 A1 | 1/2004 | Brown et al. |
| 2004/0083977 A1 | 5/2004 | Brown et al. |
| 2004/0110354 A1 | 6/2004 | Natzle et al. |
| 2004/0182324 A1 | 9/2004 | Wallace et al. |
| 2004/0184792 A1 | 9/2004 | Hamelin et al. |
| 2004/0185670 A1 | 9/2004 | Hamelin et al. |
| 2004/0200244 A1 | 10/2004 | Hong et al. |
| 2004/0212035 A1 | 10/2004 | Yeo et al. |
| 2004/0226814 A1 | 11/2004 | Stewart et al. |
| 2005/0056370 A1 | 3/2005 | Brown et al. |
| 2005/0101130 A1 | 5/2005 | Lopatin et al. |
| 2005/0106877 A1 | 5/2005 | Elers et al. |
| 2005/0116300 A1 | 6/2005 | Hieda et al. |
| 2005/0153519 A1 | 7/2005 | Lu et al. |
| 2005/0205110 A1 | 9/2005 | Kao et al. |
| 2005/0218113 A1 | 10/2005 | Yue |
| 2005/0218507 A1 | 10/2005 | Kao et al. |
| 2005/0221552 A1 | 10/2005 | Kao et al. |
| 2005/0230350 A1 | 10/2005 | Kao et al. |
| 2005/0241933 A1 | 11/2005 | Branton et al. |
| 2005/0266684 A1 | 12/2005 | Lee et al. |
| 2005/0270895 A1 | 12/2005 | Strang |
| 2006/0003596 A1 | 1/2006 | Fucsko et al. |
| 2006/0051959 A1 | 3/2006 | Iwatake et al. |
| 2006/0051966 A1 | 3/2006 | Or et al. |

(56) References Cited

U.S. PATENT DOCUMENTS

| | | |
|---|---|---|
| 2006/0115937 A1 | 6/2006 | Barnett et al. |
| 2006/0207968 A1 | 9/2006 | Mumbauer et al. |
| 2006/0270239 A1 | 11/2006 | Triyoso et al. |
| 2007/0063277 A1 | 3/2007 | Belyansky et al. |
| 2007/0082508 A1 | 4/2007 | Chiang et al. |
| 2007/0215975 A1 | 9/2007 | Idani et al. |
| 2008/0038894 A1 | 2/2008 | Rueger et al. |
| 2008/0233709 A1 | 9/2008 | Conti et al. |
| 2009/0181553 A1 | 7/2009 | Koelmel et al. |
| 2009/0236693 A1 | 9/2009 | Moustakas et al. |
| 2009/0289263 A1 | 11/2009 | Duong et al. |
| 2009/0308840 A1 | 12/2009 | Kohno et al. |
| 2010/0062602 A1 | 3/2010 | Sakamoto et al. |
| 2010/0291751 A1 | 11/2010 | Lee et al. |
| 2011/0056625 A1 | 3/2011 | Rueger et al. |
| 2011/0139748 A1 | 6/2011 | Donnelly et al. |
| 2011/0151635 A1 | 6/2011 | Liu et al. |
| 2011/0192820 A1 | 8/2011 | Yeom et al. |
| 2011/0244688 A1 | 10/2011 | Ohsawa et al. |
| 2012/0009785 A1 | 1/2012 | Chandrashekar et al. |
| 2013/0099277 A1 | 4/2013 | Speck et al. |
| 2013/0168354 A1 | 7/2013 | Kanarik |
| 2013/0200391 A1 | 8/2013 | Bedair et al. |
| 2013/0313561 A1 | 11/2013 | Suh |
| 2014/0061861 A1 | 3/2014 | Moustakas et al. |
| 2014/0335666 A1 | 11/2014 | Koehler et al. |
| 2015/0037972 A1 | 2/2015 | Danek et al. |
| 2015/0118848 A1 | 4/2015 | Draeger et al. |
| 2015/0132961 A1 | 5/2015 | Chang et al. |
| 2015/0162168 A1 | 6/2015 | Oehrlein et al. |
| 2015/0228495 A1 | 8/2015 | Joubert et al. |
| 2015/0270140 A1 | 9/2015 | Gupta et al. |
| 2016/0013063 A1 | 1/2016 | Ranjan et al. |
| 2016/0064244 A1 | 3/2016 | Agarwal et al. |
| 2016/0196969 A1 | 7/2016 | Berry, III et al. |
| 2016/0196984 A1 | 7/2016 | Lill et al. |
| 2016/0203995 A1 | 7/2016 | Kanarik et al. |
| 2016/0293437 A1 | 10/2016 | Zhou et al. |
| 2016/0308112 A1 | 10/2016 | Tan et al. |
| 2016/0329221 A1 | 11/2016 | Berry, III et al. |
| 2016/0358782 A1 | 12/2016 | Yang et al. |
| 2016/0379824 A1 | 12/2016 | Wise et al. |
| 2017/0053810 A1 | 2/2017 | Yang et al. |
| 2017/0069462 A1 | 3/2017 | Kanarik et al. |
| 2017/0221781 A1 | 8/2017 | Theisen et al. |
| 2017/0229311 A1 | 8/2017 | Tan et al. |
| 2017/0229314 A1 | 8/2017 | Tan et al. |
| 2017/0243755 A1 | 8/2017 | Tapily |
| 2017/0256416 A1 | 9/2017 | Fischer et al. |
| 2017/0345665 A1 | 11/2017 | Faguet et al. |
| 2017/0365478 A1 | 12/2017 | George et al. |
| 2018/0174860 A1 | 6/2018 | Kanarik |
| 2018/0350624 A1 | 12/2018 | Kanarik et al. |
| 2019/0108982 A1 | 4/2019 | Yang et al. |
| 2019/0122902 A1 | 4/2019 | Ko et al. |
| 2019/0131120 A1 | 5/2019 | Yamaguchi |
| 2019/0131130 A1 | 5/2019 | Smith et al. |
| 2019/0198345 A1 | 6/2019 | Fischer et al. |
| 2020/0027740 A1 | 1/2020 | Vervuurt et al. |
| 2020/0035493 A1 | 1/2020 | Clark et al. |
| 2020/0118835 A1 | 4/2020 | Kanarik |
| 2021/0104414 A1* | 4/2021 | Panagopoulos ... H01L 21/67115 |
| 2021/0280433 A1 | 9/2021 | Berry, III et al. |
| 2022/0093413 A1 | 3/2022 | Kanarik |
| 2022/0293431 A1 | 9/2022 | Panagopoulos et al. |

FOREIGN PATENT DOCUMENTS

| | | |
|---|---|---|
| CN | 103117216 A | 5/2013 |
| CN | 103748658 A | 4/2014 |
| CN | 104040021 A | 9/2014 |
| EP | 0298879 A1 | 1/1989 |
| JP | 74041461 B | 11/1974 |
| JP | H03263827 A | 11/1991 |
| JP | H04223329 A | 8/1992 |
| JP | H0529266 A | 2/1993 |
| JP | H05190517 A | 7/1993 |
| JP | H06295889 A | 10/1994 |
| JP | H06326060 A | 11/1994 |
| JP | H0917774 A | 1/1997 |
| JP | H09102490 A | 4/1997 |
| JP | 2006261451 A | 9/2006 |
| JP | 2012529777 A | 11/2012 |
| JP | 2016028424 A | 2/2016 |
| JP | 2016208031 A | 12/2016 |
| KR | 20050110751 A | 11/2005 |
| KR | 20060000876 A | 1/2006 |
| KR | 100606532 B1 | 7/2006 |
| KR | 20070029851 A | 3/2007 |
| KR | 20070086312 A | 8/2007 |
| KR | 20090053823 A | 5/2009 |
| KR | 100905993 B1 | 7/2009 |
| KR | 100925210 B1 | 11/2009 |
| KR | 20110092485 A | 8/2011 |
| KR | 20120024544 A | 3/2012 |
| KR | 20130031922 A | 1/2013 |
| KR | 20160124689 A | 10/2016 |
| KR | 102303153 B1 | 9/2021 |
| TW | 201027595 A | 7/2010 |
| TW | 201140687 A | 11/2011 |
| TW | I430334 B | 3/2014 |
| TW | 201643958 A | 12/2016 |
| WO | WO-2004001809 A2 | 12/2003 |
| WO | WO-2011081921 A2 | 7/2011 |
| WO | WO-2017205658 A1 | 11/2017 |

OTHER PUBLICATIONS

Byun et al. (2001) "The Effects of Reactive Precleaning (RPC+) on the Formation of Titanium Silicide By PECVD TiCl4—Ti Deposition, and Its Thermal Stability," IEEE, pp. 222-224.

Carver, C.T. et al., "Atomic Layer Etching: An Industry Perspective," ECS Journal of Solid State Science and Technology, vol. 4, No. 6, Feb. 20, 2015, pp. N5005-N5009.

Chang et al. (1997) "Interface Characteristics of Selective Tungsten on Silicon Using a New Pretreatment Technology for ULSI Application," IEEE, pp. 738 743.

Chen et al., "Directional etch of magnetic and noble metals. II. Organic chemical vapor etch" Journal of Vacuum Science & Technology A: Vacuum, Surfaces, and Films, vol. 35, 05C305 (2017) pp. 1-8. doi:10.1116/1.4983830.

Chinese Decision of Final Rejection Action dated Feb. 11, 2019 issued in Application No. CN 201511027151.7.

Chinese Decision of Final Rejection dated Apr. 25, 2019 issued in Application No. CN 201511021815.9.

Chinese First Office Action dated Aug. 28, 2019 issued in Application No. CN 201710066218.0.

Chinese First Office Action dated Dec. 22, 2017 issued in Application No. CN 201511027151.7.

Chinese First Office Action dated Dec. 5, 2017 issued in Application No. CN 201511021815.9.

Chinese First Office Action dated Jan. 9, 2019 issued in Application No. CN 201610694927.9.

Chinese First Office Action dated Jul. 23, 2018 issued in Application No. CN 201610393976.9.

Chinese Fourth Office Action dated Sep. 27, 2019 issued in Application No. CN 201511021815.9.

Chinese Fourth Office Action dated Sep. 27, 2019 issued in Application No. CN 201511027151.7.

Chinese Fourth Office Action dated Sep. 8, 2020 issued in Application No. CN 201610694927.9.

Chinese Notice of Allowance, dated Nov. 26, 2019 issued in Application No. CN 201511021815.9.

Chinese Reexamination Decision dated Mar. 2, 2021 issued in Application No. CN 201610694927.9.

Chinese Second Office Action dated Apr. 28, 2019 issued in Application No. CN 201610393976.9.

Chinese Second Office Action dated Aug. 16, 2018 issued in Application No. CN 201511027151.7.

(56) References Cited

OTHER PUBLICATIONS

Chinese Second Office Action dated Jul. 31, 2018 issued in Application No. CN 201511021815.9.
Chinese Second Office Action dated Jun. 17, 2019 issued in Application No. CN 201610694927.9.
Chinese Third Office Action dated Dec. 20, 2019 issued in Application No. CN 201610694927.9.
Chinese Third Office Action dated Jan. 22, 2019 issued in Application No. CN 201511021815.9.
Chinese Third Office Action dated Sep. 3, 2019 issued in Application No. CN 201610393976.9.
Chinese Third Office Action [Reinstated] dated Jul. 15, 2019 issued in Application No. CN 201511027151.7.
CN Office Action dated Mar. 10, 2023, in Application No. CN201780086828.5.
DeSalvo, G. et al., (1996) "Controlled Digital Etching of GaAs for Precise Gate Recess Formation in MESFET, HEMT and pHEMT Device Fabrication," [http://csmantech.pairserver.com/newsite/gaasmantech/Digests/1996/papers/1996%202.2%20controlled%20digital%20etching%20gaas.pdf], pp. 29-31.
European Extended Search Report dated May 30, 2016 issued in Application No. EP 15200663.1.
Extended European Search Report dated Mar. 14, 2022, in Application No. 19833221.5.
George, et al., "Prospects for Thermal Atomic Layer Etching Using Sequential, Self-Limiting Fluorination and Ligand-Exchange Reactions" ACS Nano (2016) vol. 10, 4889-4894.
Higham, Eric, (2016) "The Compound Semiconductor Industry; How Did It Get Here and Where Is It Going?," SemiCon WEST Jul. 12-14, 2016 [http://www.semiconwest.org/sites/semiconwest.org/files/data15/docs/2_Eric%20Higham_Strategy%20Analytics.pdf], 27pp.
Honda et al. (2005) "Chemical Dry Cleaning Technology for Reliable 65nm CMOS contact to NiSix," IITC, paper 9.4.
International Preliminary Report on Patentability dated Dec. 10, 2020 issued in Application No. PCT/US2019/031165.
International Preliminary Report on Patentability dated Jan. 21, 2021 issued in Application No. PCT/US2019/040490.
International Preliminary Report on Patentability dated Jul. 4, 2019 issued in Application No. PCT/US2017/066470.
International Search Report and Written Opinion dated Apr. 6, 2022, for International Application No. PCT/US2021/062793.
International Search Report and Written Opinion dated Apr. 5, 2018 issued in Application No. PCT/US2017/066470.
International Search Report and Written Opinion dated Aug. 22, 2019 issued in Application No. PCT/US2019/031165.
International Search Report and Written Opinion dated Jul. 4, 2022, in PCT Application No. PCT/US2022/020421.
International Search Report and Written Opinion dated Oct. 31, 2019 issued in Application No. PCT/US2019/040490.
Jang et al. (2002) "Fabrication of MEMS devices by using anhydrous HF gas-phase etching with alcoholic vapor," Journal of Micromechanics and Microengineering, 12:297-306.
Japanese First Office Action dated Jan. 28, 2020 issued in Application No. JP 2015-250922.
JP Office Action dated Jan. 5, 2022, in Application No. JP2019-533041 with English translation.
JP Office Action dated May 31, 2022, in Application No. JP20190533041 with English Translation.
Kanarik et al. (Aug. 2018) "Atomic Layer Etching: Rethinking the Art of Etch" The Journal of Physical Chemistry Letters, vol. 9, pp. 4814-4821. doi:10.1021/acs.jpclett.8b00997.
Kanarik et al. (Mar/Apr. 2015) "Overview of atomic layer etching in the semiconductor industry," J. Vac. Sci. Technol. A, 33(2):020802-1-020802-14.
Kanarik et al. (Nov. 2016) "Tech Brief: All About ALE" [webpage] pp. 1-3. URL:https://blog.lamresearch.com/tech-brief-all-about-ale/.
Kim et al. (2003) "New Contact Cleaning in HF & N2/H2 Microwave Plasma," Solid State Phenomena, 92:239-242.
Kim, Jong Kyu, et al., (Nov./Dec. 2013) "Atomic layer etching removal of damaged layers in a contact hole for low sheet resistance," Journal of Vacuum Science & Technology, 31(6):8.
Korean Decision for Grant dated Jun. 11, 2021 issued in Application No. KR 10-2014-0097663.
Korean First Office Action dated Jan. 13, 2021 issued in Application No. KR 10-2014-0097663.
Korean Office Action dated Apr. 8, 2014, issued in KR 10-2008-0063247.
KR Office Action dated Dec. 7, 2022, in Application No. KR10-2022-0110480 with English translation.
KR Office Action dated Aug. 25, 2022, in Application No. KR10-2019-7020687 with English translation.
KR office action dated Dec. 24, 2021, in application No. KR1020210121005 with English translation.
KR Office Action dated Feb. 15, 2022, in Application No. KR1020160069175 with English translation.
KR Office Action dated Jan. 25, 2023 in Application No. KR10-2022-0059043 with English translation.
KR Office Action dated Jun. 1, 2022, in Application No. KR10-2021-0121005 with English translation.
KR Office Action dated Mar. 3, 2023, in Application No. KR10-2016-0124689.
KR Office action dated Nov. 14, 2021, in KR Application No. KR1020160069175 with English translation.
KR Office Action dated Oct. 25, 2022, in Application No. KR10-2016-0000444.
KR Office Action dated Sep. 13, 2022, in Application No. KR10-2019-7021389 With English Translation.
KR Office Action dated Sep. 28, 2022 in Application No. KR10-2016-0000420 with English translation.
Matsuo et al. (Sep./Oct. 1999) "Silicon etching in NF3/02 remote microwave plasmas," J. Vac. Sci. Technol. A, 17(5):2431-2437.
Meguro et al. (1990) "Digital etching of GaAs: New approach of dry etching to atomic ordered processing," American Institute of Physics pp. 1552-1554.
Metzler et al., (Mar/Apr. 2014) "Fluorocarbon assisted atomic layer etching of SiO2 using cyclic Ar/C4F8 plasma," Journal of Vacuum Science & Technology A, 32(2):5.
Natzle et al. (2004) "Trimming of hard-masks by Gaseous Chemical Oxide Removal (COR) for Sub-10nm Gates/Fins, for Gate Length Control and for Embedded Logic," 2004 IEEE/SEMI Advanced Semiconductor Manufacturing Conference, pp. 61-65.
Nishino et al. (1993) "Damage-free selective etching of Si native oxides using NH3/NF3 and SF6/H2O down-flow etching," J. Appl. Phys. 74(2):1345-1348.
Oehrlein, Gottlieb S., "Atomic Layer Etching of SiO2: Challenges And Opportunities*," University of Maryland, Atomic Layer Etch and Atomic Layer Clean Technology Workshop, San Francisco, Apr. 21, 2014, 27 pages.
Ogawa et al. (2002) "Dry Cleaning Technology for Removal of Silicon Native Oxide Employing Hot NH3/NF3 Exposure," The Japan Society of Applied Physics, Part I, No. 8, pp. 5349-5358.
Okamura et al. (2004) "Low Damage Via Formation with Low Resistance by NH3 Thermal Reduction for Cu / Ultra Low-k Interconnects," IEEE, pp. 42-44.
Park et al. (1996) "Low Damage In Situ Contact Cleaning Method by a Highly Dense and Directional ECR Plasma," Jpn J. Appl. Phys 35:1097-1101.
Park et al. (2005) "Atomic Layer Etching of Si(100) and Si(111) Using Cl2 and Ar Neutral Beam," Electrochemical and Solid-State Letters, 8(8) C106-C109.
Phan et al. (2006) "Integrated Clean Process Using NF3/NH3 Remote Plasma for Nickle Silicide Formation," SEMICON Korea STS 2006, pp. 159-163.
Singapore Notice of Allowance and Supplementary Examination Report dated Jul. 1, 2019 issued in Application No. SG 10201600021U.
Singapore Notice of Eligibility for Grant and Supplementary Examination Report SG application No. 10201606891S dated Jan. 9, 2020.

(56) References Cited

OTHER PUBLICATIONS

Taguwa et al. (2000) "ICP-Ar/H2 Precleaning and Plasma Damage-Free Ti-PECVD for Sub-Quarter Micron Contact of Logic with Embedded DRAM," Conference Proceedings USLI XV 2000, pp. 589-593.
Taiwan First Office Action dated dated Jun. 27, 2019 issued in Application No. TW 104143047.
Taiwan Notice of Allowance dated Oct. 1, 2019 issued in Application No. TW 104143047.
Taiwanese First Office Action at Re-exam dated May 13, 2021 issued in Application No. TW 105117488.
Taiwanese First Office Action dated Jan. 7, 2020 issued in Application No. TW 105117488.
Taiwanese First Office Action dated Jul. 23, 2020 issued in Application No. TW 106103603.
Taiwanese First Office Action dated Jun. 17, 2021 issued in Application No. TW 106144335.
Taiwanese First Office Action dated Oct. 24, 2017 issued in Application No. TW 103126076.
Taiwanese Second Office Action dated Jun. 23, 2020 issued in Application No. TW 105117488.
Taiwanese Second Office Action dated Oct. 8, 2018 issued in Application No. TW 103126076.
Torek et al. (1995) "Reduced pressure etching of thermal oxides in anhydrous HF/alcoholic gas mixtures" Journal of the Electrochemical Society, vol. 142, No. 4, Apr. 1995, pp. 1322-1326. ISSN:0013-4651.
TW Office Action dated Jan. 14, 2022, in Application No. TW106144335 with English translation.
TW Office Action dated Jul. 25, 2022 In Application No. TW110131208 With English translation.
U.S Advisory Action dated Sep. 14, 2022 in U.S. Appl. No. 17/250,326.
U.S. Corrected Notice of Allowance dated Jan. 5, 2023 in U.S. Appl. No. 17/250,326.
U.S. Advisory Action dated Feb. 11, 2022 in U.S. Appl. No. 17/103,519.
U.S. Final Office Action dated Dec. 2, 2021 in U.S. Appl. No. 17/103,519.
US Final Office Action, dated Dec. 23, 2010, issued in U.S. Appl. No. 12/341,943.
US Final Office Action, dated Jul. 17, 2007, issued in U.S. Appl. No. 11/479,812.
US Final Office Action, dated Jul. 2, 2014, issued in U.S. Appl. No. 13/244,032.
US Final Office Action dated Jul. 9, 2021 issued in U.S. Appl. No. 16/717,385.
US Final Office Action, dated Jun. 26, 2013, issued in U.S. Appl. No. 13/461,080.
US Final Office Action, dated May 21, 2019 issued in U.S. Appl. No. 15/216,257.
U.S. Final office Action dated May 31, 2022 in U.S. Appl. No. 17/250,326.
US Final Office Action, dated May 7, 2008, issued in U.S. Appl. No. 11/479,812.
US Final Office Action, dated Nov. 17, 2011, issued in U.S. Appl. No. 12/002,171.
US Final Office Action dated Sep. 16, 2019 issued in U.S. Appl. No. 15/841,205.
U.S. Non-Final Office Action dated Dec. 29, 2021, in U.S. Appl. No. 17/250,326.
US Notice of Allowance dated Apr. 10, 2018 issued in U.S. Appl. No. 15/173,358.
US Notice of Allowance dated Apr. 25, 2018 issued in U.S. Appl. No. 15/421,189.
US Notice of Allowance, dated Aug. 28, 2013, issued in U.S. Appl. No. 13/461,080.
US Notice of Allowance dated Dec. 2, 2019 issued in U.S. Appl. No. 15/841,205.
US Notice of Allowance dated Dec. 2, 2019 issued in U.S. Appl. No. 16/049,320.
U.S. Notice of Allowance dated Dec. 21, 2022 in U.S. Appl. No. 17/250,326.
U.S. Notice of Allowance dated Dec. 22, 2022 in U.S. Appl. No. 17/457,909.
US Notice of Allowance dated Feb. 10, 2020 issued in U.S. Appl. No. 15/216,257.
US Notice of Allowance, dated Feb. 3, 2012, issued in U.S. Appl. No. 12/002,085.
US Notice of Allowance dated Feb. 5, 2016 issued in U.S. Appl. No. 14/446,203.
US Notice of Allowance dated Jan. 29, 2018 issued in U.S. Appl. No. 15/173,358.
US Notice of Allowance, dated Jul. 1, 2008, issued in U.S. Appl. No. 11/479,812.
US Notice of Allowance, dated Jul. 12, 2016, issued in U.S. Appl. No. 14/590,801.
US Notice of Allowance, dated Jul. 13, 2011, issued in U.S. Appl. No. 12/174,402.
U.S Notice of Allowance dated Mar. 2, 2022, in U.S. Appl. No. 17/103,519.
US Notice of Allowance, dated Mar. 15, 2011, issued in U.S. Appl. No. 12/341,943.
US Notice of Allowance, dated Mar. 7, 2011, issued in U.S. Appl. No. 12/074,912.
US Notice of Allowance dated May 10, 2018 issued in U.S. Appl. No. 15/239,138.
US Notice of Allowance, dated May 2, 2016, issued in U.S. Appl. No. 14/589,610.
US Notice of Allowance, dated Sep. 14, 2011, issued in U.S. Appl. No. 12/343,102.
US Notice of Allowance dated Sep. 22, 2021 issued in U.S. Appl. No. 16/717,385.
US Office Action dated Apr. 10, 2019 issued in U.S. Appl. No. 15/841,205.
US Office Action, dated Apr. 12, 2011, issued in U.S. Appl. No. 12/002,085.
US Office Action, dated Apr. 21, 2011, issued in U.S. Appl. No. 12/343,102.
US Office Action, dated Apr. 9, 2015, issued in U.S. Appl. No. 14/531,483.
US Office Action dated Aug. 25, 2017 issued in U.S. Appl. No. 15/239,138.
US Office Action, dated Dec. 21, 2015, issued in U.S. Appl. No. 14/589,610.
US Office Action, dated Dec. 3, 2018, issued in U.S. Appl. No. 15/216,257.
US Office Action, dated Dec. 30, 2015, issued in U.S. Appl. No. 14/531,483.
US Office Action, dated Dec. 5, 2007, issued in U.S. Appl. No. 11/479,812.
US Office Action, dated Feb. 15, 2011, issued in U.S. Appl. No. 12/174,402.
US Office Action dated Feb. 26, 2021 issued in U.S. Appl. No. 16/717,385.
US Office Action, dated Feb. 3, 2011, issued in U.S. Appl. No. 12/244,241.
US Office Action, dated Jan. 17, 2013, issued in U.S. Appl. No. 13/461,080.
US Office Action, dated Jan. 29, 2010, issued in U.S. Appl. No. 12/144,518.
US Office Action dated Jul. 21, 2015 issued in U.S. Appl. No. 14/446,203.
US Office Action, dated Jun. 11, 2010, issued in U.S. Appl. No. 12/341,943.
US Office Action, dated Jun. 14, 2010, issued in U.S. Appl. No. 12/144,518.
US Office Action dated Jun. 4, 2021 issued in U.S. Appl. No. 17/103,519.
US Office Action, dated Jun. 9, 2011, issued in U.S. Appl. No. 12/002,171.

(56) References Cited

OTHER PUBLICATIONS

US Office Action, dated Mar. 1, 2016, issued in U.S. Appl. No. 14/590,801.
US Office Action, dated May 2, 2007, issued in U.S. Appl. No. 11/479,812.
US Office Action dated May 23, 2017 issued in U.S. Appl. No. 15/173,358.
US Office Action, dated Nov. 22, 2013, issued in U.S. Appl. No. 13/244,032.
US Office Action dated Nov. 29, 2017 issued in U.S. Appl. No. 15/421,189.
US Office Action, dated Sep. 23, 2019 issued in U.S. Appl. No. 15/216,257.
US Office Action, dated Sep. 30, 2011, issued in U.S. Appl. No. 12/002,085.
US Office Action dated Sep. 6, 2019 issued in U.S. Appl. No. 16/049,320.
U.S. Appl. No. 12/002,171, Inventors Van Schravendijk et al., filed Dec. 14, 2007.
U.S. Appl. No. 12/144,518, Inventors Drewery et al., filed Jun. 23, 2008.
U.S. Appl. No. 12/244,241, Inventors Drewery et al., filed Oct. 2, 2008.
U.S. Appl. No. 13/244,032, Inventors Draeger et al., filed Sep. 23, 2011.
U.S. Appl. No. 18/003,257, inventors Routzahn et al., filed Dec. 23, 2022.
Volatier, M., et al., "Extremely high aspect ratio GaAs and GaAs/AlGaAs nanowaveguides fabricated using chlorine ICP etching with N2-promoted passivation," Nanotechnology, vol. 21, Mar. 8, 2010, pp. 1-8. doi:10.1088/0957-4484/21/13134014.
Wang et al. (1998) "Ultrahigh-selectivity silicon nitride etch process using an inductively coupled plasma source," J. Vac. Sci. Technol. A, 16(3):1582-1587.
Yun et al. (2007) "Large Etch Rate Enhancement by NO-Induced Surface Chemical Reaction during Chemical Dry Etching of Silicon Oxide in F2 Remote Plasmas" Journal of The Elctrochemical Society, vol. 154, No. 4, pp. D267-D272.
CN Office Action dated Jan. 16, 2025 in CN Application No. 201980046595.5, with English Translation.
KR Notice of Allowance dated Feb. 21, 2025 in KR Application No. 10-2017-0014362, with English Translation.
KR Office Action dated Dec. 27, 2024 in KR Application No. 10-2021-7003963, with English Translation.
KR Office Action dated Dec. 27, 2024 in KR Application No. 10-2024-0041161, with English Translation.
U.S. Non-Final Office Action dated Feb. 12, 2025 in U.S. Appl. No. 17/805,081.
U.S. Appl. No. 19/106,145, inventors Routzahn A.L et al., filed on Feb. 24, 2025.
U.S. Restriction Requirement dated Feb. 6, 2025 in U.S. Appl. No. 18/002,788.
U.S. Restriction Requirement dated Jan. 15, 2025 in U.S. Appl. No. 18/003,257.

\* cited by examiner

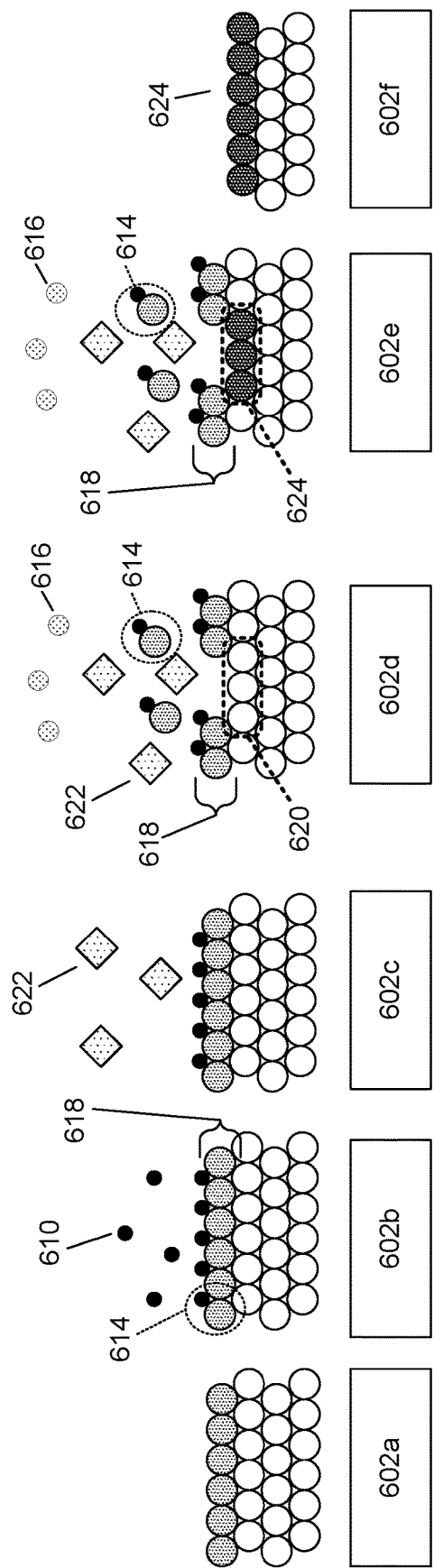
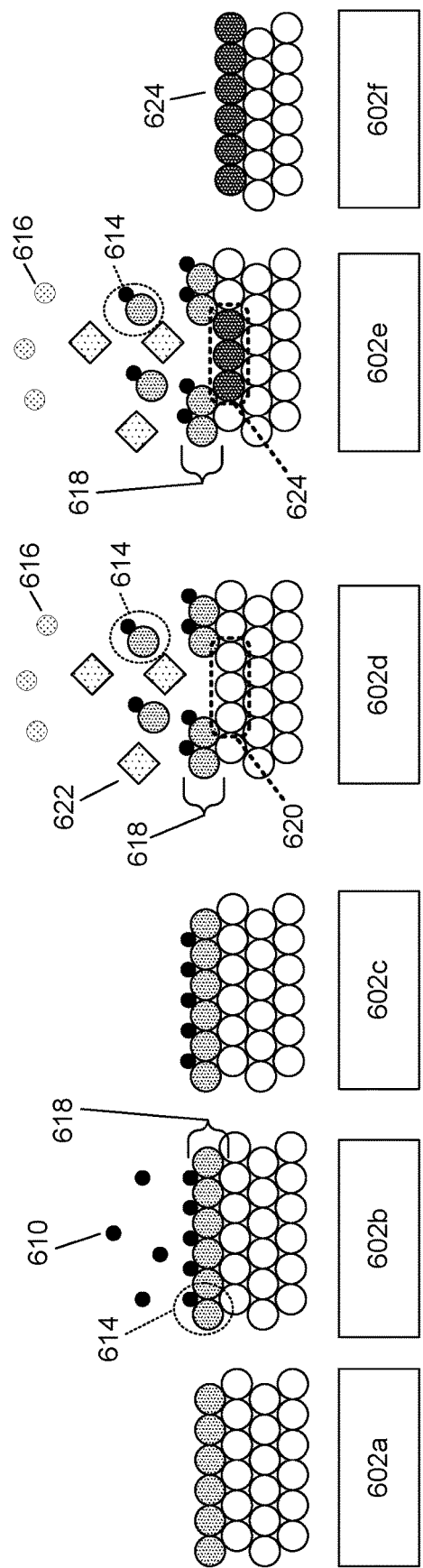
Figure 6C
Figure 6D

ETCH SELECTIVITY CONTROL IN ATOMIC LAYER ETCHING

RELATED APPLICATIONS

A PCT request form is filed concurrently with this specification as part of the present application. Each application that the present application claims benefit of or priority to as identified in the concurrently filed PCT request form is incorporated by reference herein in its entirety and for all purposes.

BACKGROUND

Semiconductor fabrication often involves patterning schemes and other processes whereby some materials are selectively etched to prevent etching of other exposed surfaces of a substrate. As device geometries become smaller and smaller, high etch selectivity processes are desirable to achieve effective etching of desired materials without etching of other materials.

The background description provided herein is for the purposes of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

The systems, methods and devices of this disclosure each have several innovative aspects, no single one of which is solely responsible for the desirable attributes disclosed herein. Included among these aspects are at least the following implementations, although further implementations may be set forth in the detailed description or may be evident from the discussion provided herein.

In some embodiments, a method may be provided. The method may include providing a substrate to a processing chamber, the substrate having a first material adjacent to and covering a surface of a second material, modifying a layer of the first material by flowing a first process gas onto the substrate and thereby creating a modified layer of the first material, removing the modified layer of the first material by flowing a second process gas onto the substrate, and converting, when the surface of the second material is uncovered via removal of the modified layer, the surface to a converted layer of the second material by flowing a third process gas onto the substrate, in which the first and second process gases are less reactive with the converted layer than with the first material and the second material.

In some embodiments, the method may further include modifying, after the converting, the converted layer to a modified converted layer of material by flowing a fourth process gas onto the substrate, and removing the modified converted layer by flowing a fifth process gas onto the substrate.

In some embodiments, flowing the third process gas may occur before the modifying.

In some embodiments, flowing the third process gas may occur after the modifying.

In some such embodiments, flowing the third process gas may occur before the removing.

In some further such embodiments, the method may further include flowing a purge gas after flowing the third process gas and before the removing.

In some such embodiments, flowing the third process gas may occur after the removing.

In some embodiments, flowing the third process gas onto the substrate may at least partially overlap with flowing the first process gas onto the substrate.

In some embodiments, flowing the third process gas onto the substrate may at least partially overlap with flowing the second process gas onto the substrate.

In some embodiments, flowing the third process gas onto the substrate may at least partially overlap with flowing the first process gas onto the substrate and with flowing the second process gas onto the substrate.

In some embodiments, the converting may occur when the surface of the second material is uncovered during or after the removing of the first material.

In some embodiments, during the removing, the second process gas may remove the modified layer of the first material at a first etch rate, during the removing, the second process gas may remove the converted layer at a second etch rate that is about equal to or less than 50% of the first etch rate.

In some such embodiments, the second etch rate may be about equal to or less than 15% of the first etch rate.

In some such embodiments, during the removing, the second process gas may be capable of removing the second material at a third etch rate higher than the first etch rate.

In some embodiments, the first process gas may include modifying molecules, the second process gas may include removal molecules, and the third process gas may include converting molecules.

In some embodiments, the third process gas may include a precursor.

In some embodiments, the converted layer may be a monoatomic layer of the second material.

In some embodiments, the first material and the second material may be oxides.

In some embodiments, the first material and/or the second material may be semiconductor oxides.

In some embodiments, the converted layer may be passive to the second process gas.

In some embodiments, a reaction between the converted layer and the second process gas may not produce byproducts.

In some embodiments, the method may further include repeating the modifying and the removing to remove an amount the first material before the converting.

In some embodiments, the first material may include an aluminum oxide, the second material may include a zinc oxide, the first process gas may include a hydrogen fluoride, the second process gas may include trimethylaluminum, the third process gas may include zirconium tetrachloride, and the converted layer may include a zirconium oxide.

In some embodiments, the method may further include removing the converted layer by flowing a fourth process gas onto the substrate, in which the fourth process gas comprises dimethylaluminum chloride.

In some embodiments, the converting may include a cation exchange between an element in the third process gas and the second material.

In some embodiments, the modifying and the removing may occur while the substrate is maintained at the same, or substantially the same, temperature.

In some embodiments, the modifying may occur while the substrate is maintained at a first temperature, and the removing may occur while the substrate is maintained at a second temperature different than the first temperature.

In some embodiments, during the converting, water vapor may not be provided to the substrate.

In some embodiments, a method may be provided. The method may include providing a substrate to a processing chamber, the substrate having a first material adjacent to and covering a surface of a second material, modifying a layer of the first material by flowing a first process gas onto the substrate and thereby creating a modified layer of the first material, removing the modified layer of the first material by flowing a second process gas onto the substrate, and selectively converting, when the surface of the second material is uncovered via removal of the modified layer, the surface of the second material to a layer of etch stop material, and the layer of etch stop material is only positioned on top of the second material, such that during the removing, the modified layer of the first material and the layer of etch stop material are exposed to the second process gas and the second process gas is less reactive with the layer of etch stop material than with the modified layer of the first material and the second material.

In some embodiments, an apparatus for semiconductor processing may be provided. The apparatus may include a processing chamber that includes an interior and a substrate support configured to support a substrate in the interior, a process gas unit configured to flow a first process gas comprising a modifying molecule onto the substrate in the processing chamber, a second process gas comprising a removal molecule onto the substrate in the processing chamber, and a third process gas comprising a conversion molecule onto the substrate in the processing chamber, and a controller with instructions that are configured to cause the first process gas to flow onto the substrate and thereby create a modified layer of a first material on the substrate, in which the substrate has the first material adjacent to and covering a surface of a second material, cause the second process gas to flow onto the substrate and thereby remove the modified layer of the first material, and cause the third process gas to flow onto the substrate to convert, when the surface of the second material is uncovered, the surface to a converted layer of the second material, in which the first and second process gases are less reactive with the converted layer than with the first material and the second material.

BRIEF DESCRIPTION OF THE DRAWINGS

FIGS. 6A through 6D further illustrate various flows of the third process gas onto the wafer.

DETAILED DESCRIPTION

Figure 1:
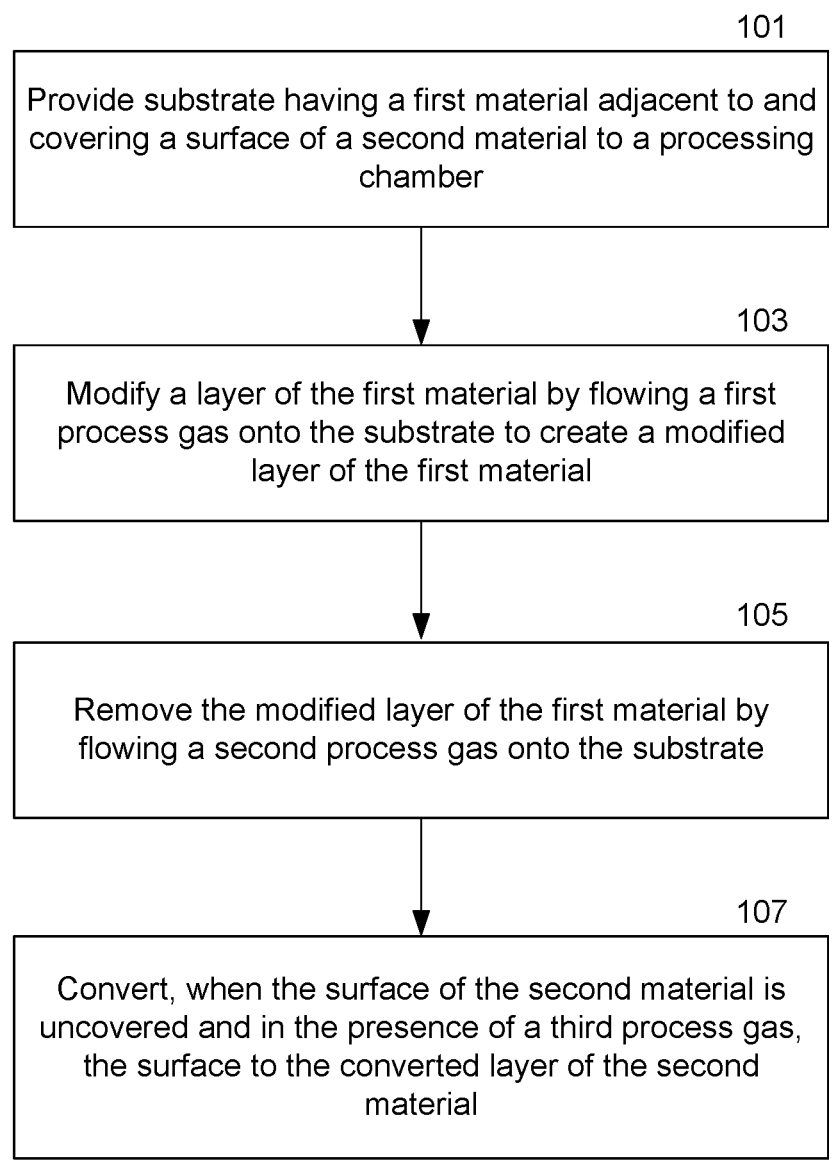
FIG. 1 depicts an example process flow diagram for performing operations in accordance with disclosed embodiments.

In the following description, numerous specific details are set forth to provide a thorough understanding of the presented embodiments. The disclosed embodiments may be practiced without some or all of these specific details. In other instances, well-known process operations have not been described in detail to not unnecessarily obscure the disclosed embodiments. While the disclosed embodiments will be described in conjunction with the specific embodiments, it will be understood that it is not intended to limit the disclosed embodiments.

In this application, the terms "semiconductor wafer," "wafer," "substrate," "wafer substrate," and "partially fabricated integrated circuit" are used interchangeably. One of ordinary skill in the art would understand that the term "partially fabricated integrated circuit" can refer to a silicon wafer during any of many stages of integrated circuit fabrication thereon. A wafer or substrate used in the semiconductor device industry typically has a diameter of 200 mm, or 300 mm, or 450 mm. The following detailed description assumes the invention is implemented on a wafer. However, the invention is not so limited. The work piece may be of various shapes, sizes, and materials. In addition to semiconductor wafers, other work pieces that may take advantage of this invention include various articles such as printed circuit boards, magnetic recording media, magnetic recording sensors, mirrors, optical elements, micro-mechanical devices and the like.

Introduction and Context

Semiconductor fabrication processes often involve patterning and etching of various materials, including conductors, semiconductors, and dielectrics. Some examples include conductors, such as metals or carbon; semiconductors, such as silicon or germanium; and dielectrics, such as silicon oxide, aluminum oxide, zirconium dioxide, hafnium dioxide, silicon nitride, and titanium nitride. Atomic layer etching ("ALE") processes remove thin layers of material using sequential self-limiting reactions. Generally, an ALE cycle is the minimum set of operations used to perform an etch process one time, such as etching a monolayer. The result of one ALE cycle is that at least some of a film layer on a substrate surface is etched. Typically, an ALE cycle includes a modification operation to form a reactive layer, followed by a removal operation to remove or etch only this reactive layer. The cycle may include certain ancillary operations such as removing one of the reactants or byproducts, as well as a cleaning operation to remove residues that have built up on surfaces of the processing chamber. Generally, a cycle contains one instance of a unique sequence of operations.

As an example, an ALE cycle may include the following operations: (i) delivery of a first process gas that is a reactant gas, (ii) purging of the reactant gas from the chamber, (iii) delivery of a second process gas that is a removal gas and an optional plasma, and (iv) purging of the chamber. In some embodiments, etching may be performed nonconformally. In some instances, a cleaning operation may be performed after one or more cycles to remove residues that have built up on surfaces of the processing chamber. The modification operation generally forms a thin, reactive surface layer with a thickness less than the un-modified material, such as one, two, or three, atomic layers thick, for instance, or less than a whole atomic layer in one cycle.

Some implementations of the ALE processes described herein may rely upon chemical reactions in conjunction maintaining the substrate at a particular temperature or temperature range to drive chemical reactions in the modification and/or the removal operations which may be considered "thermal ALE". In some embodiments, this thermal ALE may be considered an isotropic etch. In some embodiments, one or more layers of the substrate may be modified with chemical adsorption (hereinafter "chemisorption"), not with a plasma, while the substrate is maintained at a first temperature, after which the one or more modified layers of the substrate may be removed with desorption, not with a plasma, while the substrate is at a second temperature. In some embodiments, the first and second temperatures may be the same, while in some other embodiments they may be different than each other. Chemisorption and desorption are temperature dependent chemical reactions that may occur in separate temperature regimes, may occur in partially overlapping temperature regimes, or may occur in the same temperature regime. Because of this, some of the thermal ALE techniques described herein maintain the temperature of the substrate at the same, or substantially the same, temperature during the modification and removal operations. Some other embodiments modulate the temperature of the substrate between the modification and removal operations in order to enable and utilize chemisorption that occurs at one temperature for the modification operation, and to enable and utilize desorption that occurs at a different temperature for the removal operation.

In some embodiments of thermal ALE, a plasma may be used during the modification operation and not during the removal operation, while in some other embodiments, a plasma may be used during both the modification and removal operations, along with varying temperatures during these operations.

In some thermal ALE processes, one or more surface layers of material are modified by chemisorption while the substrate is maintained at a first temperature; this may result in the creation of one or more modified surface layers of the substrate. The substrate includes layers of material and exposed surfaces that may be a uniform layer of material or may be a non-uniform layer that includes different molecules and elements. A first process gas with modifying molecules may be flowed onto the substrate that is maintained at the first temperature. In some embodiments, the modifying molecules may include a halogen, such as fluorine, in order to halogenate exposed molecules on the substrate, while some embodiments may include oxygen in order to oxidize exposed molecules on the substrate. The first process gas may also include a carrier gas, such as $N_2$, Ar, He, and Ne. This first temperature allows for chemisorption between the modifying molecules and at least some of the molecules in the exposed surface(s) of material.

Figure 2:
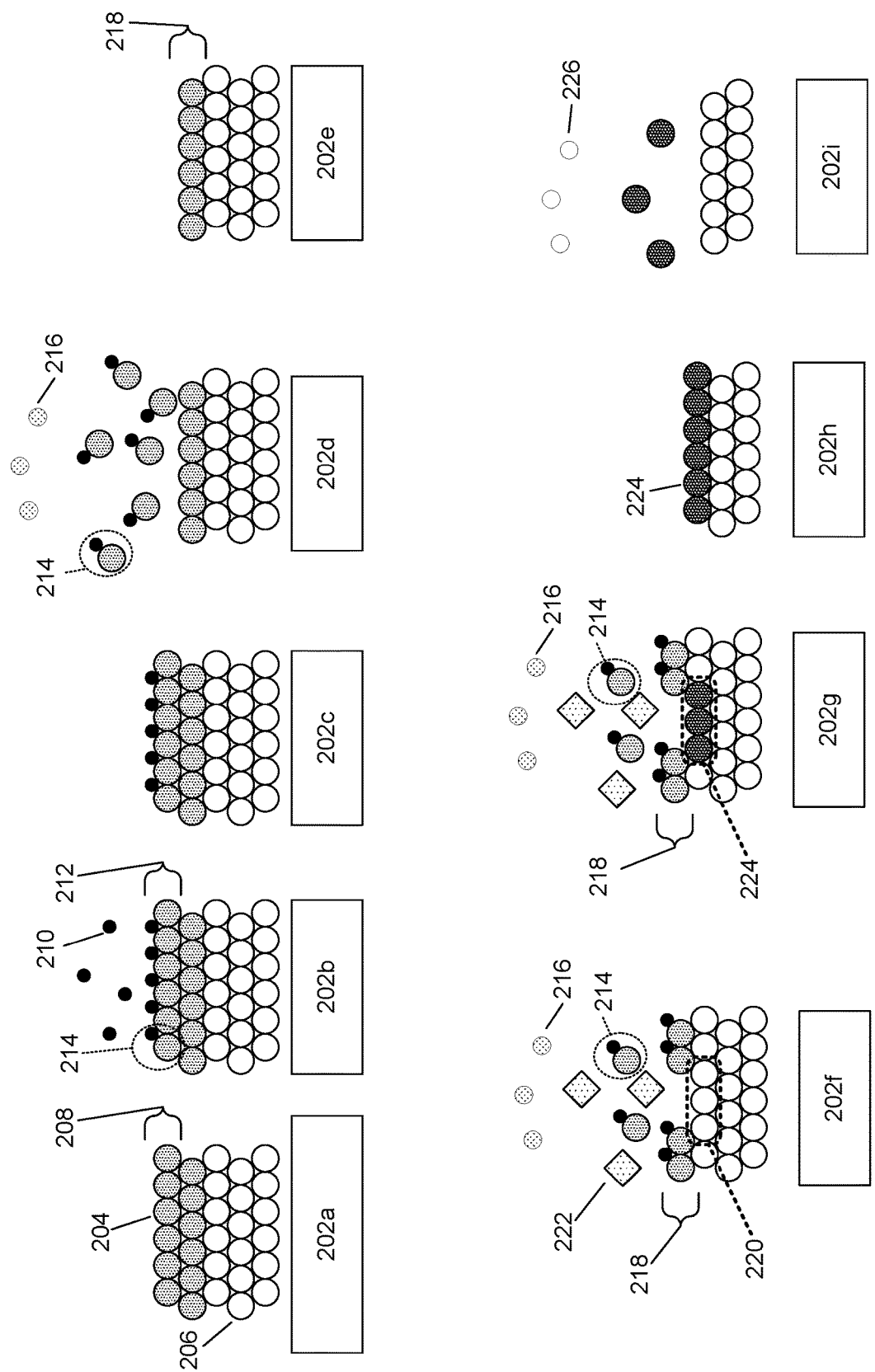
FIG. 2 depicts an example schematic illustration of atomic layer etching in accordance with disclosed embodiments.
Figure 3:
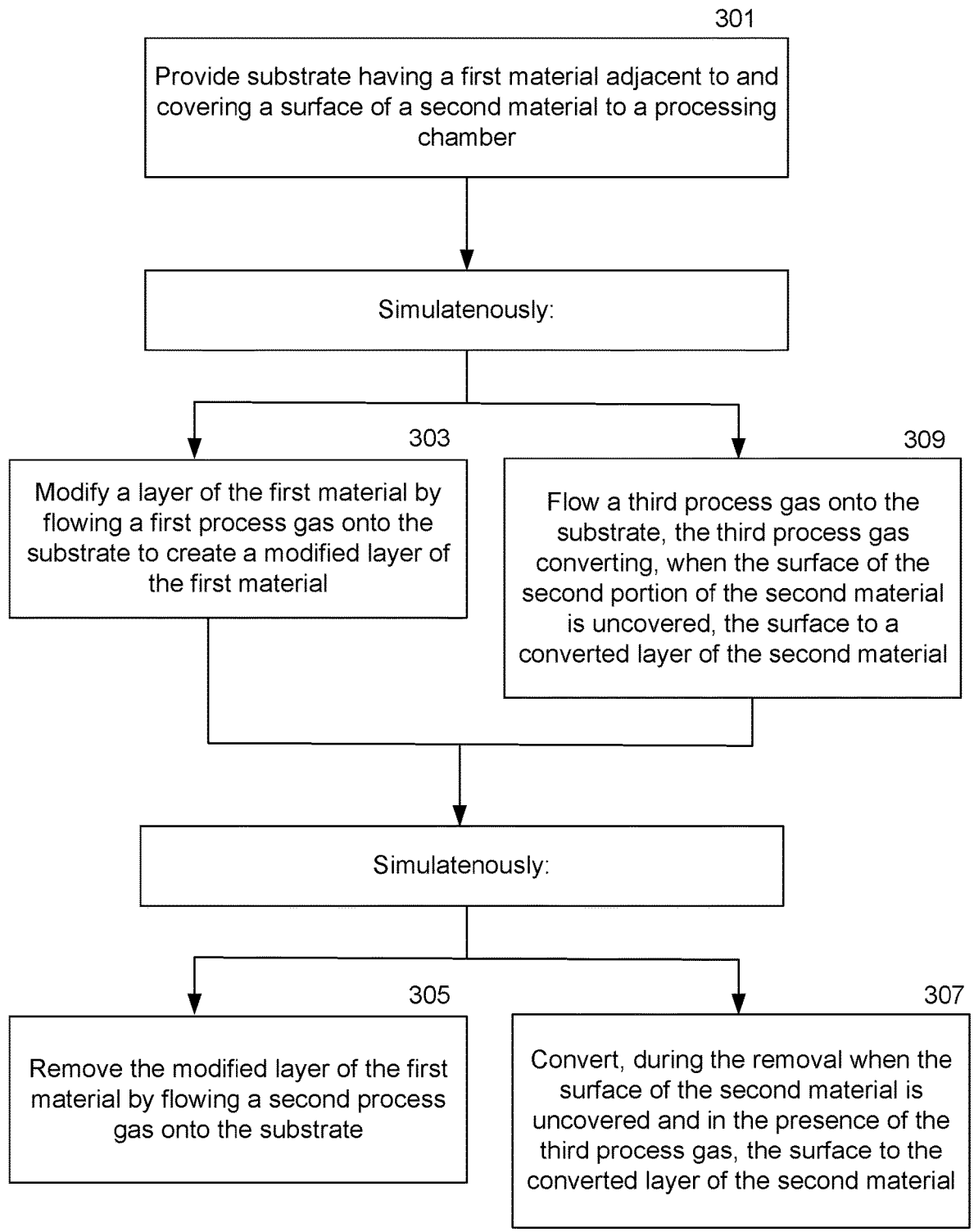
FIG. 3 depicts another example process flow diagram for performing operations in accordance with disclosed embodiments.

Although the term "first temperature" is used, the temperatures discussed herein may be considered both a specific temperature, or may be a temperature range like highlighted in FIGS. 2 and 3. In some embodiments, the first temperature may be between about 20° C. and 500° C., about 20° C. and 150° C., about 20° C. and 100° C., about 20° C. and 80° C., about 200° C. and 600° C., about 200° C. and 500° C., about 200° C. and 350° C., or about 350° C. and 500° C., for example. Additionally, the substrate may be maintained at the temperature during all, or substantially all (e.g., at least 80%, 90%, or 95%), of the modification operation. The duration of the modification operation may be the duration for which modification of substantially all (e.g., at least 80%, 90%, or 95%) of desired exposed molecules on the substrate occurs. This may range from about 0.5 seconds to about 10 seconds, 0.5 seconds to about 5 seconds, about 1 second to about 5 seconds, or about 30 seconds to two minutes, for example.

After the modification operation, an optional purge operation may be performed. In some of the embodiments in which the modification and removal operations are performed at different temperatures, after the modification operation, the temperature of the substrate may be brought to a second temperature, and an optional purge operation may be performed. This second temperature may be the temperature at which desorption occurs for the one or more modified surface layers. In some embodiments, the second temperature may be greater than the first temperature and the temperature of substrate may be raised from the first temperature to the second temperature. In some other embodiments, the second temperature may be less than the first temperature, and in these embodiments, the temperature of the substrate may be actively cooled from the first temperature to the second temperature. The substrate may be heated using radiant heating, convection heating, solid-to-solid heat transfer, or with a plasma. Additionally, the substrate top, bottom, or both, may be heated. The heating of the substrate may also occur in a non-linear fashion, in some embodiments, and the substrate may be actively cooled in various manners. As noted above, in some embodiments, the second temperature may be the same, or substantially the same, as the first temperature such that the modification and removal operations are performed at the same, or substantially the same, temperature.

The one or more modified surface layers may be removed while the substrate is maintained at the second temperature. In some embodiments, the second temperature alone may enable and cause desorption of the modified molecules from the substrate thereby removing the modified molecules from the substrate. In some other embodiments, a second process gas with removal molecules may be flowed onto the substrate, including onto the exposed surfaces of the substrate. The second process gas may also include a carrier gas as described above. These removal molecules may react with the modified molecules to form a different volatile molecule, which may be considered a volatized molecule. This volatized molecule may in turn be removed from the substrate by desorption when the substrate is at the second temperature. In some embodiments, this flowing of the second process gas may be part of the removal operation or may be a separate operation that occurs before, after, or during the heating of the substrate.

In some embodiments, the second temperature may be the same or different than the first temperature, and may range between about 20° C. and 500° C., about 20° C. and 150° C., about 20° C. and 100° C., about 20° C. and 80° C., about 200° C. and 600° C., about 200° C. and 500° C., about 200° C. and 350° C., or about 350° C. and 500° C., for example. Additionally, the substrate may be maintained at the temperature during all, or substantially all (e.g., at least 80%, 90%, or 95%), of the removal operation. The duration of the removal operation may be the duration for which desorption of substantially all (e.g., at least 80%, 90%, or 95%) of desired molecules on the substrate occurs. This may range from about 0.5 seconds to about 10 seconds, about 0.5 seconds to about 5 seconds, about 1 second to about 5 seconds, about 0.5 seconds to two minutes, or about 30 seconds and two minutes.

In some other ALE processes, ionic energy, such as from a plasma, may be used to drive the modification and/or the removal operations. In an example modification operation, a substrate may be chlorinated by introducing chlorine into the chamber. Chlorine is used as an example etchant species or etching gas, but it will be understood that a different etching gas may be introduced into the chamber. The etching gas may be selected depending on the type and chemistry of the substrate to be etched. A plasma may be ignited and chlorine reacts with the substrate for the etching process; the chlorine may react with the substrate or may be adsorbed onto the surface of the substrate. The species generated from a plasma can be generated directly by forming a plasma in the process chamber housing the substrate or they can be generated remotely in a process chamber that does not house the substrate, and can be supplied into the process chamber housing the substrate.

In some instances, a purge may be performed after any of the operations described herein, including after the modification and/or removal operations. In a purge operation, non-surface-bound active modifying molecules, such as a chlorine or halogen species, may be removed from the process chamber. This can be done by purging and/or evacuating the process chamber to remove the active species, without removing the adsorbed layer. In some implementations that use a plasma, the species generated in a plasma can be removed by stopping the plasma and allowing the remaining species to decay, optionally combined with purging and/or evacuation of the chamber. Purging can be done using any inert gas such as N2, Ar, Ne, He and their combinations.

In a removal operation utilizing a plasma, the substrate may be exposed to an energy source to etch the substrate by directional sputtering (this may include activating or sputtering gas or chemically reactive species that induce removal). In some embodiments, the removal operation may be performed by ion bombardment using argon or helium ions. During removal, a bias may be optionally turned on to facilitate directional sputtering. In some embodiments, ALE may be isotropic; in some other embodiments ALE is not isotropic when directional ions are used in the removal process.

In various examples, the modification and removal operations of thermal ALE and plasma-assisted ALE may be repeated in cycles, such as about 1 to about 30 cycles, or about 1 to about 20 cycles. Any suitable number of ALE cycles may be included to etch a desired amount of film. In some embodiments, ALE is performed in cycles to etch about 1 Angstroms (Å) to about 50 Å of the surface of the layers on the substrate. In some embodiments, cycles of ALE etch between about 2 Å and about 50 Å of the surface of the layers on the substrate. In some embodiments, each ALE cycle may etch at least about 0.1 Å, 0.5 Å, 1 Å, 2 Å, or 3 Å.

In some instances, prior to etching, the substrate may include a blanket layer of material, such as silicon or germanium. The substrate may include a patterned mask layer previously deposited and patterned on the substrate. For example, a mask layer may be deposited and patterned on a substrate including a blanket amorphous silicon layer. The layers on the substrate may also be patterned. Substrates may have "features" such as via or contact holes, which may be characterized by one or more of narrow and/or re-entrant openings, constrictions within the feature, and high aspect ratios. One example of a feature is a hole or via in a semiconductor substrate or a layer on the substrate. Another example is a trench in a substrate or layer. In various instances, the feature may have an under-layer, such as a barrier layer or adhesion layer. Non-limiting examples of under-layers include dielectric layers and conducting layers, e.g., silicon oxides, silicon nitrides, silicon carbides, metal oxides, metal nitrides, metal carbides, and metal layers. Another example feature may include overhangs or shelves that may require an etch in a location that may not be accessible with directional ions.

In some thermal ALE and/or plasma-assisted ALE processes, it is desirable to etch a target material without etching another material covered by the target material, sometimes described as etching the target material with selectivity to the other material. With some materials and etching chemistries, typical ALE processing and chemistry cannot achieve this selectivity. In some of these typical ALE processes, when the etch front removes the target material and reaches the underlying other material, it may undesirably continue etching and removing that other material. This undesirable etching may occur when etching, for example, high-k dielectrics, high-k oxides, semiconductors, metals, or other oxides that are covering other high-k dielectrics, high-k oxides, semiconductors, metals. Some of these conventional ALE processes therefore do not have the ability to remove one high-k oxide with selectivity to another high-k oxide or to a semiconductor.

Etching Techniques with High Selectivity

Provided herein are techniques and apparatuses for increasing etch selectivity between materials. This includes etching one material, referred to as the target material, that covers another material and reducing and/or limiting the etching of this other material. Some embodiments may include introducing a third process gas that creates an etch stop layer which prevents and/or reduces the etching of the underlying material. This third process gas may also cause limited to no etching of the target material. In some embodiments, the third process gas may be considered both a gas in which substantially all (e.g., at least 99% or more) of its constituents are in the gas phase, as well as a vapor in which its constituents may be in both the gas phase and liquid phase as suspended droplets. In some implementations, the etch stop layer may be a deposited layer of material that is selectively deposited onto the underlying material. The etch stop layer, whether a converted layer or a deposited layer, may be considered less reactive with the etching chemistry than the second layer of material and the modified layer of material which limits and reduces the etching of this etch stop material relative to the second layer of material and the modified layer of material.

In some implementations, the etch stop layer may be created by converting an exposed surface of the underlying material to a converted layer that is capable of withstanding the etching chemistry used to remove the target material. This etch stop layer, or converted layer, is formed by a conversion of the layer of the underlying material which, in some instances, may be achieved by a cation exchange between the third process gas and the underlying material without altering the composition of the target material or interfering with the primary etch chemistry used to etch the target material. This may be a conversion of at least one monoatomic layer of that material. In some implementations, the etch stop layer is formed via conversion of the surface of the underlying material, when the surface is exposed, using vaporous compounds. The third process supplies a cationic constituent in the vapor phase for this conversion; the remaining elements of this conversion are provided by the surface of the underlying material. In some embodiments, the cationic constituents of the underlying material are converted to volatile molecules that leave the surface of, or desorb from, the substrate. The cation in the third process gas, e.g., the incoming vapor, exchanges its ligands (e.g., a chlorine) with the ligand on the surface (e.g., oxygen), and thereby becomes solid or nonvolatile.

Additionally, it is desirable in some implementations to have the etching chemistry, the third process gas, and the resulting etch stop layer be compatible with each other so that, for example, the etching of the first material can continue while the conversion layer is being formed and protecting the underlying layer of material, and/or so that the etching chemistry does not react with the third process gas or etch the etch stop layer. For example, the first material may not be etched at the same time and/or rate at various locations on and/or across the whole wafer. For various reasons, some etching processes begin at the center of a wafer and continue radially outwards thereby etching a center region before an edge region. This may cause the removal of the desired amount of material in the center region faster than in the edge region, which may require the etching chemistry to continue flowing onto the wafer after the desired material has been removed from some parts of the wafer.

In another example, the first material may be deposited on the sides and bottom of a hole (or via, or trench), and may cover the second material that is also in the hole, and because etch rates of horizontal surfaces are sometimes less than etch rates of vertical surfaces, the bottom and/or top of the hole of the hole, via, or trench may be etched to expose the second material before the first material is removed on the sides of the hole. This may require continuing the etching within the hole to remove the first material on the sides of the hole while the second material is exposed at the bottom and/or top of the hole. It is therefore desirable in some implementations to form the conversion layer on the wafer where the etching has exposed the underlying material while simultaneously allowing the etching of the first material to continue on the wafer. Accordingly, some implementations provided herein use conversion molecules and etching chemistry that do not adversely affect one another so that the etching of the first material can continue on the wafer while the conversion layer is also formed when the underlying material is exposed by that etching.

The chemistry used to etch the target material may etch the etch stop layer at an etch rate less the etch rate of the target material and/or the other material, such as less than or equal to 50%, 25%, 15%, 10%, 5%, 1%, 0.1%, or 0.05% of the etch rate of the target material and/or the other material.

As discussed in more detail below, the third process gas may be introduced during various aspects of the processing. This may include co-flowing the third process gas during one or more ALE cycles, during an ALE process step such as the modifying or the removing, and/or flowing the third process gas while other process gases are not flowed, such as in-between removing and modifying operations. An example process may include performing the modification operation, followed by a purge, followed by flowing the third process gas, followed by another purge, and then followed by the removal operation. Optionally, the conversion layer may be removed by a separate modification operation with a different modifying molecule and a separate removal operation with a different removal molecule.

FIG. 1 depicts an example process flow diagram for performing operations in accordance with disclosed embodiments. In block 101, a wafer is provided to a processing chamber configured to performing etching of the wafer. The wafer may have at least two materials deposited thereon, with a first material adjacent to and covering a surface of a second material. This covering may be a vertical covering such that when the wafer is positioned on its bottom surface, the first and second materials are vertically arranged with the first material above and covering the second material. This covering may alternatively or additionally be a horizontal covering such that when the wafer is positioned on its bottom surface, the first and second materials are horizontally arranged with respect to each other with the first material covering the second material. In some embodiments, both the covering may be both vertical and horizonal coverings. As mentioned above, this may include the first material covering the second material along the sidewalls of a hole, via, or trench which poses an additional challenge because etch rates on horizontal surfaces may exceed those on vertical surfaces. In one single hole or via, etching of the vertical surface must continue while the conversion layer is formed and forming on the horizontal surface.

In block 103, a modification operation of the first material, also considered the target material, may be performed. The modification operation may include flowing a first process gas comprising a modifying molecule onto the wafer to form a thin, reactive surface layer that is more easily removed than the un-modified material in the subsequent removal operation. These modifying molecules may include, for example, halogen species such as chlorine or fluorine. Fluorine is used as an example etchant species in disclosed embodiments, and it may be flowed onto the substrate as hydrogen fluoride (HF), but it will be understood that in some embodiments, a different etching gas is introduced into the chamber. The etching gas may be selected depending on the type and chemistry of the substrate to be etched.

In some embodiments, an activation energy may be provided to assist with overcoming the activation barrier for the modifying molecule to adsorb on the semiconductor. This activation energy may be provided with thermal energy, radical energy, or both, which may include heating the substrate and/or generating a plasma or photons. This adsorption of the modifying molecule onto the first material may be considered chemical adsorption or "chemisorption" which is an energy dependent (e.g., a temperature dependent) chemical reaction. For some thermal ALE techniques, this chemisorption during the modification operation may only occur at a particular temperature range that enables the activation barrier of the molecules in the layer of material and the incoming modifying molecules to be overcome which allows for dissociation and chemical bonding between these molecules and an adsorbate in the modifying molecule. Outside of this temperature range, the chemisorption may not occur, or may occur at undesirable (e.g., slow) rates.

Accordingly, some implementations of block 103 include one or more surface layers of material are modified by chemisorption while the substrate is maintained at a first temperature; this may result in the creation of one or more modified surface layers of the substrate. The substrate includes layers of material and exposed surfaces that may be a uniform layer of material or may be a non-uniform layer that includes different molecules and elements. A first process gas with modifying molecules may be flowed onto the substrate that is maintained at the first temperature. In some embodiments, the modifying molecules may include a halogen, such as fluorine, in order to halogenate exposed molecules on the substrate, while some embodiments may include oxygen in order to oxidize exposed molecules on the substrate. In various embodiments, modifying molecules are introduced into the chamber in a gaseous form or vapor form (e.g., including both gas liquid forms) and may be optionally accompanied by a carrier gas such as nitrogen, argon, helium, or neon, for instance. This first temperature allows for chemisorption between the modifying molecules and at least some of the molecules in the exposed surface(s) of material.

Although the term "first temperature" is used, the temperatures discussed herein may be considered both a specific temperature, or may be a temperature range like highlighted in FIGS. 2 and 3. In some embodiments, the first temperature may be between about 20° C. and 500° C., about 20° C. and 150° C., about 20° C. and 100° C., about 20° C. and 80° C., about 200° C. and 600° C., about 200° C. and 500° C., about 200° C. and 350° C., or about 350° C. and 500° C., for example. Additionally, the substrate may be maintained at the temperature during all, or substantially all (e.g., at least 80%, 90%, or 95%), of the modification operation. The duration of the modification operation may be the duration for which modification of substantially all (e.g., at least 80%, 90%, or 95%) of desired exposed molecules on the substrate occurs. This may range from about 0.5 seconds to about 10 seconds, 0.5 seconds to about 5 seconds, or about 1 second to about 5 seconds, for example.

In some implementations that utilize plasma-assisted modification, the species generated from a plasma, for instance, can be generated directly by forming a plasma in the process chamber housing the substrate or they can be generated remotely in a process chamber that does not house the substrate, and can be supplied into the process chamber housing the substrate.

Although not shown in FIG. 1, an optional purge operation may be performed after block 103. In a purge operation, non-surface-bound active modifying molecules, such as the fluorine or chlorine species, may be removed from the process chamber, the chamber walls, the chamber gas volume, and/or the substrate. This can be done by purging and/or evacuating the process chamber to remove the active species, without removing the adsorbed layer. The species generated in a plasma can be removed by stopping the plasma and allowing the remaining species to decay, optionally combined with purging and/or evacuation of the chamber. Purging can be done using any inert gas such as $N_2$, Ar, Ne, He and their combinations.

In block 105, a removal operation of the modified layer of the first material is performed. This may include flowing a second process gas comprising removal molecules onto the substrate and exposing the wafer to an energy source, such as thermal energy, a plasma, or activating or sputtering gas or chemically reactive species that induces removal, such as argon or helium, to etch the substrate by directional sputtering. For some thermal ALE implementations, the removal operation may occur at the same, or substantially the same temperature, as the removal operation (i.e., at the first temperature). In some other thermal ALE implementations, the removal operation may occur at a second temperature or temperature range different than the first temperature range of the modification operation of block 103.

For desorption, a particular temperature range enables the activation barrier of the modified molecule to be overcome which allows for the release of the modified layer from the surface of the substrate. In some examples, the temperature ranges at which chemisorption and desorption occur do not overlap while in others they may partially or fully overlap. Accordingly, in order to remove a molecule from a substrate using chemisorption and desorption, some implementations may maintain the substrate at the same, or substantially same, temperature during the removal and modification operations. In order to remove a molecule from a substrate using chemisorption and desorption that occur in different temperature regimes, the modification operation of block 103 may occur in the first temperature range and the removal operation of block 105 may occur in the second different temperature range which may be higher or lower than the first temperature. Some such embodiments may perform multiple cycles to remove multiple layers of material by maintaining the substrate at the same, or substantially the same, temperature during the removal and modification operations, while other embodiments may repeatedly heat and cool the substrate between the two temperature regimes for chemisorption and desorption.

In some of the embodiments that use different temperature regimes, during or before block 105, the temperature of the substrate may be brought to a second temperature that is different than the first temperature. In some other embodiments, the second temperature is the same, or substantially the same, temperature as the first temperature. This second temperature may be the temperature at which desorption occurs for the one or more modified surface layers. In some embodiments, the second temperature may be greater than the first temperature, and in these embodiments, block 105 may include heating the substrate from the first temperature to the second temperature. In some other embodiments, the second temperature may be less than the first temperature, and in these embodiments, the substrate may be actively cooled from the first temperature to the second temperature. The substrate may be heated using radiant heating, convection heating, solid-to-solid heat transfer, or with a plasma. Additionally, the substrate top, bottom, or both, may be heated. The heating of the substrate may also occur in a non-linear fashion, in some embodiments, as discussed further below. As also described below, the substrate may be actively cooled in various manners.

In block 105, the one or more modified surface layers may be removed while the substrate is maintained at the second temperature. In some embodiments, the second temperature alone may enable and cause desorption of the modified molecules from the substrate thereby removing the modified molecules from the substrate. In some other embodiments, a second process gas with removal molecules may be flowed onto the substrate, including onto the exposed surfaces of the substrate. The second process gas may also include a carrier gas as described above. These removal molecules may react with the modified molecules to form a different volatile molecule, e.g., a volatized molecule. This volatized molecule may in turn be removed from the substrate by desorption when the substrate is at the second temperature.

In some embodiments, the second temperature may be between about 20° C. and 500° C., about 20° C. and 150° C., about 20° C. and 100° C., about 20° C. and 80° C., about 200° C. and 600° C., about 200° C. and 500° C., about 200° C. and 350° C., or about 350° C. and 500° C., for example. Additionally, the substrate may be maintained at the temperature during all, or substantially all (e.g., at least 80%, 90%, or 95%), of the removal operation. The duration of the removal operation may be the duration for which desorption of substantially all (e.g., at least 80%, 90%, or 95%) of desired molecules on the substrate occurs. This may range from about 0.5 seconds to about 10 seconds, about 0.5 seconds to about 5 seconds, about 1 second to about 5, about 0.5 seconds to two minutes, or about 30 seconds to two minutes.

The performance of blocks 103 and 105 may be considered a single ALE cycle. In some implementations, these blocks 103 and 105 may be repeated in order to perform multiple cycles and remove an atomic mono-layer as well as multiple layers of the first material.

In block 107, the surface of the second material is converted to a converted layer, i.e., an etch stop layer, that is capable of withstanding, or configured to withstand, the etching chemistry used to remove the first material. This conversion occurs when the surface of the second material is uncovered or exposed (e.g., via removal of the first material including removal of the modified layer of the first material), and in the presence of conversion molecules of a third process gas that has been, or is being flowed onto, the wafer. This conversion does not occur when the second material is still covered and not exposed to the conversion molecules. In some implementations, the etch front must therefore remove the first material by modification and removal as described above to reach and uncover the surface of the second material before, or when, the conversion of the second material occurs. Although block 107 is depicted after block 105, block 107 may occur concurrently with or after block 105. Additionally, as discussed in more detail below, the third process gas comprising conversion molecules may be flowed onto the substrate in various ways, such as before and/or during the removal operation in block 105. In various embodiments, the conversion molecules are introduced into the chamber in a vapor form or gaseous form and may be optionally accompanied by a carrier gas such as nitrogen, argon, helium, or neon, for instance.

FIG. 2 depicts an example schematic illustration of atomic layer etching in accordance with disclosed embodiments. In diagrams 202a-202e a single layer of material is etched from a wafer. In 202a, the wafer is provided and it has a first material illustrated with shaded circles and having two layers, and a second material, illustrated with white circles, adjacent to and covered by the first material, and having three layers. Molecules of the first material are labeled as 204 and molecules of the second material are labeled as 206, and the top layer of the first material may be considered a surface layer 208 of the first material. In 202b, a first process gas with modifying molecules 210 (the solid black circles, some of which are identified with identifier 210) is introduced to the substrate which modifies the surface layer 208 of the substrate. The schematic in 202b shows that some of the modifying molecules 210 are adsorbed onto the molecules 204 of the surface layer 208 of the substrate thereby creating modified surface layer 212 that includes modified molecules 214 (one modified molecule 214 is identified inside a dotted ellipse in 202b). For some thermal ALE techniques, this diagram 202b may occur while the substrate is maintained at a first temperature as described above, e.g., that enables chemisorption of the modifying molecule on the surface of the first material. In some other implementations, this modification operation may be plasma assisted. Although this Figure illustrates a single layer being modified, in some embodiments, multiple layers of the first material may be modified.

In 202c, after the modified molecules 214 and the modified surface layer 212 have been created in 202b, the first process gas may be optionally purged from the chamber. In 202d, removal molecules 216 are introduced into the process chamber and in some embodiments, this may occur by flowing a second process gas comprising the removal molecules 216, onto the substrate. In some thermal ALE embodiments, this removal operation may be performed at a second temperature where desorption of the modified molecules 214 of the modified surface layer 212 from the substrate occurs; no plasma may be utilized in some of these removal operations. In some embodiments, the second temperature is the same, or substantially the same, as the first temperature. In other embodiments, the first and second temperatures may be different than each other and, in these embodiments, the temperature may be changed from the first temperature to the second temperature by either heating or cooling the substrate. In some other embodiments, the second process gas may be introduced with a plasma or a directional plasma, and ion bombardment may be performed to remove the modified surface of the substrate. During plasma-assisted operations, a bias may be applied to the substrate to attract ions toward it. Although this Figure illustrates a single layer being removed, in some embodiments multiple layers of the first material may be removed if they were previously modified. In 202e, the modified molecules 214, and therefore the modified surface layer 212, have been removed from the substrate and the second layer 218 of the first material remains covering the second material. In the example depicted in 202e, the modifying molecules 210 are not present, but in some embodiments, these modifying molecules 210 may be present as shown, for example, in 202b. In some such embodiments, these modifying molecules 210 may be introduced in subsequent process steps, such as in diagrams 202f and 202g.

Diagrams 202f and 202g illustrate the wafer during and/or after a removal operation, and illustrate an example conversion of the surface of the second material. During the operations of diagrams 202a-202e, the second material remains covered by the first material; the surface of the second material is not exposed in these operations. In diagram 202f, the removal molecules 216 have removed, or etched, some of the first material, i.e., some of the modified layer 218 of the first material, from covering the second material 206, thereby exposing the surface of the second material, i.e., uncovering this surface via removal of the modified layer 218 of the first material. This exposed surface of the second material 206 is illustrated in diagram 202f with three molecules of the second material 206 inside the dotted rectangle 220. With the chemistry used to remove the first layer of material, this second material is vulnerable to etching, including etching at a higher etch rate than the first material, for example. Here in diagram 202f, a third process gas comprising conversion molecules 222 (illustrated as shaded diamonds) has been flowed, or is concurrently flowing with the second process gas, onto the wafer and these conversion molecules 222 convert the exposed surface 220 of the second material into the converted layer of material. In diagram 202g, the three molecules of the exposed surface 220 of the second material have been converted by the conversion molecules 222 into a converted layer 224 of material, as illustrated by these three molecules, or converted molecules, having dark shading. This converted layer 224 is the etch stop layer which is capable of withstanding the etching chemistry.

In diagram 202h, the second layer 218 of the first material has been removed and the depicted surface of the second material has been converted to the converted layer 224 of material, i.e., to converted molecules. In some embodiments, the converted layer of material may be removed, as indicated in diagram 202i. This removal may include two operations, a modification operation involving flowing a fourth process gas having other modifying molecules to modify these converted molecules into a different volatized molecule, and a removal operation involving flowing a fifth process gas having other removal molecules (such as molecules 226 in diagram 202i. Similar to the other process gases, the fourth and fifth process gases may comprise a carrier gas listed above. Additionally, these modification and removal steps of the converted layer 224 may be sequential, overlapping, or simultaneously occurring by using staggered, overlapping, or co-flows of the fourth and fifth process gases.

In some instances, the illustrations in diagrams 202f and 202g may be considered the creation of an "on the fly" etch stop layer. Once the second layer of material is exposed and in the presence of the conversion molecules, the converted layer of material is created "on the fly". This may allow etching of the first material to continue while the exposed underlying second material is protected with the conversion layer, i.e., the etch stop layer.

As noted above, in some embodiments, the conversion of the second layer of material may be through a cation exchange between the second layer of material and the conversion molecules. In some such implementations, the third process gas supplies a cationic constituent in vapor phase that is exchanged with cationic compounds or constituents in the layer of material. The cationic constituents of the second material may be converted to chlorides and thereby volatized as the result of the exchange with the cationic constituent in the third process gas.

For example, the second material may be a zinc oxide, the conversion molecule may be a zirconium compound, and the conversion of the surface of the second material may be a cation exchange of the zinc and zirconium to create a zirconium oxide converted layer of material. In additional examples, conversion reactions at a surface of the second material that comprises zinc may be the following: Example 1, the second material includes ZnO (solid) and the third process gas includes $ZrCl_4$ (gas) which converts the second material to a converted layer of $ZrO_2$ (solid) and $ZnCl_2$ (gas) thereby exchanging and removing the zinc; Example 2, the second material includes $In_2O_3$ (solid) and the third process gas includes $ZrCl_4$ (gas) which converts the second material to a converted layer of $ZrO_2$ (solid) and $InCl_3$ (gas) thereby exchanging and removing the indium; Example 3, the second material includes $Ga_2O_3$ (solid) and the third process gas includes $ZrCl_4$ (gas) which converts the second material to a converted layer of $ZrO_2$ (solid) and $GaCl_3$ (gas) thereby exchanging and removing the gallium.

In these examples, the first material may be $Al_2O_3$ (solid) which can be etched by the primary chemistry, such as HF and trimethylaluminum (TMA). As seen in these examples, the cationic constituents of the second material, the zinc, indium, and gallium, are converted to chlorides that are volatilized and therefore removable.

The techniques provided herein may be applicable to wafers with the first and second materials that have similar properties. This may include, for example, both materials being oxides, high-k oxides, and/or an oxide and a semiconductor oxide that both may be etched by the chemistry used to etch the first material. Some examples may include an aluminum oxide as the first material and a zinc oxide as a second material.

The techniques provided herein create a converted layer of material capable of withstanding, and configured to withstand, the chemistry used to etch the first material by the converted layer of material being, for instance, less reactive to the etching chemistry than the second layer of material and the modified layer. This reactivity may be quantified according to various chemical and physical properties such as etch rates, binding energies, and reactions. In some embodiments, the relationship between the first material, the modified layer of the first material, the second material, and/or the converted layer of material may be quantified with etch rates. For example, the chemistry used to etch the first material may etch the first material, including etching the modified layer, at a first etch rate and may also etch the second material at an unacceptable second etch rate. In some instances, this second etch rate may be greater than or equal to the first etch rate, such as at least 50%, 100%, or 200% greater than or equal to the first etch rate. When exposed to the chemistry for removing the first material, including the modified layer, the converted layer may have an etch rate less than the first etch rate, including less than or equal to 50%, 25%, 15%, 10%, 5%, 2.5%, or 1% of the first etch rate. In one example, the chemistry for etching the first material may etch the second material at a second etch rate about double the first etch rate, and may etch the converted material at a third etch rate that is less than 15% of the first etch rate. In these implementations, the converted layer of material is considered capable of withstanding, and configured to withstand, the chemistry used to etch the first material.

In some embodiments, the relationship between the first material, the modified layer of material, the second material, and/or the converted layer of material may be quantified by reaction byproducts. In some instances, the chemistry used to remove the first material may react with the second material and create byproducts, and these byproducts may remove or otherwise adversely affect the second material. However, the converted layer of material may, in some such implementations, react with the removal chemistry without producing any, or with producing limited amounts of, byproducts. In some implementations, the converted layer of material may not react with, or may have limited reaction with, the removal chemistry. This may prevent, or reduce, the removal of the second material. In some instances, the converted layer of material may also be considered passive with respect to the removal chemistry.

Returning back to the various techniques provided herein, the third process gas for converting the exposed surface of the second material to a converted layer may be flowed onto the substrate in various manners. In some implementations, the third process gas may be flowed during various points and/or aspects of an etching process and/or ALE cycle. This may include flowing the third process gas before the modifying operation, during the modifying operation, after the modifying operation and before the removal operation, during the removal operation, and/or after the removal operation. In some such embodiments, a purge gas may also be flowed into the chamber after flowing the third process gas and before flowing another process gas.

In some implementations, the flow of the third process gas may start during these noted periods and stop during any of the noted periods or operations. This may include starting and stopping the flow one or more times during an etching process or ALE cycle. For example, in a single ALE cycle, the flow of the third process gas may start before the modifying operation and continue flowing until the end of the removal operation. In another example, the flow of the third process gas may start before or at the start of the modifying operation and stop at the end of the modifying operation, and then start again at the start of the removal operation and stop at the end or after the end of the removal operation. In yet another example, the flow of the third process gas may only start after the modifying operation or at the start of the removal operation, continue throughout the entire removal operation, and stop at the end or after the end of the removal operation. In another example, the flow of the third process gas may start during the modifying operation, but after this modifying operation has started, and continue until the end or after the end of the removal operation. In yet another example, the third process gas may be flowed while the first and second process gas are not flowing, such as before the modifying operation, between the modifying and removal operations, and/or after the removal operation.

It should be noted that in some embodiments, the flowing of the third process gas and the converting of the exposed surface of the second material may not occur concurrently. As noted herein, the converting occurs when the surface of the second material is exposed, and the third process gas may be flowed onto the substrate before and/or when this surface becomes exposed during the removal operation. For example, the third process gas may only flow onto the substrate before the removal operation and not during the removal operation, such as during or after the modifying operation, but the third process gas may still be present during the removal operation such that the conversion molecules can react with the surface of the second material when it is uncovered and exposed. This is discussed in more detail below, including with respect to FIGS. 6A-6D.

FIG. 3 depicts another example process flow diagram for performing operations in accordance with disclosed embodiments. In FIG. 3, blocks 301, 303, and 305 are the same as blocks 101, 103, and 105 in FIG. 1, and here the third process gas is co-flowed, or simultaneously flowed, onto the wafer in block 309 during some or all of the modifying operation of block 303. Block 309 may start concurrently with, or after, the start of the modifying operation of block 303; in some embodiments, block 309 may start before the start of the modifying operation of block 303. In block 307, the surface of the second material is converted to the converted layer when it is exposed and in the presence of the third process gas. In some embodiments, the third process gas may be co-flowing during the removal operation of block 305. In some other embodiments, the third process gas is not flowing during the removal operation of block 305, but the third process gas is still present around the wafer such that when the surface of the second material is uncovered and exposed, it is converted to the converted layer. An optional purge may be performed after blocks 303 and/or 309.

Figure 4A:
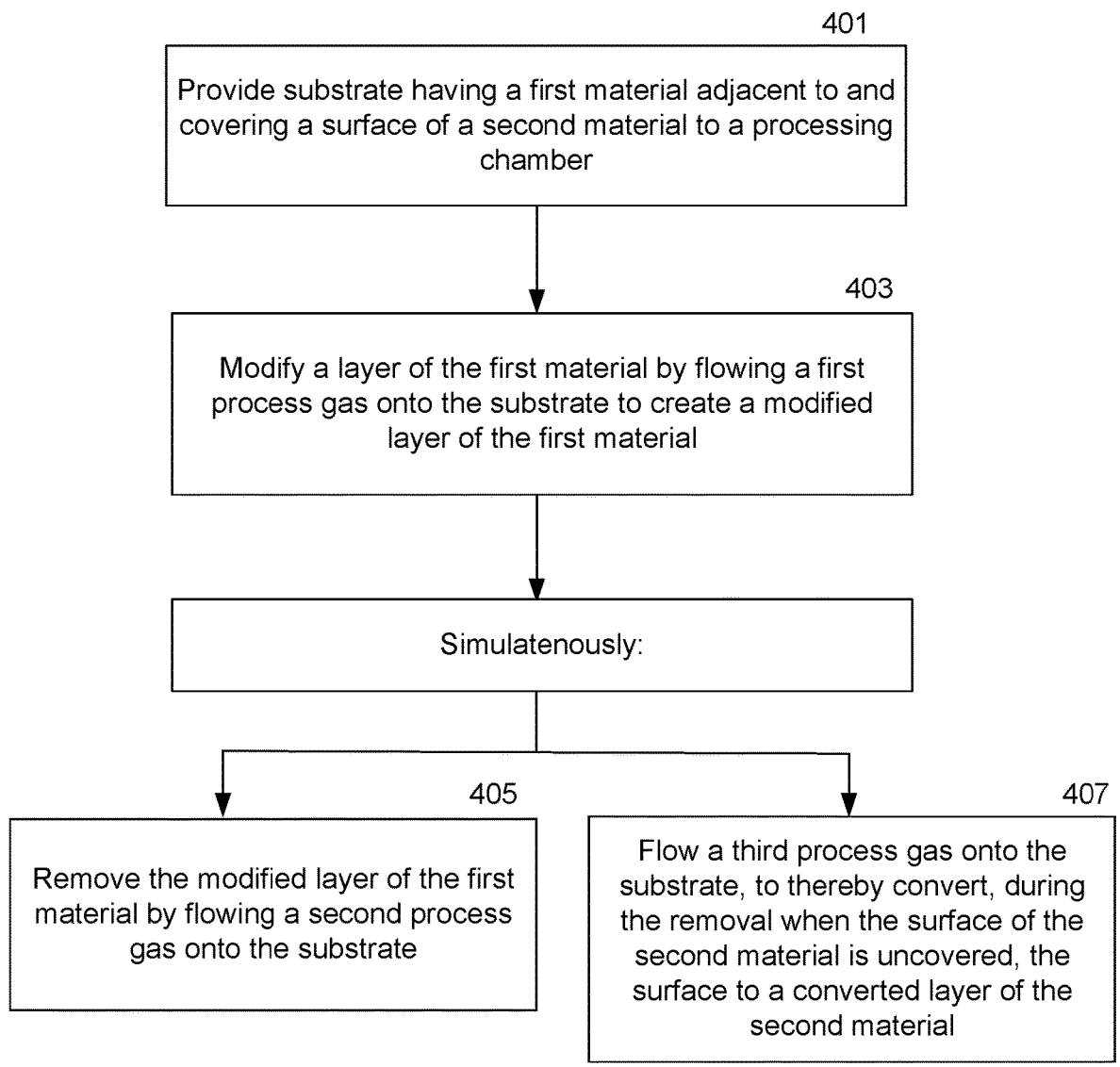
FIG. 4A depicts yet another example process flow diagram for performing operations in accordance with disclosed embodiments.

FIG. 4A depicts yet another example process flow diagram for performing operations in accordance with disclosed embodiments. In FIG. 4A, blocks 401, 403, and 405 are the same as blocks 101, 103, and 105 in FIG. 1, and here the third process gas is co-flowed, or simultaneously flowed, onto the wafer in block 407 during some or all of the removal operation of block 405. Also, in block 407, the surface of the second material is converted to the converted layer when it is exposed and in the presence of the third process gas. In some embodiments, block 407 may start concurrently with, or after, the start of the removal operation of block 405; in some embodiments, block 407 may start before the start of the removal operation of block 405.

Figure 4B:
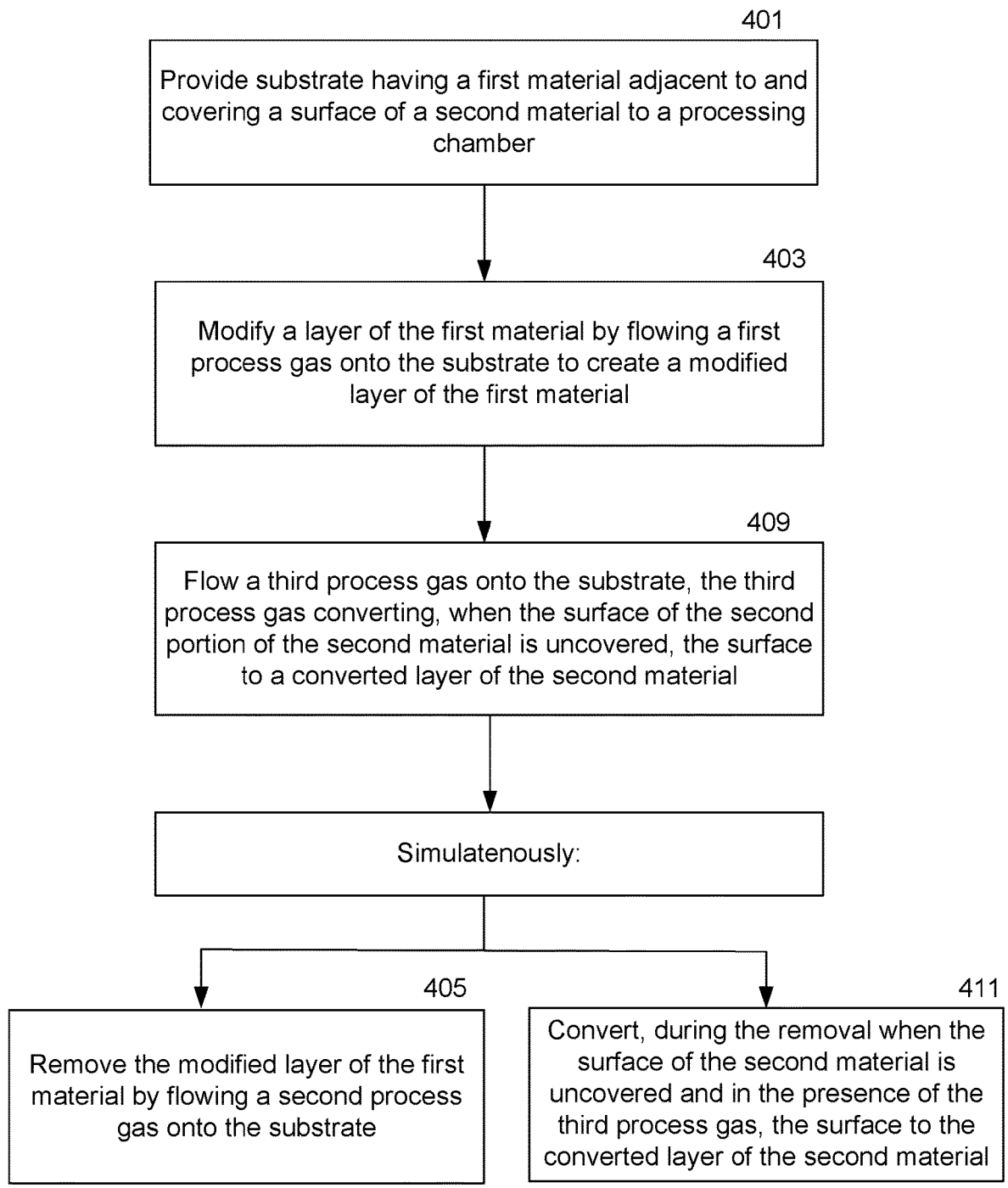
FIG. 4B depicts another example process flow diagram for performing operations in accordance with disclosed embodiments.

FIG. 4B depicts another example process flow diagram for performing operations in accordance with disclosed embodiments. In FIG. 4B, blocks 401, 403, and 405 are the same as in FIG. 4A, and here the third process gas is flowed in between the modification operation of block 403 and the removal operation of block 405 such that, in some embodiments, the third process gas is not flowing onto the substrate during blocks 403 and 405. During the removal operation of block 405, similar to block 307 in FIG. 3, block 411 indicates that the surface of the second material is converted to the converted layer when it is exposed and in the presence of the third process gas. In some embodiments, an optional purge operation may be performed after block 409 and before blocks 405 and 411.

Figure 5:
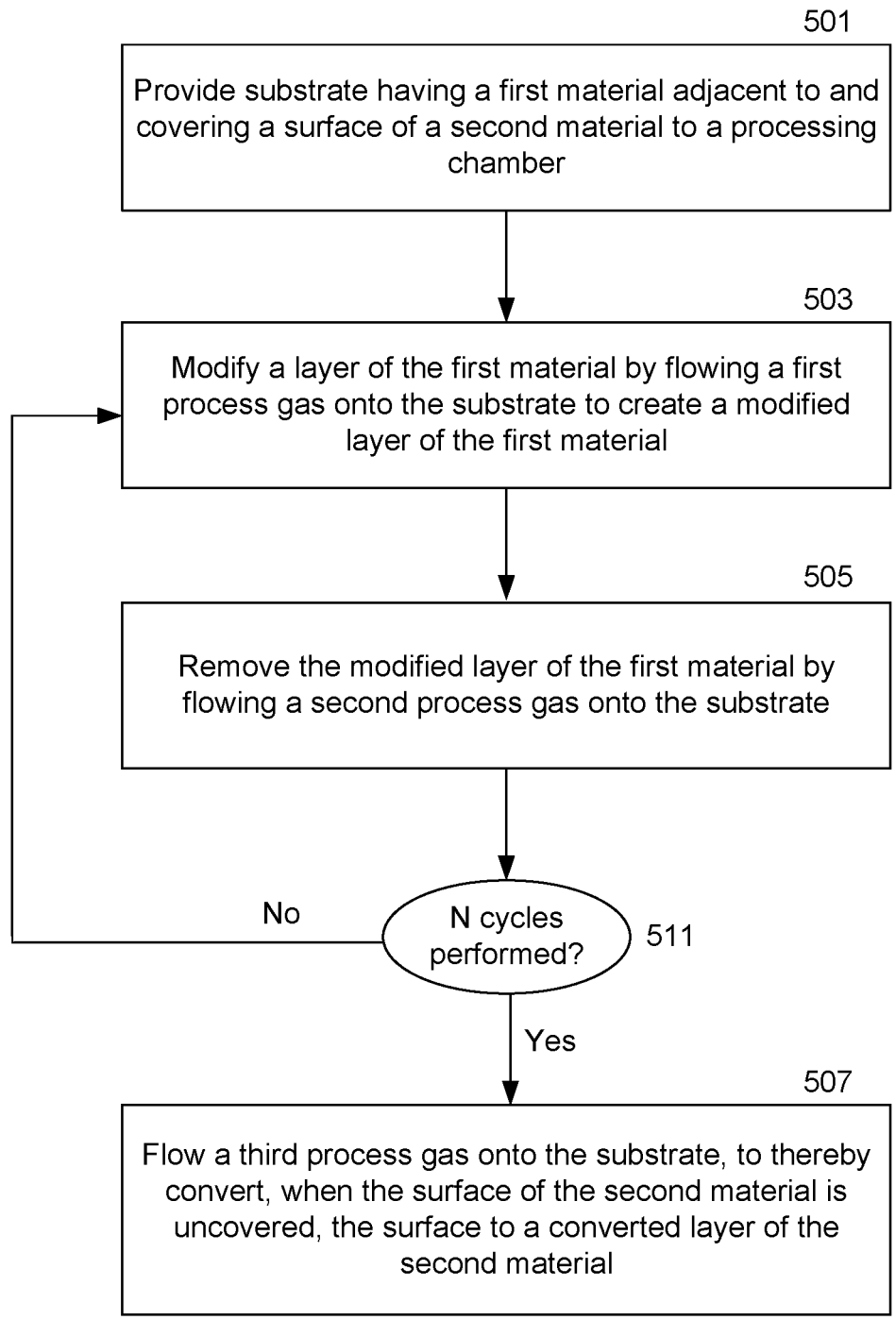
FIG. 5 depicts another example process flow diagram for performing operations in accordance with disclosed embodiments.

Alternatively, or additionally, the third process gas may be flowed during only a part of the total etching performed on a wafer. This may include, for example, flowing the third process gas after performing a number N of ALE cycles on the wafer when the total number of ALE cycles is N+X ALE cycles. This may also include flowing the third process gas after performing a percentage of the ALE cycles, such after performing at least 10%, 50%, 80%, or 95%, of the total ALE cycles for example. FIG. 5 depicts another example process flow diagram for performing operations in accordance with disclosed embodiments. Blocks 501, 503, and 505 of FIG. 5 are the same as in FIG. 1, and here, blocks 503 and 505 are repeated for N ALE, or etching, cycles. Once the decision step 511 determines that the N ALE cycles have been performed, block 507 is performed during which the third process gas is flowed onto the wafer and the surface of the second material is converted to the converted layer when it is exposed and in the presence of the third process gas. This block 507 may be performed for one or more etching cycles after the N cycles are performed. Block 507 may also be performed in any manner described herein, such as flowing the third process gas during the modifying and/or removal operations, or in-between the modifying and removal operations as illustrated in FIG. 4B, for example.

Additional illustrations for flowing the third process gas during some etching operations is shown in FIGS. 6A to 6D which depict schematic illustrations of ALE cycles in accordance with disclosed embodiments. In these FIGS. 6A through 6D, diagrams 602a through 602f depict a wafer during a single ALE cycle. 602a illustrates the wafer before a modifying operation and corresponds with operation 202e in FIG. 2. For example, the shaded circles represent the first layer of material and the white circles represent the second layer of material. 602b illustrates the wafer during a modifying operation, similar to diagram 202b, during which the first process gas comprising a modifying molecule 610 is flowed onto the wafer to form modified molecules 614 and a modified layer 618 of the first material. For some thermal ALE implementations, the modifying of diagram 602b may be performed while the substrate is maintained at a first temperature or first temperature range. 602c illustrates the wafer after the modifying operation of diagram 602b and before the removal operation, and having the modified layer 618.

Diagrams 602d and 602e of FIGS. 6A-6D illustrate the wafer during a removal operation and may correspond with diagrams 202f and 202g of FIG. 2. In diagram 602d, the second process gas comprising the removal molecules 616 is flowed onto the wafer and causes the removal of the modified molecules 614 which uncovers and exposes a surface 620 of the second material. Also, in diagram 602d, the conversion molecules 622 are present around the wafer and as illustrated in diagram 602e, the exposed surface 622 of the second material is converted to the converted layer 624 when in the presence of the conversion molecules 622. In diagram 602f, the modified layer 624 has been removed and the converted layer remains; this may correspond to diagram 202h of FIG. 2. Although not shown here, optional separate modification and removal operations may be performed to remove the converted layer.

In some embodiments, the removal operations of diagrams 602d and 602e of FIGS. 6A-6D may be performed with thermal ALE in which the substrate is maintained at the same, or substantially same, temperature as the modifying operation of diagram 602b. In some other embodiments, these removal operations of diagrams 602d and 602e may be performed while the substrate is maintained a second temperature or second temperature range different than the first temperature or first temperature range of the modifying operation of diagram 602b. Some implementations may include heating or actively cooling the substrate between diagrams 602b and 602d and 602e in order to change the substrates temperature. In some other embodiments, the modification operation of diagram 602b and/or removal operation of diagrams 602d and 602e may be plasma-assisted operations.

Figure 6A:
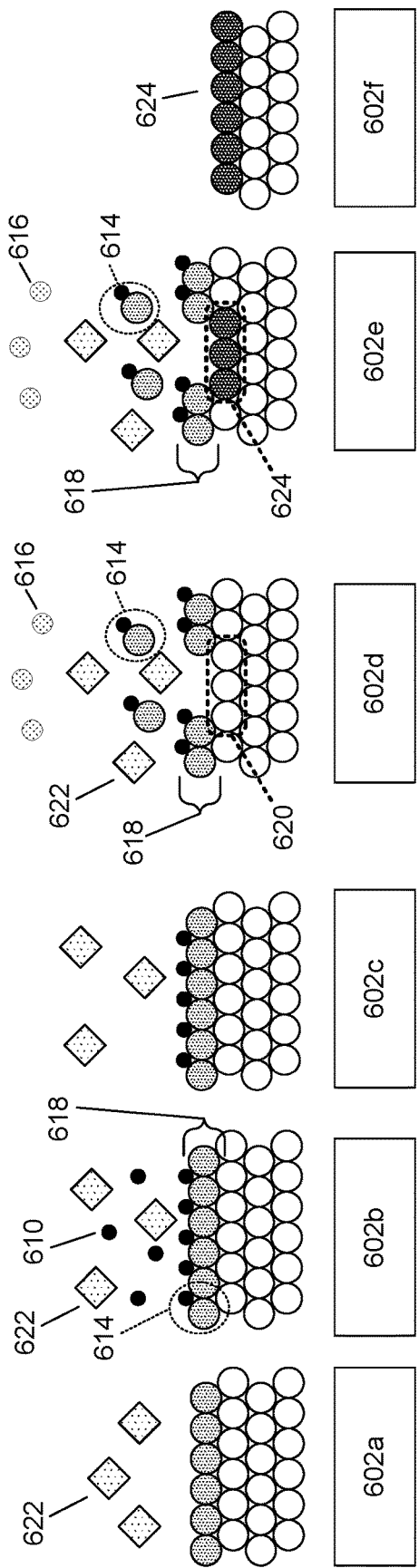

FIGS. 6A-6D further illustrate various flows of the third process gas onto the wafer. In FIG. 6A, the third process gas having the conversion molecules 622 is being flowed onto the wafer in at least diagram 602a before the modifying operation of 602b. As shown, the conversion molecules 622 in FIG. 6A are present during diagrams 602a-602e and, in some embodiments, FIG. 6A may illustrate the third process gas flowing during the whole ALE cycle. In some such embodiments, the third process gas may begin flowing onto the wafer in diagram 602a before the modification operation of 602b and continue flowing onto the wafer after the modifying operation in diagram 602c and during the removal operation of diagrams 602d and 602e. In some embodiments, the third process gas may only flow during diagram 602a (which may be considered flowing while the first and second process gases are not flowing), only during 602a and 602b, or only during 602a, 602b, and 602c, and then stopped, but the third process gas with the conversion molecules nevertheless remains present in diagrams 602a-602e which may be considered the whole ALE cycle. For instance, the third process gas may only flow during diagrams 602a and 602b, and then stopped, but it may remain present during diagrams 602c-602e.

Figure 6B:
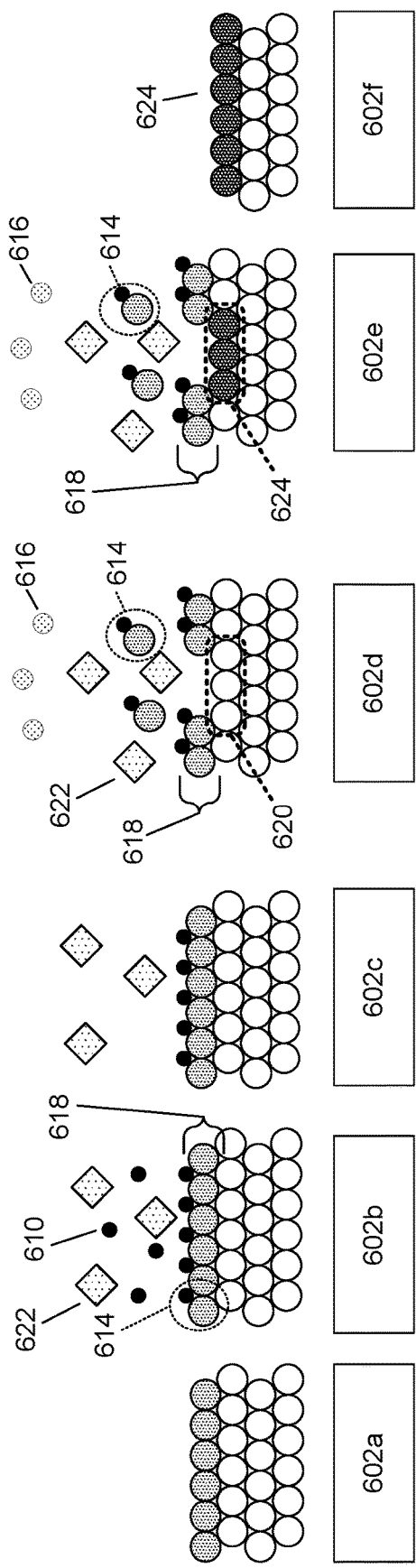

In FIG. 6B, the third process gas having the conversion molecules 622 is flowed onto the substrate during at least a part of the modification operation of diagram 602b. As noted above, the third process gas flow may start concurrently with, or after, the start of the modifying operation. In some embodiments, the third process gas may continue flowing onto the wafer after the modifying operation in diagram 602c and during the removal operation of diagrams 602d and 602e. In some embodiments, the flow of the third process gas may be stopped after the modifying operation and an optional purge may be performed, after which the third process gas may not be flowed after, such as during removal operation of diagrams 602d and 602e, but the third process gas may nevertheless still be present. In some other implementations, the flow of the third process gas may be stopped after the modifying operation and an optional purge may be performed and then the flow of the third process gas may be started before or during the removal operation of diagrams 602d and 602e. As illustrated, the third process gas having the conversion molecules 622 remains present during diagrams 602b-602e even though it may not be flowing during some or all of these diagrams, such as not flowing during 602d and 602e, for example. Some embodiments of this FIG. 6B may correspond with the technique of FIG. 3.

In FIG. 6C, the third process gas having the conversion molecules 622 is flowed onto the substrate after the modification operation of diagram 602b and before the removal operation, as shown with the conversion molecules present in diagram 602c. In some embodiments, the flow of the third process gas may be turned off such that it is not flowing during the removal operations of diagrams 602d and 602e, but is still present during these operations; this may be considered flowing while the first and second process gases are not flowing. Some embodiments of this FIG. 6C may correspond with the technique of FIG. 4B. In some embodiments, the third process gas may continue flowing onto the wafer after the modifying operation in diagram 602c and during the removal operation of diagrams 602d and 602e.

In FIG. 6D, the third process gas is flowed onto the substrate during the removal operation of diagrams 602d and 602e. As noted above, the third process gas flow may start concurrently with, or after, the start of the removal operation. Some embodiments of this FIG. 6D may correspond with the technique of FIG. 4A.

Depending on the chemistries involved in the ALE operations, it may be advantageous to flow the third process gas at various times, including those illustrated in FIGS. 6A-6D. For example, the third process gas may be incompatible with, or have an undesired reaction with, the first process gas and/or the first layer of material. It may therefore be advantageous to prevent or reduce these unwanted effects by only flowing the third process gas after the modification operation and/or during the removal operations illustrated in FIGS. 6C and 6D, for instance. In some other embodiments, there may be limited to no undesirable effects with flowing the third processing gas during the ALE cycle and it may therefore be flowed during the whole ALE cycle as illustrated in FIG. 6A, for example.

In some embodiments, the flow rate of the third process gas may remain constant. In some other embodiments, it may be advantageous to vary the third process gas flow rate. This may include, for instance, increasing the third process gas flowrate during the removal operation in order to provide more conversion molecules as the removal operation progresses. Some example flow rates may include between about 50 sccm and 1000 sccm.

In some implementations, the conversion of the second layer of material to an etch stop layer may be considered selectively converting, when the surface of the second material is uncovered via removal of the modified layer, the surface of the second material to a layer of etch stop material, in which the layer of etch stop material is only positioned on top of the second material. In some such implementations, during the removing, the modified layer of the first material and the layer of etch stop material may be exposed to the second process gas and the second process gas may be less reactive with the layer of etch stop material than with the modified layer of the first material and the second material.

In some embodiments, instead of converting a layer of the second material to a converted layer, a selective deposition may be performed to deposit an etch stop layer onto the second material. This deposition may, in some instances, be performed after, or concurrently with, a removal operation. In some embodiments, this selective deposition of a layer of etch stop material may occur when the surface of the second portion of the second material is uncovered. This selectivity may also include depositing this layer of etch stop material on the second, uncovered material, while limited to no depositing of this layer of etch stop material occurs on the target, first material. In some embodiments, this may include selectively converting, when the surface of the second material is uncovered via removal of the modified layer, the surface of the second material to a layer of etch stop material, in which the layer of etch stop material is only positioned on top of the second material, such that during the removing, the modified layer of the first material and the layer of etch stop material are exposed to the second process gas and the second process gas is less reactive with the layer of etch stop material than with the modified layer of the first material and the second material.

This deposited etch stop layer may have the same characteristics and properties of the converted layer described above. This includes the deposited etch stop layer being capable of withstanding, and configured to withstand, the chemistry used to etch the first material. This may further include having an etch rate less than the first etch rate (i.e., the etch rate at which the chemistry removes the first material which includes the modified layer), including less than or equal to 50%, 25%, 15%, 10%, 5%, 2.5%, or 1% of the first etch rate, a binding energy greater than the binding energy of the modified layer and/or greater than or equal to the binding energy of the chemical species used for the removal, and/or reacting with the removal chemistry without producing any, or with producing limited amounts of, byproducts.

The selective deposition may occur in the same or a different chamber. This selective deposition may be accomplished using various deposition processes, such as a chemical vapor deposition (CVD) or atomic layer deposition (ALD). Some CVD processes may deposit a film on a wafer surface by flowing one or more gas reactants into a reactor which form film precursors and by-products. The precursors are transported to the wafer surface where they are adsorbed by the wafer, diffused into the wafer, and deposited on the wafer by chemical reactions, including by the generation of a plasma in PECVD.

In a typical PECVD reaction, a substrate is heated to an operating temperature and exposed to one or more volatile precursors which react and/or decompose to produce the desired deposit on the substrate surface. The PECVD process generally begins by flowing one or more reactants into the reaction chamber. The reactant delivery may continue as a plasma is generated which exposes the substrate surface to the plasma, which in turn causes deposition to occur on the substrate surface. This process continues until a desired film thickness is reached, after which the plasma is generally extinguished and the reactant flow is terminated. Next, the reaction chamber may be purged and post-deposition steps may be performed.

Some other deposition processes involve multiple film deposition cycles, each producing a "discrete" film thickness. ALD is one such film deposition method, but any technique which puts down thin layers of film and used in a repeating sequential matter may be viewed as involving multiple cycles of deposition. ALD is a film forming technique which is well-suited to the deposition of conformal films due to the fact that a single cycle of ALD only deposits a single thin layer of material, the thickness being limited by the amount of one or more film precursor reactants which may adsorb onto the substrate surface (i.e., forming an adsorption-limited layer) prior to the film-forming chemical reaction itself. Multiple "ALD cycles" may then be used to build up a film of the desired thickness, and since each layer is thin and conformal, the resulting film substantially conforms to the shape of the underlying devices structure. In certain embodiments, each ALD cycle includes the following steps: (1) Exposure of the substrate surface to a first precursor, (2) purge of the reaction chamber in which the substrate is located, (3) activation of a reaction of the substrate surface, typically with a plasma and/or a second precursor, and (4) purge of the reaction chamber in which the substrate is located. The duration of each ALD cycle may typically be less than 25 seconds or less than 10 seconds or less than 5 seconds. The plasma exposure step (or steps) of the ALD cycle may be of a short duration, such as a duration of 1 second or less, for example. The plasma may be of other durations longer than that 1 second, such as 2 seconds, 5 seconds, or 10 seconds, for instance Applications The techniques and apparatuses provided herein may be used for various chemistries. In one example, the first material may be aluminum oxide and the second material may be a zinc oxide. The aluminum oxide may be etched using a processing gas comprising the removal molecule trimethylaluminum (TMA) and this TMA may also remove the underlying zinc oxide. In order to prevent this zinc oxide removal by the TMA, the third process gas comprising a zirconium conversion molecule may be flowed onto the wafer to convert a layer of the zinc oxide into a converted layer of zirconium oxide which does not react with TMA. In some embodiments, the zirconium conversion molecule may include zirconium tetrachloride. In some embodiments, this converted layer of zirconium oxide may be removed by flowing a fourth process gas onto the wafer that comprises dimethylaluminum chloride (DMAC). In some instances, this removal of the converted layer, or etch stop layer, may also include flowing hydrogen fluoride (HF) as a modifying operation followed by flowing DMAC in the removal operation.

As also noted above, another example may include aluminum oxide covering the second material that is indium gallium zinc oxide (IGZO). To etch this aluminum oxide, a first process gas containing hydrogen fluoride (HF) may be used for the modifying operation, and the removal molecule may include TMA which again may remove the underlying IGZO. The third process gas therefore may include zirconium, such as a zirconium chloride, e.g., $ZrCl_4$ or $ZrCl_4$, or Tetrakis(ethylmethylamino)zirconium(IV) (TEMAZ), to convert the surface of the exposed IGZO to a zirconium oxide, such as $ZrO_2$ (solid) or $ZrO_2$. During this example and the above example, etching of the aluminum oxide layer may continue during the conversion reactions.

ALE Apparatuses

Figure 7:
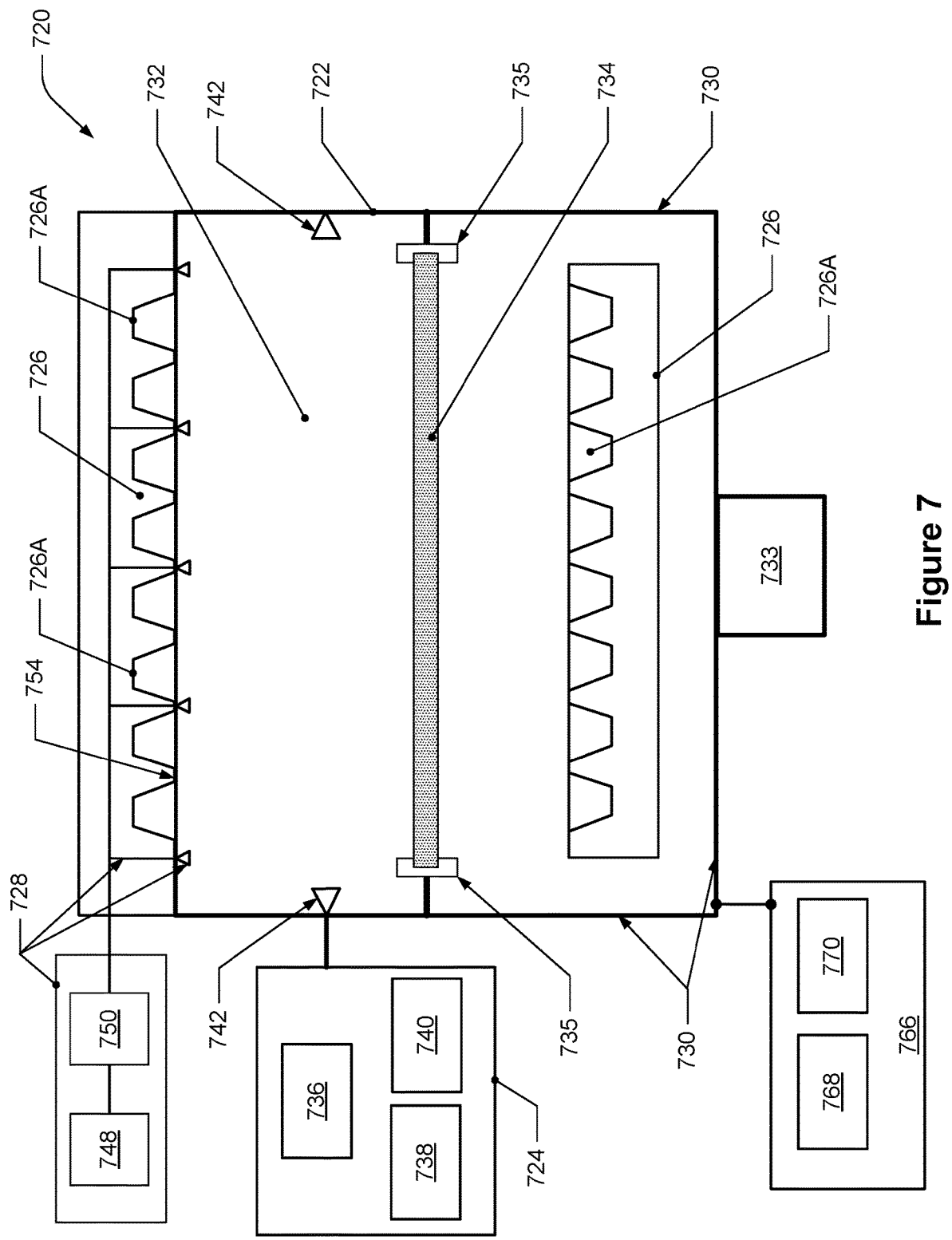
FIG. 7 depicts an example apparatus for semiconductor processing in accordance with disclosed embodiments, including thermal atomic layer etching.

Referring now to FIG. 7, an example of a substrate processing chamber 720 for selectively etching materials according to the present disclosure is shown. While a specific substrate processing chamber is shown and described, the methods described herein may be implemented on other types of substrate processing systems. FIG. 7 depicts an example apparatus 720 for semiconductor processing in accordance with disclosed embodiments, including thermal atomic layer etching; this apparatus 720 includes a processing chamber 722, a process gas unit 724, a substrate heating unit 726, and a substrate cooling unit 728. The processing chamber 722 has chamber walls 730 that at least partially bound and define a chamber interior 732 (which may be considered a plenum volume). The process gas unit 724 is configured to flow process gases, which may include liquids and/or gases, such as a reactant, modifying molecules, converting molecules, or removal molecules, onto a substrate 734 in the chamber interior 732. The process gas unit 724 also includes one or more flow features 742 configured to flow the first process gas onto the substrate 734, such as a hole, a nozzle (two of which are depicted), or a showerhead. The one or more flow features 742 may be positioned above, below, on the side, or a combination of positions, within the chamber interior 732, such as on the processing chamber walls, top, and bottom, for instance. The process gas unit 724 may include a mixing vessel for blending and/or conditioning process gases for delivery to the chamber interior 732. One or more mixing vessel inlet valves may control introduction of process gases to the mixing vessel.

The process gas unit 724 may include a first process gas source 736, a first process liquid source 738, a vaporization point (not depicted) which may vaporize the first liquid into a gas, and a carrier gas source 740. Some reactants may be stored in liquid form prior to vaporization and subsequent to delivery to the process chamber 722. The first process gas may comprise an oxidizing gas, a halogenating gas, or another gas configured to modify one or more layers of material on the substrate, without using a plasma, in some embodiments. In some implementations, the vaporization point may be a heated liquid injection module. In some other implementations, the vaporization point may be a heated vaporizer. In yet other implementations, the vaporization point may be eliminated from the process station. In some implementations, a liquid flow controller (LFC) upstream of the vaporization point may be provided for controlling a mass flow of liquid for vaporization and delivery to the chamber interior 732. The carrier gas source 740 includes one or more carrier gases or liquids that may be flowed with the processing gas; these may be inert gases like $N_2$, Ar, Ne, He. The apparatus 720 may also include a vacuum pump 733 configured to pump the chamber interior to low pressures, such as a vacuum having a pressure of 1 mTorr or 10 Torr, for example.

The chamber interior 732 includes substrate support features 735 that are configured to support and thermally float a substrate 734 in the chamber. The substrate support features 735 may include clamps, horizontal pins or supports, vertical pins or supports, and semi-circular rings, for instance, that support the substrate 734 in the chamber interior 732. These features are configured to support the substrate 734 such that the thermal mass of the substrate 734 is reduced as much as possible to the thermal mass of just the substrate. Each substrate support feature 735 may therefore have minimal contact with the substrate 734 and may be the smallest number of features required to adequately support the substrate during processing (e.g., in order to support the weight of the substrate and prevent inelastic deformation of the substrate). For instance, the surface area of one substrate support feature 735 in contact with a substrate may be less than about 1%, 0.5%, 0.1%, 0.05%, or 0.01% of the overall surface area of the back side of the substrate; also, for instance, 2, 3, or 4 features may be utilized.

In one example, the support features 735 may include two or more vertical pins that have grooves wrapped or spiraled along the vertical, longitudinal axis and that are offset at varying distances from the longitudinal axis and configured to support a substrate. When the vertical pin rotates along its longitudinal axis and the edge of a substrate is positioned in the groove, the edge of the groove, and therefore the edge of the substrate, moves farther away from the longitudinal axis. When multiple vertical pins are used to support a substrate, the rotation of the vertical pins causes the grooves to apply a supporting force to the substrate in a direction perpendicular to the longitudinal axis.

In some embodiments, the chamber 722 may include a wafer support pedestal that includes substrate lift pins. During thermal ALE processing, the lift pins may support and position the substrate away from the pedestal such that there is substantially no transference of thermal energy between the pedestal and substrate (e.g., less than 10%, 5%, 1%, 0.5%, or 0.1% of energy transferred between the two). In some other embodiments, the chamber 722 may not have a pedestal. In some embodiments, an electrostatic chuck (ESC) may be used that contains substrate heating unit 726 configured to heat the substrate to temperatures provided herein, such as between about 20° C. and 500° C.

The substrate heating unit 726 is configured to heat the substrate to multiple temperatures and maintain such temperatures for at least 1 second, 5 seconds, 10 seconds, 30 seconds, 1 minute, 2 minutes, or 3 minutes, for example. In some embodiments, the substrate heating unit 726 is configured to heat the substrate between at least two temperature ranges, with the first range between about 20° C. and 150° C., and the second range between about 200° C. and 600° C., as well as configured to maintain the substrate at a temperature within these ranges for at least 1 second, 5 seconds, or 10 seconds, for example. Additionally, in some embodiments, the substrate heating unit 726 is configured to heat the substrate from the first temperature range to the second temperature range in less than about 250 milliseconds, 150 milliseconds, 100 milliseconds, or 50 milliseconds, for instance.

The substrate heating unit 726 may utilize radiant heating, convective heating, laser heating, plasma heating, solid-to-solid thermal transference, or a combination of these items. For radiant heating, the substrate heating unit 726 may be used for emitted light heating, infrared heating, ultraviolet heating, microwave heating, radio frequency heating, and induction heating. For example, the substrate heating unit 726 may include light emitting diodes (LEDs) that emit visible light with wavelengths that may include and range between 400 nanometers (nm) and 800 nm. In another example, the infrared heating may use one or more infrared emitters that emit infrared radiation in the 780 nanometer (nm) to 1400 nm range (e.g., a near infrared heater), in the 1400 nm and 3000 nm range (e.g., a medium infrared heater), and 3000 nm or above (e.g., a far infrared heater), for instance. This may also include, for instance, a heat lamp, light emitting diodes (e.g., LEDs), a ceramic heater, a quartz heater, or a plurality of Gradient Index (GRIN) Lenses connected to a light energy source. A GRIN lens is configured to deliver heat energy (thermal or light) from the light energy source to the substrate in a uniform manner; the light source may be a laser or high-intensity light source that transmits the heat energy through a conduit, such as a fiber optic cable, to the GRIN lenses. The heating elements utilized by the substrate heating unit 726 may be positioned above, below, on the side, or a combination of the positions, the substrate 734, and they may be positioned inside, outside, or both, the chamber interior 732. In FIG. 7, the heating elements utilized by the substrate heating unit 726 include a plurality of LEDs 726A that are positioned both above and below the substrate 734; the lower heating elements are positioned inside the chamber interior 732 and the upper heating elements are positioned outside the chamber interior 732. In some embodiments, for some of the heating elements that are positioned outside the chamber 722, the chamber 722 may have a window 754 that allows for the radiation to be transmitted into the chamber interior 732 and onto the substrate 734. In some embodiments, this window 754 may be an optical-grade quartz plate while in other embodiments it may be a transparent indium tin oxide (ITO) window. In some embodiments, the substrate heating unit 726 include a plurality of LEDs 726A may only be positioned underneath the substrate 734, which may include inside a pedestal or ESC that also may include a window through which the light emitted by the LEDs may reach the backside of the substrate.

For convective heating, the substrate heating unit 726 may flow a heating gas into the chamber interior 732 in order to heat the substrate. The substrate heating unit 726 may include a heating gas source, a heating unit configured to heat the heating gas to a desired temperature, such as at least 20° C., 100° C., 250° C., 350° C., 500° C., and 600° C., and heating flow features, such as nozzles or holes, that allow for the heating gas to flow into the chamber interior 732 and onto the substrate 734. These heating flow features may be positioned above, below, on the side of, or a combination, the substrate.

For laser heating, the substrate heating unit 726 may have one or more lasers that are configured to heat the substrate in the chamber interior. These lasers may be stationary or configured to move (e.g., a scanning laser), and they may be positioned above, below, or both, the substrate; the lasers may also be positioned inside, outside, or both, of the chamber interior. Similar to the radiant heating discussed above, for lasers that are positioned outside the chamber interior, the chamber may include a window that enables the light emissions of the laser to reach the substrate.

For plasma heating, the substrate heating unit 726 may have features configured to generate and maintain a plasma in the chamber interior to heat the substrate. Features that may generate a plasma are discussed in more detail below. In addition, in some embodiments, the chamber interior may include vertical pins that are positioned below the substrate and configured to support the wafer. During heating of the substrate, it may be supported by only the vertical pins and a plasma may be generated between the bottom of the substrate and a surface below the substrate, such as the bottom wall of the chamber or a wafer support pedestal. This plasma may heat and maintain the temperature of the substrate to the desired temperatures.

For solid-to-solid thermal transference, the substrate heating unit 726 may have one or more heating surfaces that are configured to contact and heat the substrate in the chamber interior. In some embodiments, the substrate heating unit 726 may have a heating platen, such as a flat surface or a surface of a substrate pedestal, that is configured to contact the back surface of the substrate and heat the substrate. This heating platen may have heating elements such as a heating coil, heating fluid, or radiative heating discussed above, that may heat the surface of the heating platen. The substrate may be heated when the back of the substrate is in direct contact with, or is offset from the heating platen but close enough to receive thermal energy from, the heating platen. When using this solid-to-solid thermal transference to heat the substrate, the substrate is separated from the heating platen when it is cooled. While some conventional ALE apparatuses may have a substrate pedestal that includes both heating and cooling elements, these apparatuses are unable to quickly (e.g., under 250 milliseconds) cycle between the temperatures of thermal ALE because of the large thermal masses of the pedestal that are repeatedly heated and cooled. For instance, it may take multiple seconds or minutes to heat a pedestal from a first temperature range (e.g., 20° C. to 100° C.) to a second temperature range (e.g., 200° C. to 500° C.), as well as to cool the pedestal from the second temperature range to a lower temperature that can cool the substrate to the first temperature range. Accordingly, after using this solid-to-solid heating technique, the heating platen and the substrate are separated from each other which may be accomplished, for instance, by moving the substrate and/or the heating platen away from each other. Without this separation, cooling occurs of both the thermal mass of the substrate and the heating platen which increases the cooling time which decreases substrate throughput. In some embodiments, an ESC or pedestal having the substrate heating unit and a Peltier element for cooling may enable fast heating and cooling times (such as about 30 seconds to cool a substrate to a desired temperature).

The substrate cooling unit 728 of FIG. 7 is configured to actively cool the substrate. In some embodiments, the substrate cooling unit 728 flows a cooling gas onto the substrate 734 which actively cools the substrate 734. The substrate cooling unit 728 may include a cooling fluid source 748 which may contain a cooling fluid (a gas or a liquid), and a cooler 750 configured to cool the cooling fluid to a desired temperature, such as less than or equal to 0° C., −50° C., −100° C., −150° C., −170° C., −200° C., and −250° C., for instance. The substrate cooling unit 728 includes piping and coolant flow features 752, e.g., nozzles or holes, that are configured to flow the coolant fluid into the chamber interior 732. In some embodiments, the fluid may be in liquid state when it is flowed to the chamber 722 and may turn to a vapor state when it reaches the chamber interior 732, for example if the chamber interior 732 is at a low pressure state, such as 1 Torr, for instance. The cooling fluid may be an inert element, such as nitrogen, argon, helium. In some embodiments, the flow rate of the cooling fluid into the chamber interior 732 may be at least 10 liters per second, 50 liters per second, 100 liters per second, 150 liters per second, 200 liters per second, 250 liters per second, and 300 liters per second, for example.

Various factors may increase the ability of the cooling fluid to cool the substrate. It has been discovered through various experiments that the higher the flow rate of the cooling fluid, the faster the substrate is cooled. In one example experiment, a cooling gas at about −196° C. flowed onto a substrate at a flow rate of 1 liter per second was found to reduce the temperature of a substrate from about 220° C. to about 215° C. in about 5,000 milliseconds, while the same cooling gas a flow rate of 10 liters per second reduced the temperature of a substrate from about 220° C. to about 195° C. in about 5,000 milliseconds. It was also discovered that a gap (1052 in FIG. 10) between the substrate and the top of the chamber may also affect the cooling of the substrate; the smaller the gap, the higher the cooling. In one instance, it was discovered that a substrate separated from the top of the chamber by a gap of about 50 micrometers was cooled from about 220° C. to about 215° C. in about 5,000 milliseconds using a cooling gas at about −196° C., while a substrate separated from the top of the chamber by a gap of about 5 millimeters was cooled from about 220° C. to about 20TC in about 5,000 milliseconds using the same cooling gas. Accordingly, it was discovered that the higher the flow rate and the smaller the gap, the faster the substrate is cooled.

In some embodiments, the substrate cooling unit 728 may use solid-to-solid thermal transference to actively cool the substrate 734. In some of these embodiments, a cooling platen, such as a flat, cooled surface may be used to contact the bottom of the substrate and cool the substrate. This platen may be cooled by flowing a cooling fluid on, through, or underneath the platen. When using this solid-to-solid cooling, similar to the solid-to-solid heating discussed above, the substrate is separated from the cooling platen during heating of the substrate, such as by moving the substrate away from the cooling platen by, for instance, raising it up with lift pins. Without this separation, both the thermal masses of the substrate and cooling platen are cooled which requires more cooling that in turn increases process time and decreases throughput. In some embodiments, radiant heating of the top of the substrate or plasma heating of the bottom of the substrate may be used in conjunction with solid-to-solid cooling.

In some embodiments, the substrate cooling unit 728 may use laser cooling to cool the substrate. This may enable the cooling of a substrate that includes thulium molecules on at least the exposed surface of the substrate by utilizing a reverse Navier-Stokes reaction. For example, the temperature of the substrate manifests itself in phonons and the laser cooling emits photons to the substrate surface which interact with and pick-up phonons in the thulium, and then leave the substrate with the phonon from the thulium at a higher energy level. The removal of these phonons causes a decrease in the temperature of the substrate. The thulium may be doped onto the surface of the substrate in order to enable this laser cooling, and this doping may be incorporated into the techniques listed above, such as occurring after or before any operation, such as the removal operation.

As noted above, some embodiments of the apparatus may include a plasma source configured to generate a plasma within the chamber interior. These plasma sources may be a capacitively coupled plasma (CCP), an inductively coupled plasma (ICP), an upper remote plasma, and a lower remote plasma.

In some embodiments, the apparatuses described herein may include a controller that is configured to control various aspects of the apparatus in order to perform the techniques described herein. For example, in FIG. 7, apparatus 720 includes a controller 766 (which may include one or more physical or logical controllers) that is communicatively connected with and that controls some or all of the operations of a processing chamber. The system controller 766 may include one or more memory devices 768 and one or more processors 770. In some embodiments, the apparatus includes a switching system for controlling flow rates and durations, the substrate heating unit, the substrate cooling unit, the loading and unloading of a substrate in the chamber, the thermal floating of the substrate, and the process gas unit, for instance, when disclosed embodiments are performed. In some embodiments, the apparatus may have a switching time of up to about 500 ms, or up to about 750 ms. Switching time may depend on the flow chemistry, recipe chosen, reactor architecture, and other factors.

In some implementations, the controller 766 is part of an apparatus or a system, which may be part of the above-described examples. Such systems or apparatuses can include semiconductor processing equipment, including a processing tool or tools, chamber or chambers, a platform or platforms for processing, and/or specific processing components (a gas flow system, a substrate heating unit, a substrate cooling unit, etc.). These systems may be integrated with electronics for controlling their operation before, during, and after processing of a semiconductor wafer or substrate. The electronics may be referred to as the "controller," which may control various components or subparts of the system or systems. The controller 766, depending on the processing parameters and/or the type of system, may be programmed to control any of the processes disclosed herein, including the delivery of processing gases, temperature settings (e.g., heating and/or cooling), pressure settings, vacuum settings, power settings, radio frequency (RF) generator settings, RF matching circuit settings, frequency settings, flow rate settings, fluid delivery settings, positional and operation settings, wafer transfers into and out of a tool and other transfer tools and/or load locks connected to or interfaced with a specific system.

Broadly speaking, the controller 766 may be defined as electronics having various integrated circuits, logic, memory, and/or software that receive instructions, issue instructions, control operation, enable cleaning operations, enable endpoint measurements, and the like. The integrated circuits may include chips in the form of firmware that store program instructions, digital signal processors (DSPs), chips defined as application specific integrated circuits (ASICs), and/or one or more microprocessors, or microcontrollers that execute program instructions (e.g., software). Program instructions may be instructions communicated to the controller in the form of various individual settings (or program files), defining operational parameters for carrying out a particular process on or for a semiconductor wafer or to a system. The operational parameters may, in some embodiments, be part of a recipe defined by process engineers to accomplish one or more processing operations during the fabrication of one or more layers, materials, metals, oxides, silicon, silicon dioxide, surfaces, circuits, and/or dies of a wafer.

The controller 766, in some implementations, may be a part of or coupled to a computer that is integrated with, coupled to the system, otherwise networked to the system, or a combination thereof. For example, the controller may be in the "cloud" or all or a part of a fab host computer system, which can allow for remote access of the wafer processing. The computer may enable remote access to the system to monitor current progress of fabrication operations, examine a history of past fabrication operations, examine trends or performance metrics from a plurality of fabrication operations, to change parameters of current processing, to set processing operations to follow a current processing, or to start a new process. In some examples, a remote computer (e.g. a server) can provide process recipes to a system over a network, which may include a local network or the Internet. The remote computer may include a user interface that enables entry or programming of parameters and/or settings, which are then communicated to the system from the remote computer. In some examples, the controller 766 receives instructions in the form of data, which specify parameters for each of the processing operations to be performed during one or more operations. It should be understood that the parameters may be specific to the type of process to be performed and the type of tool that the controller is configured to interface with or control. Thus as described above, the controller 766 may be distributed, such as by comprising one or more discrete controllers that are networked together and working towards a common purpose, such as the processes and controls described herein. An example of a distributed controller for such purposes would be one or more integrated circuits on a chamber in communication with one or more integrated circuits located remotely (such as at the platform level or as part of a remote computer) that combine to control a process on the chamber.

As noted above, depending on the process operation or operations to be performed by the apparatus, the controller 766 might communicate with one or more of other apparatus circuits or modules, other tool components, cluster tools, other tool interfaces, adjacent tools, neighboring tools, tools located throughout a factory, a main computer, another controller, or tools used in material transport that bring containers of wafers to and from tool locations and/or load ports in a semiconductor manufacturing factory.

As also stated above, the controller is configured to perform any technique described above. For instance, referring to apparatus 720 of FIG. 7 and technique of FIG. 1, in some embodiments the controller 766 is configured to cause the substrate heating unit 726 to bring (i.e., heat or actively cool) the substrate 734 positioned on the substrate support features 735 to a first temperature, and cause the process gas unit 724 to flow the first process gas to the substrate 734. As noted above, the first process gas is configured to modify one or more surface layers of material on the substrate 734 by chemical adsorption, without using a plasma in some embodiments, while the substrate is maintained at the first temperature. The controller 766 may further be configured to cause, after the modifying, the substrate heating unit 726 to maintain the substrate 734 at the second temperature and the one or more modified surface layers on the substrate 734 may be removed by desorption while the substrate 734 is maintained at the second temperature. The controller 766 may further be configured to cause the process gas unit 724 to flow the third process gas onto the substrate as described herein to convert the exposed surface of the second material into the converted layer of material, i.e., the etch stop layer.

Figure 8A:
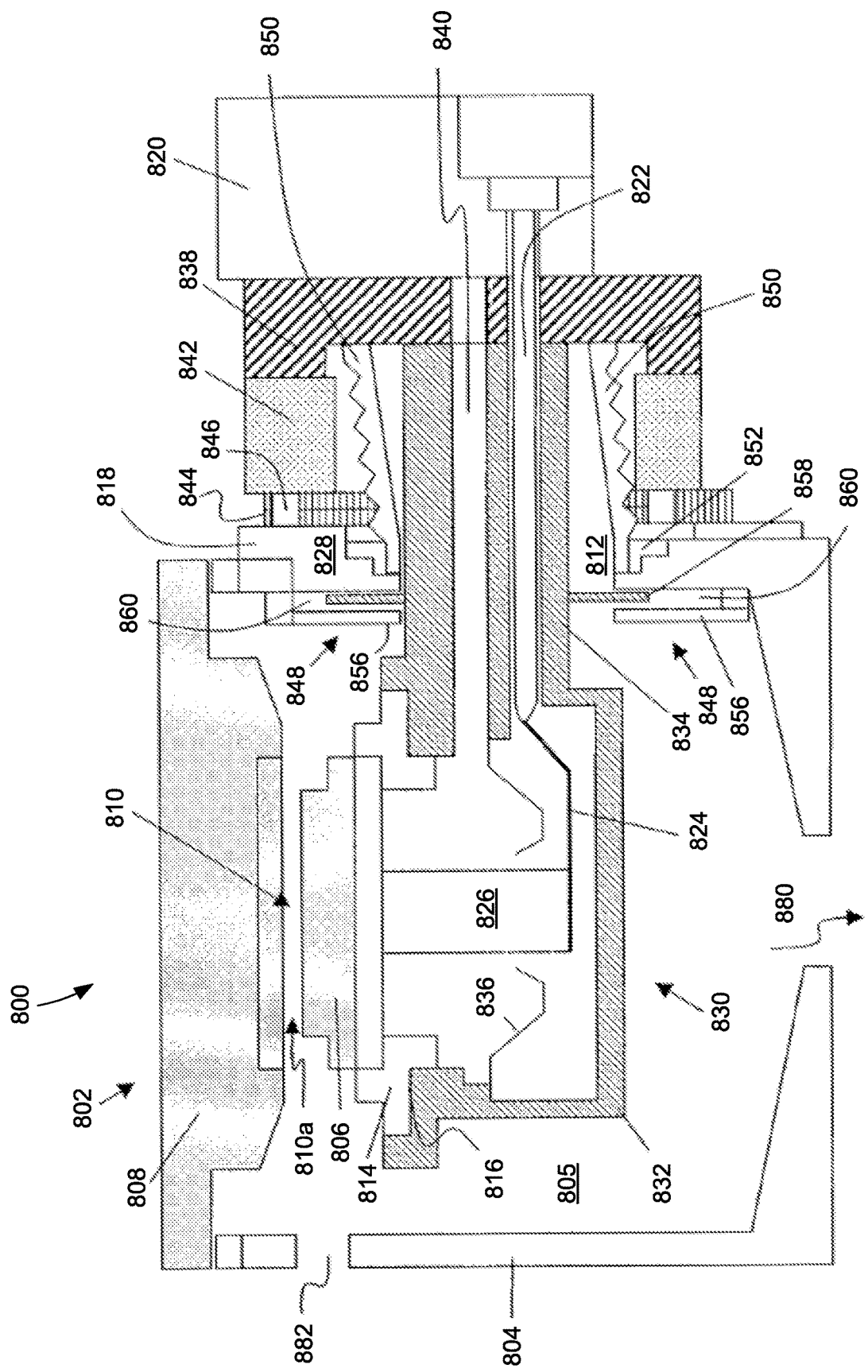
FIGS. 8A-8C illustrate an embodiment of an adjustable gap capacitively coupled confined RF plasma reactor that may be used for performing the etching operations described herein.
Figure 8B:
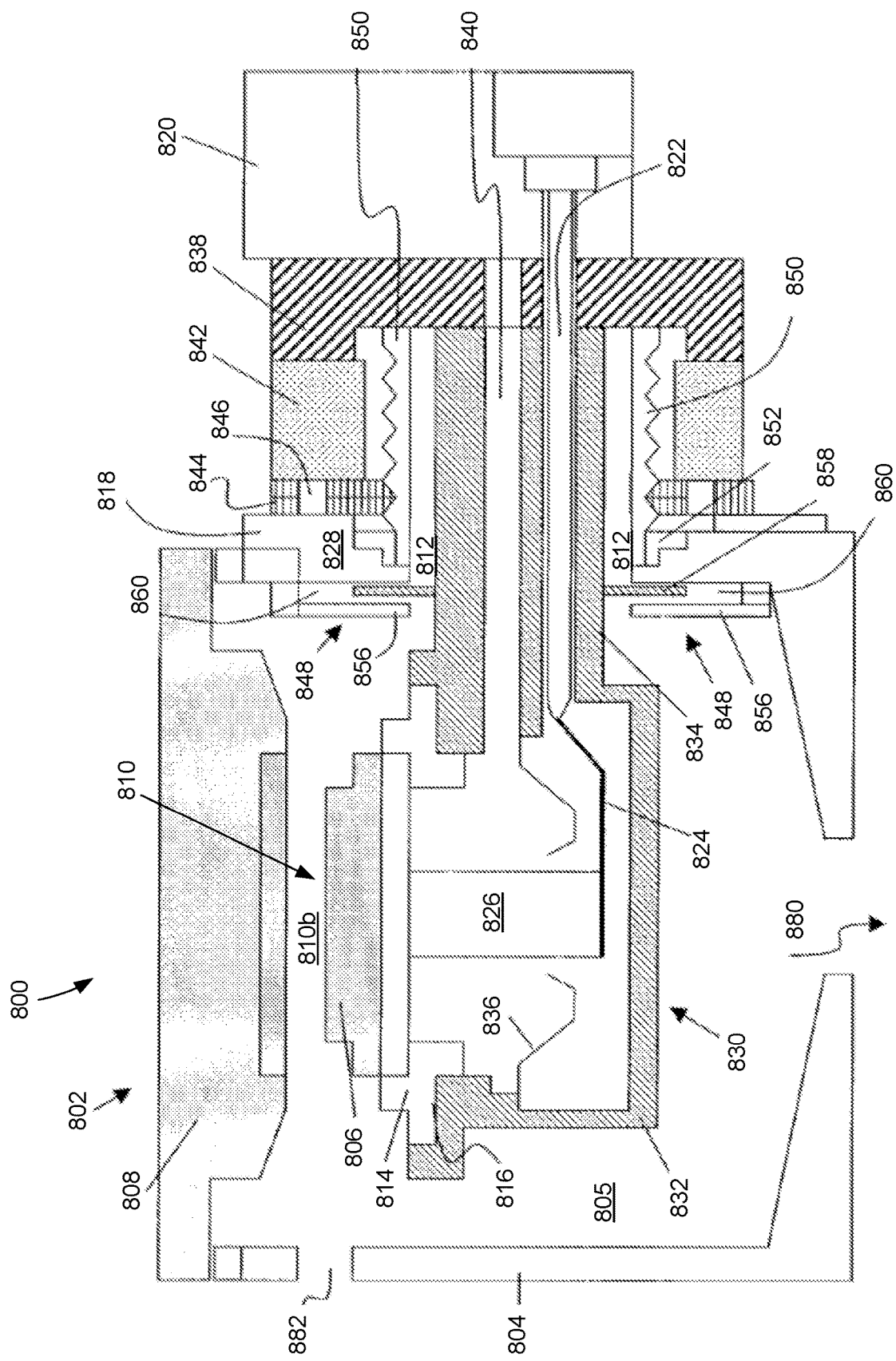
Figure 8C:
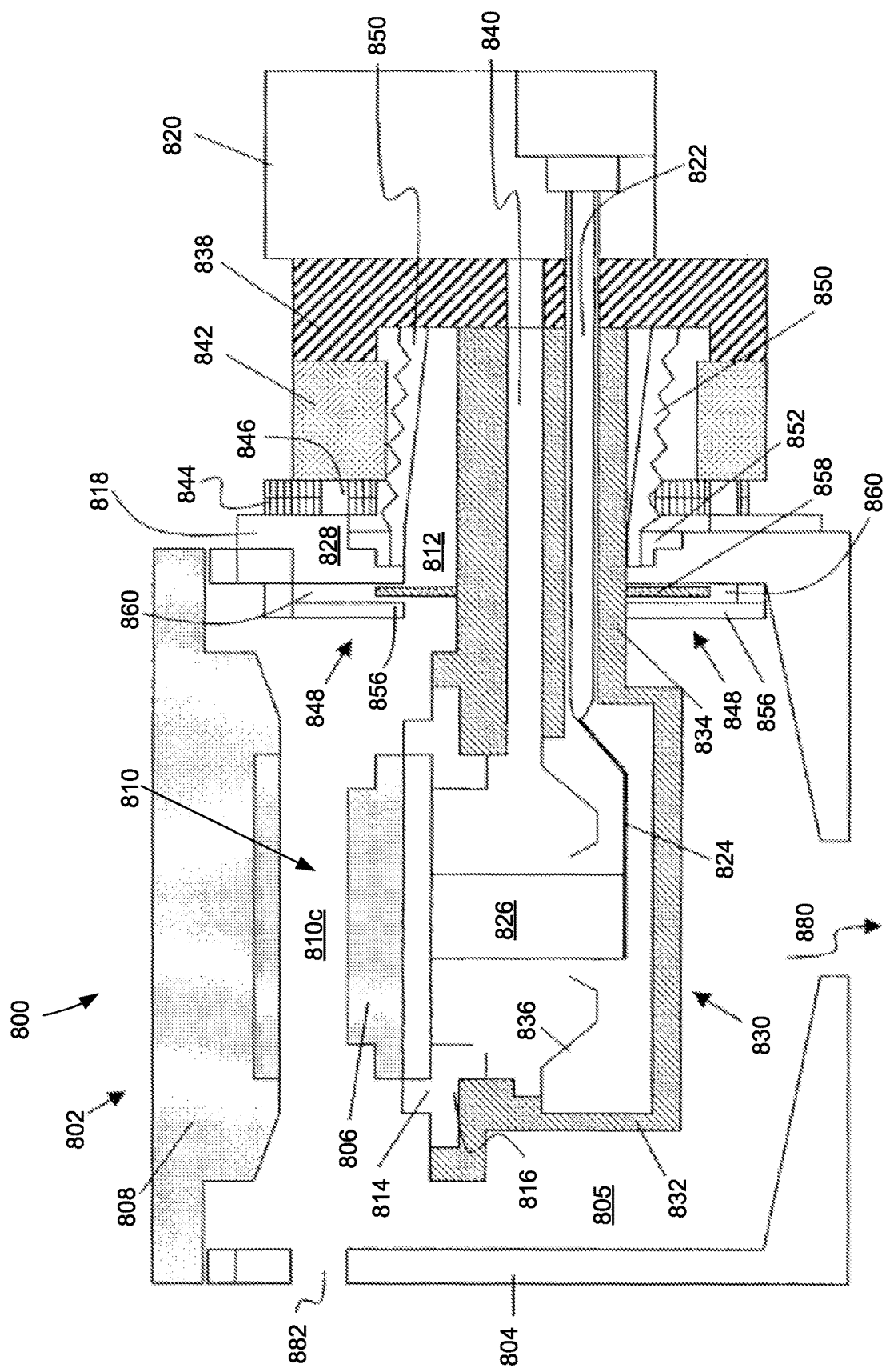

FIGS. 8A-8C illustrate an embodiment of an adjustable gap capacitively coupled confined RF plasma reactor 800 that may be used for performing the etching operations described herein. As depicted, a vacuum chamber 802 includes a chamber housing 804, surrounding an interior space housing a lower electrode 806. In an upper portion of the chamber 802 an upper electrode 808 is vertically spaced apart from the lower electrode 806. Planar surfaces of the upper and lower electrodes 808, 806 are substantially parallel and orthogonal to the vertical direction between the electrodes. Preferably the upper and lower electrodes 808, 806 are circular and coaxial with respect to a vertical axis. A lower surface of the upper electrode 808 faces an upper surface of the lower electrode 806. The spaced apart facing electrode surfaces define an adjustable gap 810 therebetween. During operation, the lower electrode 806 is supplied RF power by an RF power supply (match) 820. RF power is supplied to the lower electrode 806 though an RF supply conduit 822, an RF strap 824 and an RF power member 826. A grounding shield 836 may surround the RF power member 826 to provide a more uniform RF field to the lower electrode 806. As described in commonly-owned U.S. Pat. No. 7,732,728, the entire contents of which are herein incorporated by reference, a wafer is inserted through wafer port 882 and supported in the gap 810 on the lower electrode 806 for processing, a process gas is supplied to the gap 810 and excited into plasma state by the RF power. The upper electrode 808 can be powered or grounded.

In the embodiment shown in FIGS. 8A-8C, the lower electrode 806 is supported on a lower electrode support plate 816. An insulator ring 814 interposed between the lower electrode 806 and the lower electrode support plate 816 insulates the lower electrode 806 from the support plate 816.

An RF bias housing 830 supports the lower electrode 806 on an RF bias housing bowl 832. The bowl 832 is connected through an opening in a chamber wall plate 818 to a conduit support plate 838 by an arm 834 of the RF bias housing 830. In a preferred embodiment, the RF bias housing bowl 832 and RF bias housing arm 834 are integrally formed as one component, however, the arm 834 and bowl 832 can also be two separate components bolted or joined together.

The RF bias housing arm 834 includes one or more hollow passages for passing RF power and facilities, such as gas coolant, liquid coolant, RF energy, cables for lift pin control, electrical monitoring and actuating signals from outside the vacuum chamber 802 to inside the vacuum chamber 802 at a space on the backside of the lower electrode 806. The RF supply conduit 822 is insulated from the RF bias housing arm 834, the RF bias housing arm 834 providing a return path for RF power to the RF power supply 820. A facilities conduit 840 provides a passageway for facility components. Further details of the facility components are described in U.S. Pat. Nos. 5,948,704 and 7,732,728 and are not shown here for simplicity of description. The gap 810 is preferably surrounded by a confinement ring assembly or shroud (not shown), details of which can be found in commonly owned published U.S. Pat. No. 7,740,736 herein incorporated by reference. The interior of the vacuum chamber 802 is maintained at a low pressure by connection to a vacuum pump through vacuum portal 880.

The conduit support plate 838 is attached to an actuation mechanism 842. The actuation mechanism 842, such as a servo mechanical motor, stepper motor or the like is attached to a vertical linear bearing 844, for example, by a screw gear 846 such as a ball screw and motor for rotating the ball screw. During operation to adjust the size of the gap 810, the actuation mechanism 842 travels along the vertical linear bearing 844. FIG. 8A illustrates the arrangement when the actuation mechanism 842 is at a high position on the linear bearing 844 resulting in a small gap 810a. FIG. 8B illustrates the arrangement when the actuation mechanism 842 is at a mid position on the linear bearing 844. As shown, the lower electrode 806, the RF bias housing 830, the conduit support plate 838, the RF power supply 820 have all moved lower with respect to the chamber housing 804 and the upper electrode 808, resulting in a medium size gap 810b.

FIG. 8C illustrates a large gap 810c when the actuation mechanism 842 is at a low position on the linear bearing. Preferably, the upper and lower electrodes 808, 806 remain co-axial during the gap adjustment and the facing surfaces of the upper and lower electrodes across the gap remain parallel.

This embodiment allows the gap 810 between the lower and upper electrodes 806, 808 in the CCP chamber 802 during multi-step process recipes (BARC, HARC, and STRIP etc.) to be adjusted, for example, in order to maintain uniform etch across a large diameter substrate such as 300 mm wafers or flat panel displays. In particular, this chamber pertains to a mechanical arrangement that permits the linear motion necessary to provide the adjustable gap between lower and upper electrodes 806, 808.

FIG. 8A illustrates laterally deflected bellows 850 sealed at a proximate end to the conduit support plate 838 and at a distal end to a stepped flange 828 of chamber wall plate 818. The inner diameter of the stepped flange defines an opening 812 in the chamber wall plate 818 through which the RF bias housing arm 834 passes. The distal end of the bellows 850 is clamped by a clamp ring 852.

The laterally deflected bellows 850 provides a vacuum seal while allowing vertical movement of the RF bias housing 830, conduit support plate 838 and actuation mechanism 842. The RF bias housing 830, conduit support plate 838 and actuation mechanism 842 can be referred to as a cantilever assembly. Preferably, the RF power supply 820 moves with the cantilever assembly and can be attached to the conduit support plate 838. FIG. 8B shows the bellows 850 in a neutral position when the cantilever assembly is at a mid position. FIG. 8C shows the bellows 850 laterally deflected when the cantilever assembly is at a low position.

A labyrinth seal 848 provides a particle barrier between the bellows 850 and the interior of the plasma processing chamber housing 804. A fixed shield 856 is immovably attached to the inside inner wall of the chamber housing 804 at the chamber wall plate 818 so as to provide a labyrinth groove 860 (slot) in which a movable shield plate 858 moves vertically to accommodate vertical movement of the cantilever assembly. The outer portion of the movable shield plate 858 remains in the slot at all vertical positions of the lower electrode 806.

In the embodiment shown, the labyrinth seal 848 includes a fixed shield 856 attached to an inner surface of the chamber wall plate 818 at a periphery of the opening 812 in the chamber wall plate 818 defining a labyrinth groove 860. The movable shield plate 858 is attached and extends radially from the RF bias housing arm 834 where the arm 834 passes through the opening 812 in the chamber wall plate 818. The movable shield plate 858 extends into the labyrinth groove 860 while spaced apart from the fixed shield 856 by a first gap and spaced apart from the interior surface of the chamber wall plate 818 by a second gap allowing the cantilevered assembly to move vertically. The labyrinth seal 848 blocks migration of particles spalled from the bellows 850 from entering the vacuum chamber interior 805 and blocks radicals from process gas plasma from migrating to the bellows 850 where the radicals can form deposits which are subsequently spalled.

FIG. 8A shows the movable shield plate 858 at a higher position in the labyrinth groove 860 above the RF bias housing arm 834 when the cantilevered assembly is in a high position (small gap 810*a*). FIG. 8C shows the movable shield plate 858 at a lower position in the labyrinth groove 860 above the RF bias housing arm 834 when the cantilevered assembly is in a low position (large gap 810*c*). FIG. 8B shows the movable shield plate 858 in a neutral or mid position within the labyrinth groove 860 when the cantilevered assembly is in a mid position (medium gap 810*b*). While the labyrinth seal 848 is shown as symmetrical about the RF bias housing arm 834, in other embodiments the labyrinth seal 848 may be asymmetrical about the RF bias arm 834.

Figure 9:
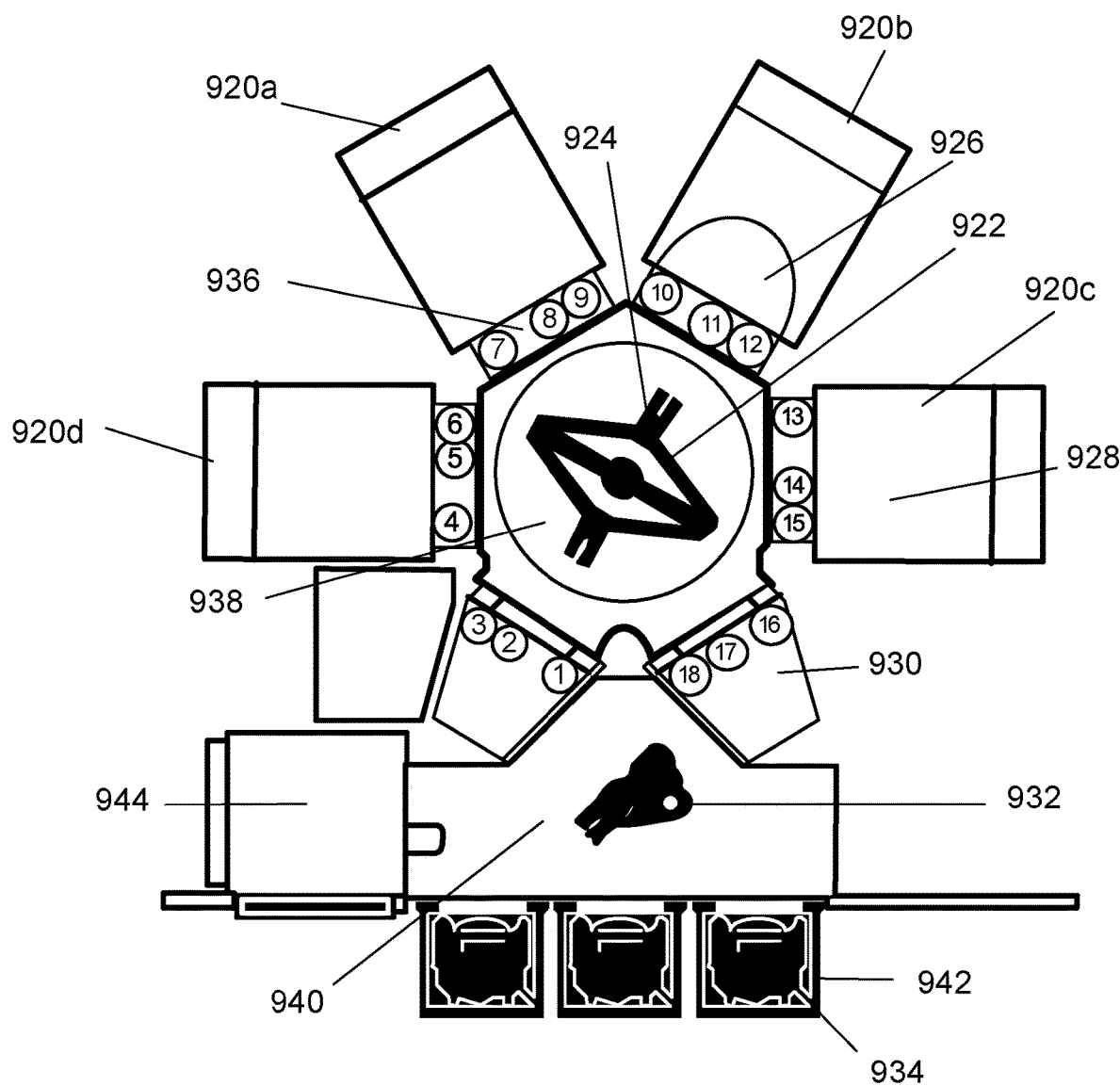
FIG. 9 depicts a semiconductor process cluster architecture with various modules that interface with a vacuum transfer module.

FIG. 9 depicts a semiconductor process cluster architecture with various modules that interface with a vacuum transfer module 938 (VTM). The arrangement of transfer modules to "transfer" substrates among multiple storage facilities and processing modules may be referred to as a "cluster tool architecture" system. Airlock 930, also known as a loadlock or transfer module, is shown in VTM 938 with four processing modules 920*a*-920*d*, which may be individually optimized to perform various fabrication processes. By way of example, processing modules 920*a*-920*d* may be implemented to perform substrate etching, deposition, ion implantation, substrate cleaning, sputtering, and/or other semiconductor processes as well as laser metrology and other defect detection and defect identification methods. One or more of the processing modules (any of 920*a*-920*d*) may be implemented as disclosed herein, i.e., for etching recessed features into substrates. Airlock 930 and process modules 920*a*-920*d* may be referred to as "stations." Each station has a facet 936 that interfaces the station to VTM 938. Inside the facets, sensors 1-18 are used to detect the passing of substrate 926 when moved between respective stations.

Robot 922 transfers substrates between stations. In one implementation, the robot may have one arm, and in another implementation, the robot may have two arms, where each arm has an end effector 924 to pick substrates for transport. Front-end robot 932, in atmospheric transfer module (ATM) 940, may be used to transfer substrates from cassette or Front Opening Unified Pod (FOUP) 934 in Load Port Module (LPM) 942 to airlock 930. Module center 928 inside process modules 920*a*-920*d* may be one location for placing the substrate. Aligner 944 in ATM 940 may be used to align substrates.

In an exemplary processing method, a substrate is placed in one of the FOUPs 934 in the LPM 942. Front-end robot 932 transfers the substrate from the FOUP 934 to the aligner 944, which allows the substrate 926 to be properly centered before it is etched, or deposited upon, or otherwise processed. After being aligned, the substrate is moved by the front-end robot 932 into an airlock 930. Because airlock modules have the ability to match the environment between an ATM and a VTM, the substrate is able to move between the two pressure environments without being damaged. From the airlock module 930, the substrate is moved by robot 922 through VTM 938 and into one of the process modules 920*a*-920*d*, for example process module 920*a*. In order to achieve this substrate movement, the robot 922 uses end effectors 924 on each of its arms. In process module 920*a*, the substrate undergoes etching as described. Next, the robot 922 moves the substrate out of processing module 920*a* to its next desired position.

It should be noted that the computer controlling the substrate movement can be local to the cluster architecture, or can be located external to the cluster architecture in the manufacturing floor, or in a remote location and connected to the cluster architecture via a network.

Deposition Apparatuses

Figure 10:
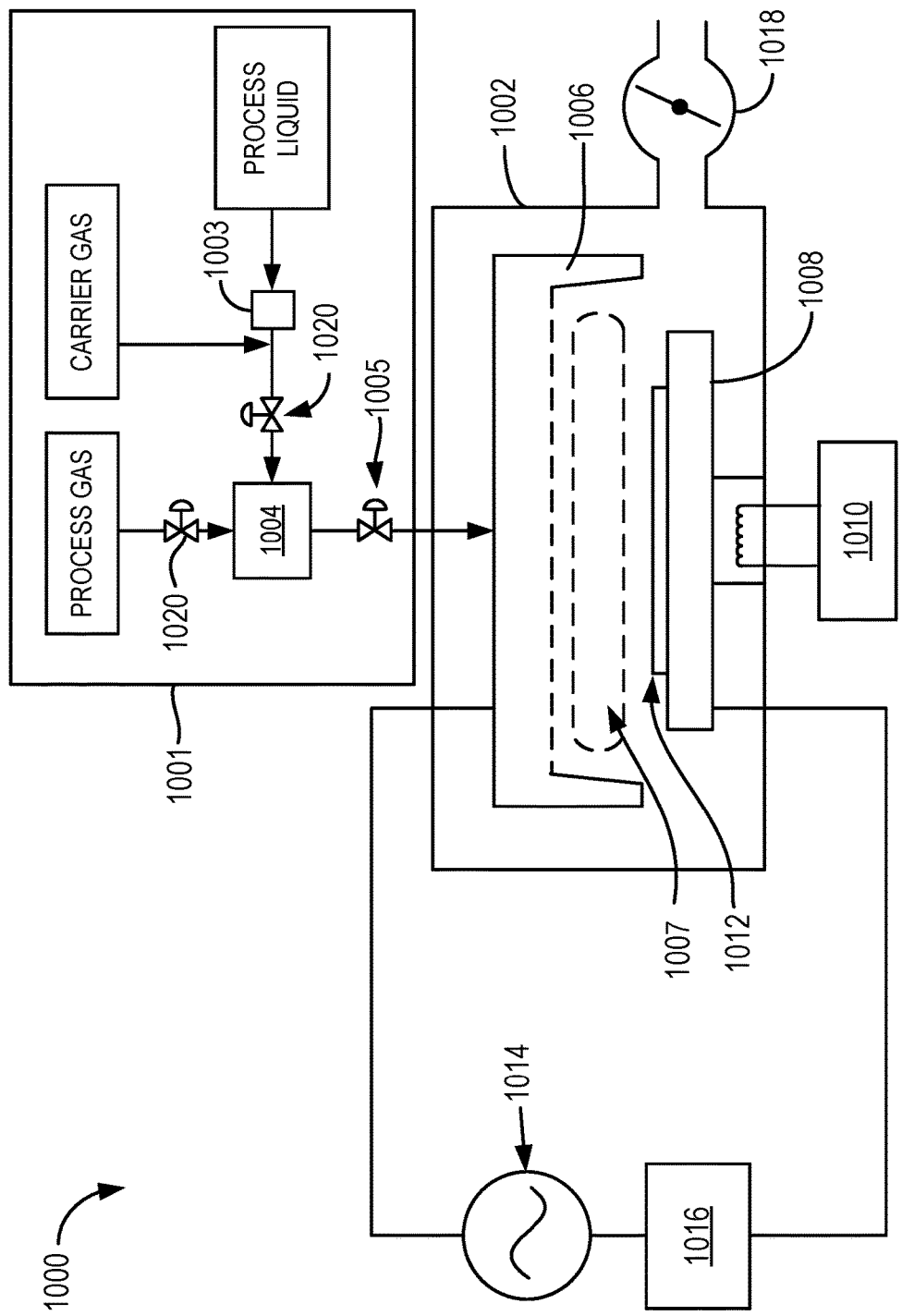
FIG. 10 depicts a schematic view of a process station that may be used to deposit material.

FIG. 10 schematically shows an embodiment of a process station 1000 that may be used to deposit material using atomic layer deposition (ALD) and/or chemical vapor deposition (CVD), either of which may be plasma enhanced. For simplicity, the process station 1000 is depicted as a standalone process station having a process chamber body 1002 for maintaining a low-pressure environment. However, it will be appreciated that a plurality of process stations 1000 may be included in a common process tool environment. Further, it will be appreciated that, in some embodiments, one or more hardware parameters of process station 1000, including those discussed in detail below, may be adjusted programmatically by one or more computer controllers.

Process station 1000 fluidly communicates with reactant delivery system 1001 for delivering process gases to a distribution showerhead 1006. Reactant delivery system 1001 includes a mixing vessel 1004 for blending and/or conditioning process gases for delivery to showerhead 1006. One or more mixing vessel inlet valves 1020 may control introduction of process gases to mixing vessel 1004. Similarly, a showerhead inlet valve 1005 may control introduction of process gasses to the showerhead 1006.

Some reactants, like BTBAS, may be stored in liquid form prior to vaporization at and subsequent delivery to the process station. For example, the embodiment of FIG. 10 includes a vaporization point 1003 for vaporizing liquid reactant to be supplied to mixing vessel 1004. In some embodiments, vaporization point 1003 may be a heated vaporizer. The reactant vapor produced from such vaporizers may condense in downstream delivery piping. Exposure of incompatible gases to the condensed reactant may create small particles. These small particles may clog piping, impede valve operation, contaminate substrates, etc. Some approaches to addressing these issues involve sweeping and/or evacuating the delivery piping to remove residual reactant. However, sweeping the delivery piping may increase process station cycle time, degrading process station throughput. Thus, in some embodiments, delivery piping downstream of vaporization point 1003 may be heat traced. In some examples, mixing vessel 1004 may also be heat traced. In one non-limiting example, piping downstream of vaporization point 1003 has an increasing temperature profile extending from approximately 100° C. to approximately 150° C. at mixing vessel 1004.

In some embodiments, reactant liquid may be vaporized at a liquid injector. For example, a liquid injector may inject pulses of a liquid reactant into a carrier gas stream upstream of the mixing vessel. In one scenario, a liquid injector may vaporize reactant by flashing the liquid from a higher pressure to a lower pressure. In another scenario, a liquid injector may atomize the liquid into dispersed microdroplets that are subsequently vaporized in a heated delivery pipe. It will be appreciated that smaller droplets may vaporize faster than larger droplets, reducing a delay between liquid injection and complete vaporization. Faster vaporization may reduce a length of piping downstream from vaporization point 1003. In one scenario, a liquid injector may be mounted directly to mixing vessel 1004. In another scenario, a liquid injector may be mounted directly to showerhead 1006.

In some embodiments, a liquid flow controller upstream of vaporization point 1003 may be provided for controlling a mass flow of liquid for vaporization and delivery to process station 1000. For example, the liquid flow controller (LFC) may include a thermal mass flow meter (MFM) located downstream of the LFC. A plunger valve of the LFC may then be adjusted responsive to feedback control signals provided by a proportional-integral-derivative (PID) controller in electrical communication with the MFM. However, it may take one second or more to stabilize liquid flow using feedback control. This may extend a time for dosing a liquid reactant. Thus, in some embodiments, the LFC may be dynamically switched between a feedback control mode and a direct control mode. In some embodiments, the LFC may be dynamically switched from a feedback control mode to a direct control mode by disabling a sense tube of the LFC and the PID controller.

Showerhead 1006 distributes process gases toward substrate 1012. In the embodiment shown in FIG. 10, substrate 1012 is located beneath showerhead 1006, and is shown resting on a pedestal 1008. It will be appreciated that showerhead 1006 may have any suitable shape, and may have any suitable number and arrangement of ports for distributing processes gases to substrate 1012.

In some embodiments, a microvolume 1007 is located beneath showerhead 1006. Performing an ALD and/or CVD process in a microvolume rather than in the entire volume of a process station may reduce reactant exposure and sweep times, may reduce times for altering process conditions (e.g., pressure, temperature, etc.), may limit an exposure of process station robotics to process gases, etc. Example microvolume sizes include, but are not limited to, volumes between 0.1 liter and 2 liters. This microvolume also impacts productivity throughput. While deposition rate per cycle drops, the cycle time also simultaneously reduces. In certain cases, the effect of the latter is dramatic enough to improve overall throughput of the module for a given target thickness of film.

In some embodiments, pedestal 1008 may be raised or lowered to expose substrate 1012 to microvolume 1007 and/or to vary a volume of microvolume 1007. For example, in a substrate transfer phase, pedestal 1008 may be lowered to allow substrate 1012 to be loaded onto pedestal 1008. During a deposition process phase, pedestal 1008 may be raised to position substrate 1012 within microvolume 1007. In some embodiments, microvolume 1007 may completely enclose substrate 1012 as well as a portion of pedestal 1008 to create a region of high flow impedance during a deposition process.

Optionally, pedestal 1008 may be lowered and/or raised during portions the deposition process to modulate process pressure, reactant concentration, etc., within microvolume 1007. In one scenario where process chamber body 1002 remains at a base pressure during the deposition process, lowering pedestal 1008 may allow microvolume 1007 to be evacuated. Example ratios of microvolume to process chamber volume include, but are not limited to, volume ratios between 1:900 and 1:10. It will be appreciated that, in some embodiments, pedestal height may be adjusted programmatically by a suitable computer controller.

In another scenario, adjusting a height of pedestal 1008 may allow a plasma density to be varied during plasma activation and/or treatment cycles included in the deposition process. At the conclusion of the deposition process phase, pedestal 1008 may be lowered during another substrate transfer phase to allow removal of substrate 1012 from pedestal 1008.

While the example microvolume variations described herein refer to a height-adjustable pedestal, it will be appreciated that, in some embodiments, a position of showerhead 1006 may be adjusted relative to pedestal 1008 to vary a volume of microvolume 1007. Further, it will be appreciated that a vertical position of pedestal 1008 and/or showerhead 1006 may be varied by any suitable mechanism within the scope of the present disclosure. In some embodiments, pedestal 1008 may include a rotational axis for rotating an orientation of substrate 1012. It will be appreciated that, in some embodiments, one or more of these example adjustments may be performed programmatically by one or more suitable computer controllers.

Returning to the embodiment shown in FIG. 10, showerhead 1006 and pedestal 1008 electrically communicate with RF power supply 1014 and matching network 1016 for powering a plasma. In some embodiments, the plasma energy may be controlled by controlling one or more of a process station pressure, a gas concentration, an RF source power, an RF source frequency, and a plasma power pulse timing. For example, RF power supply 1014 and matching network 1016 may be operated at any suitable power to form a plasma having a desired composition of radical species. Examples of suitable powers are included above. Likewise, RF power supply 1014 may provide RF power of any suitable frequency. In some embodiments, RF power supply 1014 may be configured to control high- and low-frequency RF power sources independently of one another. Example low-frequency RF frequencies may include, but are not limited to, frequencies between 50 kHz and 900 kHz. Example high-frequency RF frequencies may include, but are not limited to, frequencies between 1.8 MHz and 2.45 GHz. It will be appreciated that any suitable parameters may be modulated discretely or continuously to provide plasma energy for the surface reactions. In one non-limiting example, the plasma power may be intermittently pulsed to reduce ion bombardment with the substrate surface relative to continuously powered plasmas.

In some embodiments, the plasma may be monitored in-situ by one or more plasma monitors. In one scenario, plasma power may be monitored by one or more voltage, current sensors (e.g., VI probes). In another scenario, plasma density and/or process gas concentration may be measured by one or more optical emission spectroscopy sensors (OES). In some embodiments, one or more plasma parameters may be programmatically adjusted based on measurements from such in-situ plasma monitors. For example, an OES sensor may be used in a feedback loop for providing programmatic control of plasma power. It will be appreciated that, in some embodiments, other monitors may be used to monitor the plasma and other process characteristics. Such monitors may include, but are not limited to, infrared (IR) monitors, acoustic monitors, and pressure transducers.

In some embodiments, the plasma may be controlled via input/output control (IOC) sequencing instructions. In one example, the instructions for setting plasma conditions for a plasma process phase may be included in a corresponding plasma activation recipe phase of a deposition process recipe. In some cases, process recipe phases may be sequentially arranged, so that all instructions for a deposition process phase are executed concurrently with that process phase. In some embodiments, instructions for setting one or more plasma parameters may be included in a recipe phase preceding a plasma process phase. For example, a first recipe phase may include instructions for setting a flow rate of an inert and/or a reactant gas, instructions for setting a plasma generator to a power set point, and time delay instructions for the first recipe phase. A second, subsequent recipe phase may include instructions for enabling the plasma generator and time delay instructions for the second recipe phase. A third recipe phase may include instructions for disabling the plasma generator and time delay instructions for the third recipe phase. It will be appreciated that these recipe phases may be further subdivided and/or iterated in any suitable way within the scope of the present disclosure.

In some deposition processes, plasma strikes last on the order of a few seconds or more in duration. In certain implementations, much shorter plasma strikes may be used. These may be on the order of 10 ms to 1 second, typically, about 20 to 80 ms, with 50 ms being a specific example. Such very short RF plasma strikes require extremely quick stabilization of the plasma. To accomplish this, the plasma generator may be configured such that the impedance match is set preset to a particular voltage, while the frequency is allowed to float. Conventionally, high-frequency plasmas are generated at an RF frequency at about 13.56 MHz. In various embodiments disclosed herein, the frequency is allowed to float to a value that is different from this standard value. By permitting the frequency to float while fixing the impedance match to a predetermined voltage, the plasma can stabilize much more quickly, a result which may be important when using the very short plasma strikes associated with some types of deposition cycles.

In some embodiments, pedestal 1008 may be temperature controlled via heater 1010. Further, in some embodiments, pressure control for deposition process station 1000 may be provided by butterfly valve 1018. As shown in the embodiment of FIG. 10, butterfly valve 1018 throttles a vacuum provided by a downstream vacuum pump (not shown). However, in some embodiments, pressure control of process station 1000 may also be adjusted by varying a flow rate of one or more gases introduced to process station 1000.

Figure 11:
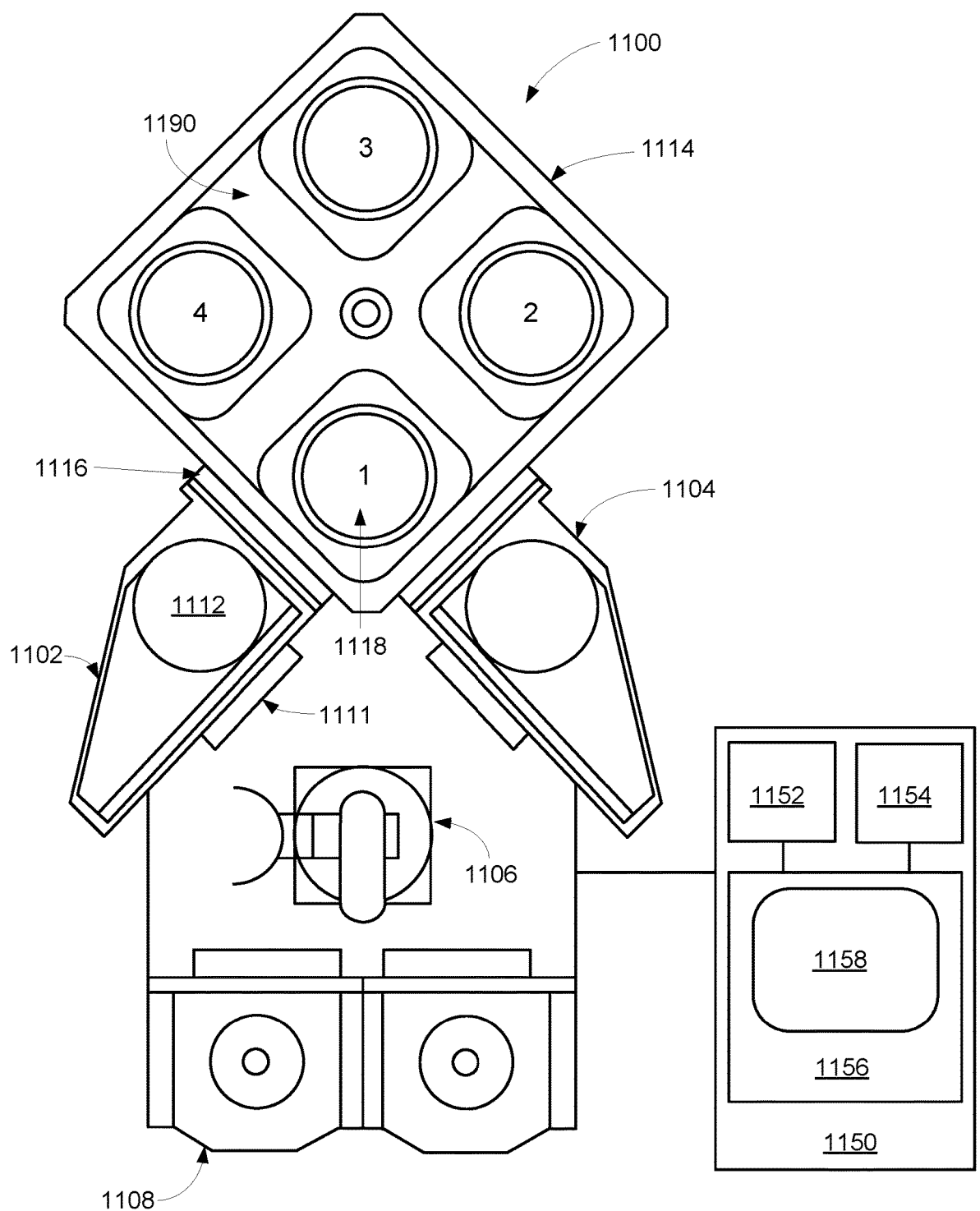
FIG. 11 depicts a schematic view of a multi-station processing tool.

FIG. 11 shows a schematic view of an embodiment of a multi-station processing tool 1100 with an inbound load lock 1102 and an outbound load lock 1104, either or both of which may comprise a remote plasma source. A robot 1106, at atmospheric pressure, is configured to move wafers from a cassette loaded through a pod 1108 into inbound load lock 1102 via an atmospheric port 1110. A wafer is placed by the robot 1106 on a pedestal 1112 in the inbound load lock 1102, the atmospheric port 1110 is closed, and the load lock is pumped down. Where the inbound load lock 1102 comprises a remote plasma source, the wafer may be exposed to a remote plasma treatment in the load lock prior to being introduced into a processing chamber 1114. Further, the wafer also may be heated in the inbound load lock 1102 as well, for example, to remove moisture and adsorbed gases. Next, a chamber transport port 1116 to processing chamber 1114 is opened, and another robot (not shown) places the wafer into the reactor on a pedestal of a first station shown in the reactor for processing. While the embodiment depicted in FIG. 11 includes load locks, it will be appreciated that, in some embodiments, direct entry of a wafer into a process station may be provided.

The depicted processing chamber 1114 comprises four process stations, numbered from 1 to 4 in the embodiment shown in FIG. 11. Each station has a heated pedestal (shown at 1118 for station 1), and gas line inlets. It will be appreciated that in some embodiments, each process station may have different or multiple purposes. While the depicted processing chamber 1114 comprises four stations, it will be understood that a processing chamber according to the present disclosure may have any suitable number of stations. For example, in some embodiments, a processing chamber may have five or more stations, while in other embodiments a processing chamber may have three or fewer stations.

FIG. 11 also depicts an embodiment of a wafer handling system 1190 for transferring wafers within processing chamber 1114. In some embodiments, wafer handling system 1190 may transfer wafers between various process stations and/or between a process station and a load lock. It will be appreciated that any suitable wafer handling system may be employed. Non-limiting examples include wafer carousels and wafer handling robots. FIG. 11 also depicts an embodiment of a system controller 1150 employed to control process conditions and hardware states of process tool 1100. System controller 1150 may include one or more memory devices 1156, one or more mass storage devices 1154, and one or more processors 1152. Processor 1152 may include a CPU or computer, analog and/or digital input/output connections, stepper motor controller boards, etc.

Figure 12:
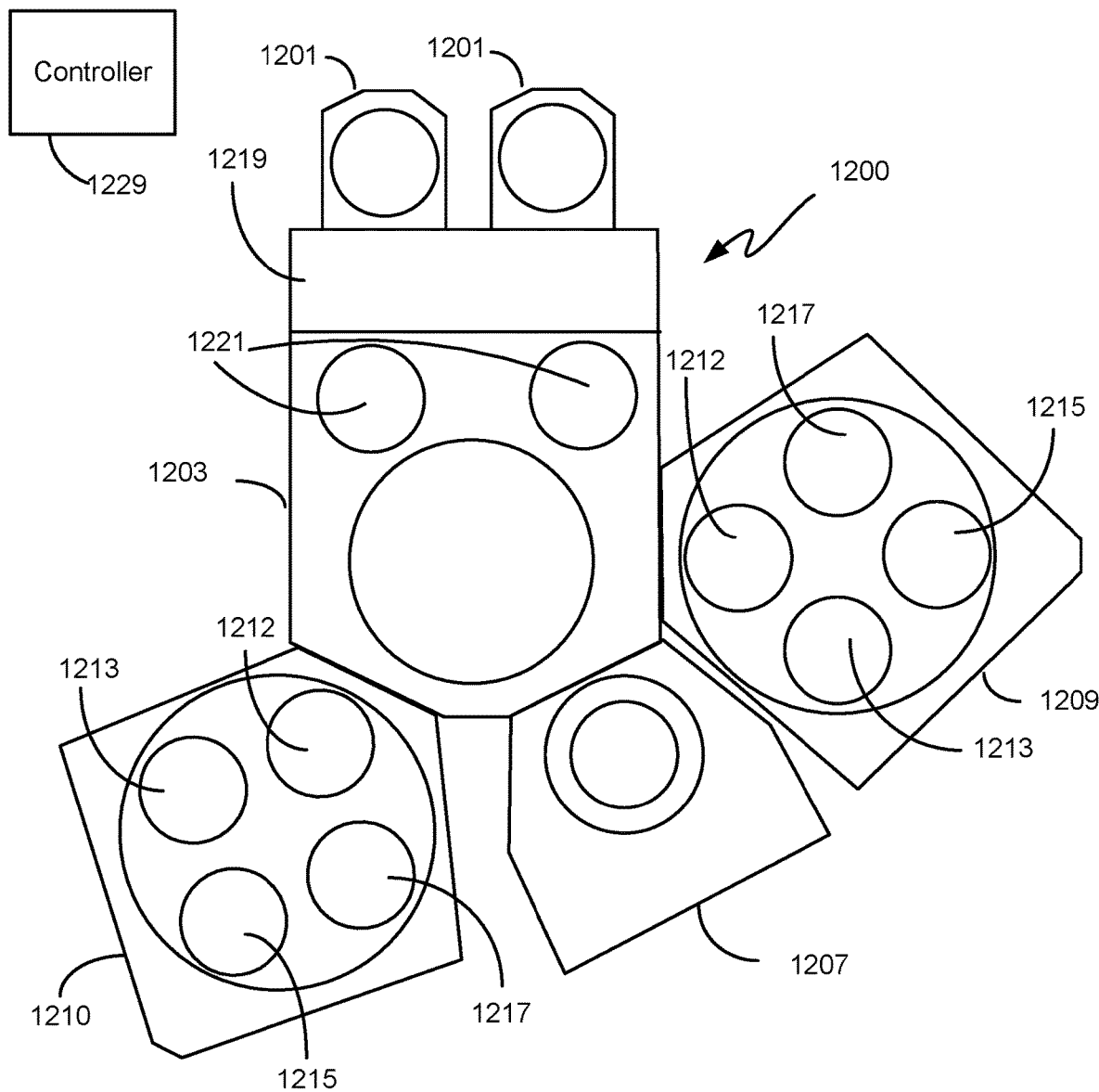
FIG. 12 depicts a block diagram of a processing system suitable for conducting thin film deposition processes in accordance with certain embodiments.

FIG. 12 is a block diagram of a processing system suitable for conducting thin film deposition processes in accordance with certain embodiments. The system 1200 includes a transfer module 1203. The transfer module 1203 provides a clean, pressurized environment to minimize risk of contamination of substrates being processed as they are moved between various reactor modules. Mounted on the transfer module 1203 are two multi-station reactors 1209 and 1210, each capable of performing atomic layer deposition (ALD)

and/or chemical vapor deposition (CVD) according to certain embodiments. Reactors 1209 and 1210 may include multiple stations 1211, 1213, 1215, and 1217 that may sequentially or non-sequentially perform operations in accordance with disclosed embodiments. The stations may include a heated pedestal or substrate support, one or more gas inlets or showerhead or dispersion plate.

Also mounted on the transfer module 1203 may be one or more single or multi-station modules 1207 capable of performing plasma or chemical (non-plasma) pre-cleans, or any other processes described in relation to the disclosed methods. The module 1207 may in some cases be used for various treatments to, for example, prepare a substrate for a deposition process. The module 1207 may also be designed/configured to perform various other processes such as etching or polishing. The system 1200 also includes one or more wafer source modules 1201, where wafers are stored before and after processing. An atmospheric robot (not shown) in the atmospheric transfer chamber 1219 may first remove wafers from the source modules 1201 to loadlocks 1221. A wafer transfer device (generally a robot arm unit) in the transfer module 1203 moves the wafers from loadlocks 1221 to and among the modules mounted on the transfer module 1203.

In various embodiments, a system controller 1229 is employed to control process conditions during deposition as described herein.

Figure 13:
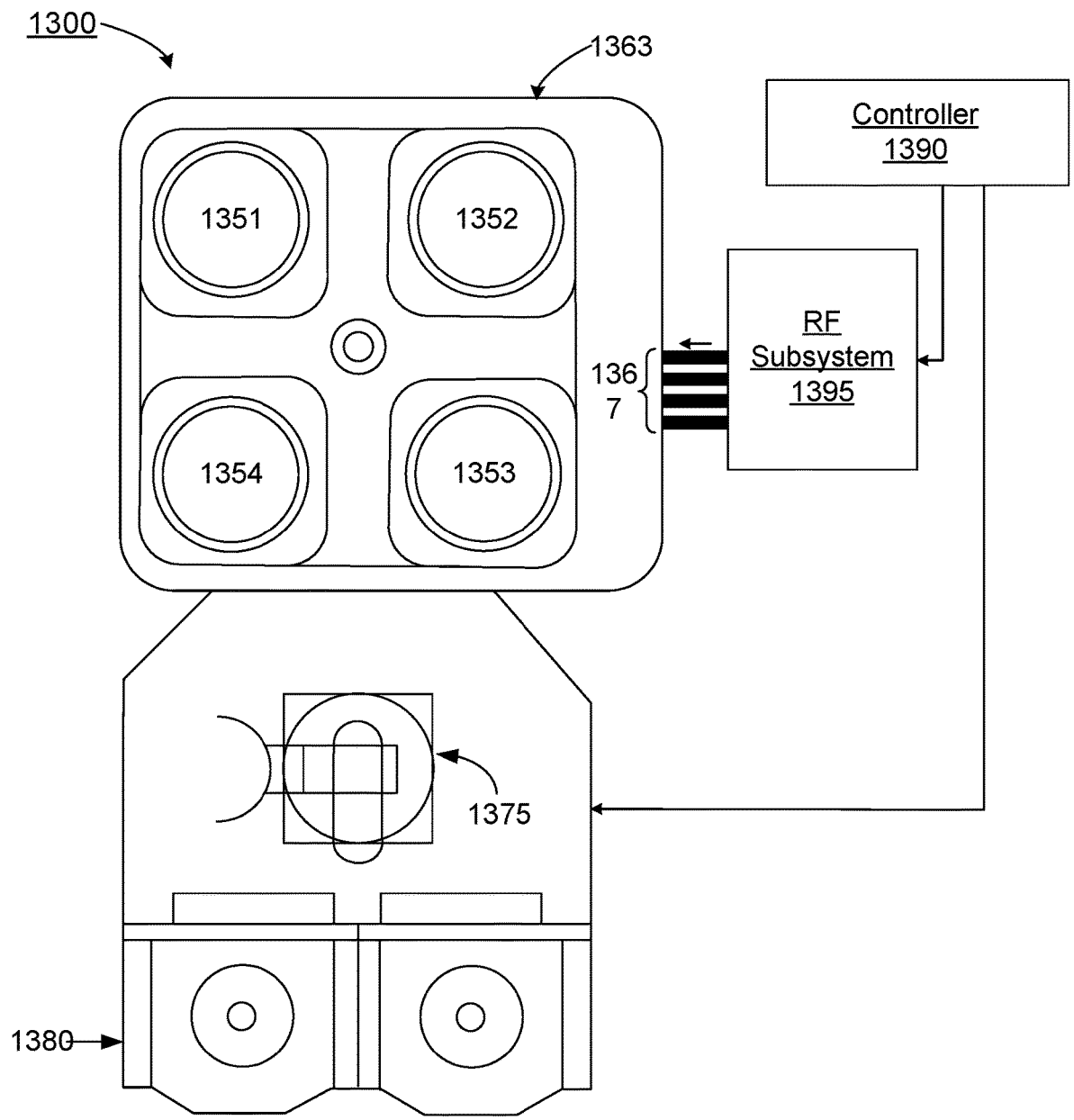
FIG. 13 depicts a schematic view of a multi-station processing tool.

It may be appreciated that a plurality of process stations may be included in a multi-station processing tool environment, such as shown in FIG. 13, which depicts a schematic view of an embodiment of a multi-station processing tool. Processing apparatus 1300 employs an integrated circuit fabrication chamber 1363 that includes multiple fabrication process stations, each of which may be used to perform processing operations on a substrate held in a wafer holder, such as a pedestal, at a particular process station. In the embodiment of FIG. 13, the integrated circuit fabrication chamber 1363 is shown having four process stations 1351, 1352, 1353, and 1354. Other similar multi-station processing apparatuses may have more or fewer process stations depending on the implementation and, for example, a desired level of parallel wafer processing, size/space constraints, cost constraints, etc. Also shown in FIG. 13 is substrate handler robot 1375, which may operate under the control of system controller 1390, configured to move substrates from a wafer cassette (not shown in FIG. 13) from loading port 1380 and into integrated circuit fabrication chamber 1363, and onto one of process stations 1351, 1352, 1353, and 1354.

FIG. 13 also depicts an embodiment of a system controller 1390 employed to control process conditions and hardware states of processing apparatus 1300. System controller 1390 may include one or more memory devices, one or more mass storage devices, and one or more processors, as described herein.

RF subsystem 1395 may generate and convey RF power to integrated circuit fabrication chamber 1363 via radio frequency input ports 1367. In particular embodiments, integrated circuit fabrication chamber 1363 may comprise input ports in addition to radio frequency input ports 1367 (additional input ports not shown in FIG. 13). Accordingly, integrated circuit fabrication chamber 1363 may utilize 8 RF input ports. In particular embodiments, process stations 1351-1354 of integrated circuit fabrication chamber 165 may each utilize first and second input ports in which a first input port may convey a signal having a first frequency and in which a second input port may convey a signal having a second frequency. Use of dual frequencies may bring about enhanced plasma characteristics.

Figure 14:
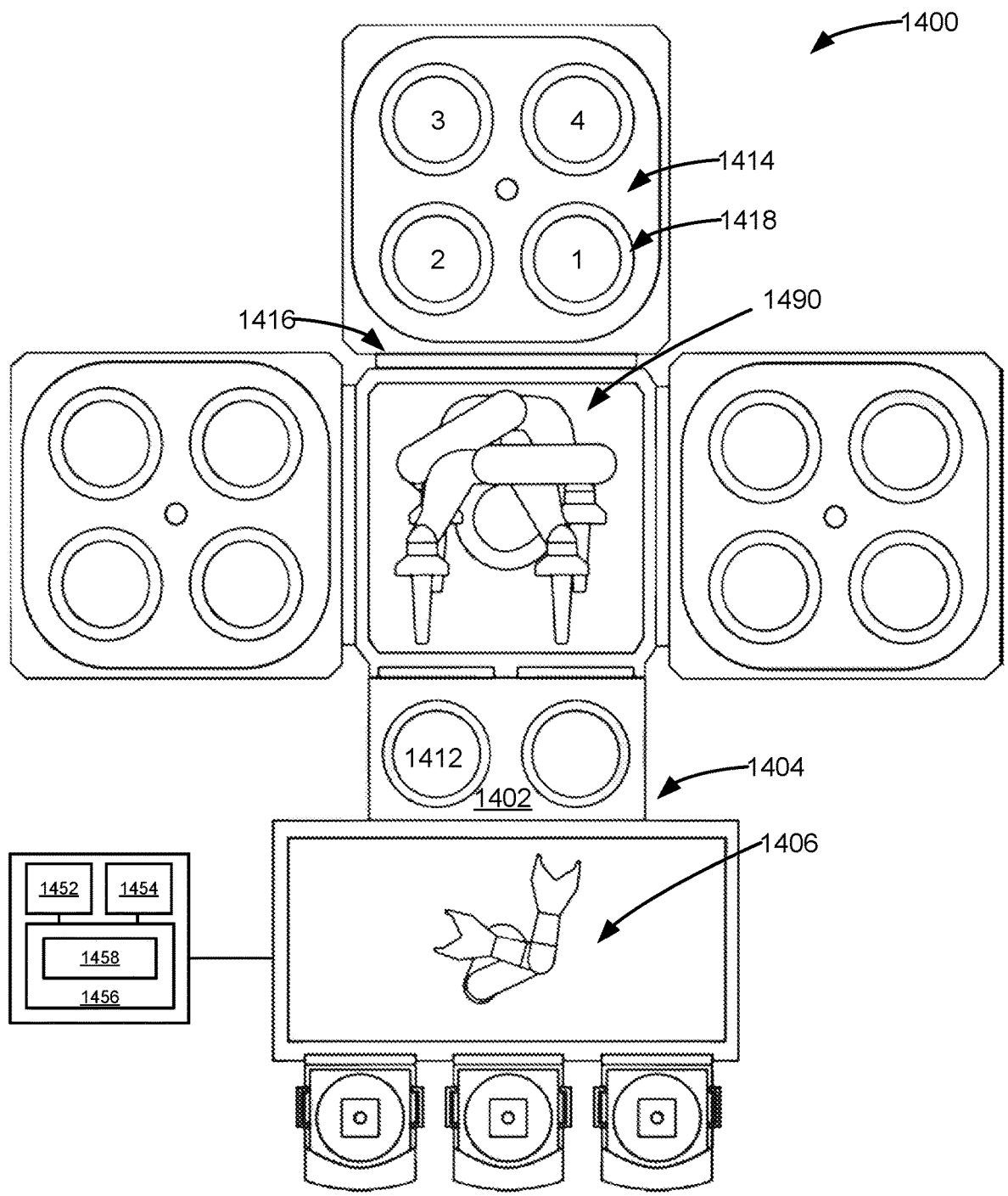
FIG. 14 depicts another schematic view of a multi-station processing tool.

As described above, one or more process stations may be included in a multi-station processing tool. FIG. 14 shows a schematic view of an embodiment of a multi-station processing tool 1400 with an inbound load lock 1402 and an outbound load lock 1404, either or both of which may comprise a remote plasma source. A robot 1406, at atmospheric pressure, is configured to move substrates or wafers from a cassette loaded through a pod 1408 into inbound load lock 1402 via an atmospheric port 1410. A substrate is placed by the robot 1406 on a pedestal 1412 in the inbound load lock 1402, the atmospheric port 1410 is closed, and the load lock is pumped down. Where the inbound load lock 1402 comprises a remote plasma source, the substrate may be exposed to a remote plasma treatment in the load lock prior to being introduced into a processing chamber 1414. Further, the substrate also may be heated in the inbound load lock 1402 as well, for example, to remove moisture and adsorbed gases. Next, a chamber transport port 1416 to processing chamber 1414 is opened, and another robot (not shown) places the substrate into the reactor on a pedestal of a first station shown in the reactor for processing. While the embodiment depicted in FIG. 14 includes load locks, it will be appreciated that, in some embodiments, direct entry of a substrate into a process station may be provided. In various embodiments, the soak gas is introduced to the station when the substrate is placed by the robot 1406 on the pedestal 1412.

The depicted processing chamber 1414 comprises four process stations, numbered from 1 to 4 in the embodiment shown in FIG. 14. Each station has a heated pedestal (shown at 1418 for station 1), and gas line inlets. It will be appreciated that in some embodiments, each process station may have different or multiple purposes. For example, in some embodiments, a process station may be switchable between an ALD and PEALD process mode. Additionally or alternatively, in some embodiments, processing chamber 1414 may include one or more matched pairs of ALD and plasma-enhanced ALD process stations. While the depicted processing chamber 1414 includes four stations, it will be understood that a processing chamber according to the present disclosure may have any suitable number of stations. For example, in some embodiments, a processing chamber may have five or more stations, while in other embodiments a processing chamber may have three or fewer stations.

FIG. 14 depicts an embodiment of a wafer handling system 1490 for transferring substrates within processing chamber 1414. In some embodiments, wafer handling system 1490 may transfer substrates between various process stations and/or between a process station and a load lock. It will be appreciated that any suitable wafer handling system may be employed. Non-limiting examples include wafer carousels and wafer handling robots. FIG. 14 also depicts an embodiment of a system controller 1450 employed to control process conditions and hardware states of process tool 1400. System controller 1450 may include one or more memory devices 1456, one or more mass storage devices 1454, and one or more processors 1452. Processor 1452 may include a CPU or computer, analog and/or digital input/output connections, stepper motor controller boards, etc. In some embodiments, system controller 1450 includes machine-readable instructions for performing operations such as those described herein.

In some embodiments, system controller 1450 controls the activities of process tool 1400. System controller 1450 executes system control software 1458 stored in mass storage device 1454, loaded into memory device 1456, and executed on processor 1452. Alternatively, the control logic may be hard coded in the system controller 1450. Applications Specific Integrated Circuits, Programmable Logic Devices (e.g., field-programmable gate arrays, or FPGAs) and the like may be used for these purposes. In the following discussion, wherever "software" or "code" is used, functionally comparable hard coded logic may be used in its place. System control software 1458 may include instructions for controlling the timing, mixture of gases, amount of gas flow, chamber and/or station pressure, chamber and/or station temperature, substrate temperature, target power levels, RF power levels, substrate pedestal, chuck and/or susceptor position, and other parameters of a particular process performed by process tool 1400. System control software 1458 may be configured in any suitable way. For example, various process tool component subroutines or control objects may be written to control operation of the process tool components used to carry out various process tool processes. System control software 1458 may be coded in any suitable computer readable programming language.

While the subject matter disclosed herein has been particularly described with respect to the illustrated embodiments, it will be appreciated that various alterations, modifications and adaptations may be made based on the present disclosure, and are intended to be within the scope of the present invention. It is to be understood that the description is not limited to the disclosed embodiments but, on the contrary, is intended to cover various modifications and equivalent arrangements included within the scope of the claims.

What is claimed is:

1. A method, comprising:
    providing a substrate to a processing chamber, the substrate having a first material adjacent to and covering a surface of a second material;
    modifying a layer of the first material by flowing a first process gas onto the substrate and thereby creating a modified layer of the first material;
    removing the modified layer of the first material by flowing a second process gas onto the substrate; and
    converting, when the surface of the second material is uncovered via removal of the modified layer, the surface to a converted layer of the second material by flowing a third process gas onto the substrate, wherein the first and second process gases are less reactive with the converted layer than with the first material and the second material.

2. The method of claim 1, further comprising:
    modifying, after the converting, the converted layer to a modified converted layer of material by flowing a fourth process gas onto the substrate; and
    removing the modified converted layer by flowing a fifth process gas onto the substrate.

3. The method of claim 1, wherein flowing the third process gas occurs before the modifying.

4. The method of claim 1, wherein flowing the third process gas occurs after the modifying.

5. The method of claim 4, wherein flowing the third process gas occurs before the removing.

6. The method of claim 5, further comprising flowing a purge gas after flowing the third process gas and before the removing.

7. The method of claim 4, wherein flowing the third process gas occurs after the removing.

8. The method of claim 1, wherein flowing the third process gas onto the substrate at least partially overlaps with flowing the first process gas onto the substrate.

9. The method of claim 1, wherein flowing the third process gas onto the substrate at least partially overlaps with flowing the second process gas onto the substrate.

10. The method of claim 1, wherein flowing the third process gas onto the substrate at least partially overlaps with flowing the first process gas onto the substrate and with flowing the second process gas onto the substrate.

11. The method of claim 1, wherein the converting occurs when the surface of the second material is uncovered during or after the removing of the first material.

12. The method of claim 1, wherein:
    during the removing, the second process gas removes the modified layer of the first material at a first etch rate, and
    during the removing, the second process gas removes the converted layer at a second etch rate that is about equal to or less than 50% of the first etch rate.

13. The method of claim 12, wherein the second etch rate is about equal to or less than 15% of the first etch rate.

14. The method of claim 12, wherein during the removing, the second process gas is capable of removing the second material at a third etch rate higher than the first etch rate.

15. The method of claim 1, wherein:
    the first process gas comprises modifying molecules,
    the second process gas comprises removal molecules, and
    the third process gas comprises converting molecules.

16. The method of claim 1, wherein the third process gas comprises a precursor.

17. The method of claim 1, wherein the converted layer is a monoatomic layer of the second material.

18. The method of claim 1, wherein the first material and the second material are oxides.

19. The method of claim 1, wherein the first material and/or the second material are semiconductor oxides.

20. The method of claim 1, wherein the converted layer is passive to the second process gas.

21. The method of claim 1, wherein a reaction between the converted layer and the second process gas does not produce byproducts.

22. The method of claim 1, further comprising:
    repeating the modifying and the removing to remove an amount the first material before the converting.

23. The method of claim 1, wherein:
    the first material comprises an aluminum oxide,
    the second material comprises a zinc oxide,
    the first process gas comprises a hydrogen fluoride,
    the second process gas comprises trimethylaluminum,
    the third process gas comprises zirconium tetrachloride, and
    the converted layer comprises a zirconium oxide.

24. The method of claim 1, further comprising:
    removing the converted layer by flowing a fourth process gas onto the substrate, wherein the fourth process gas comprises dimethylaluminum chloride.

25. The method of claim 1, wherein the converting comprises a cation exchange between an element in the third process gas and the second material.

26. The method of claim 1, wherein the modifying and the removing occur while the substrate is maintained at the same, or substantially the same, temperature.

27. The method of claim 1, wherein:
    the modifying occurs while the substrate is maintained at a first temperature, and the removing occurs while the substrate is maintained at a second temperature different than the first temperature.

28. The method of claim 1, wherein during the converting, water vapor is not provided to the substrate.

29. A method, comprising:
providing a substrate to a processing chamber, the substrate having a first material adjacent to and covering a surface of a second material;
modifying a layer of the first material by flowing a first process gas onto the substrate and thereby creating a modified layer of the first material;
removing the modified layer of the first material by flowing a second process gas onto the substrate; and
selectively converting, when the surface of the second material is uncovered via removal of the modified layer, the surface of the second material to a layer of etch stop material, wherein the layer of etch stop material is only positioned on top of the second material, such that during the removing, the modified layer of the first material and the layer of etch stop material are exposed to the second process gas and the second process gas is less reactive with the layer of etch stop material than with the modified layer of the first material and the second material.

30. An apparatus for semiconductor processing, the apparatus comprising:
a processing chamber that includes an interior and a substrate support configured to support a substrate in the interior;
a process gas unit configured to flow a first process gas comprising a modifying molecule onto the substrate in the processing chamber, a second process gas comprising a removal molecule onto the substrate in the processing chamber, and a third process gas comprising a conversion molecule onto the substrate in the processing chamber; and
a controller with instructions that are configured to:
cause the first process gas to flow onto the substrate and thereby create a modified layer of a first material on the substrate, wherein the substrate has the first material adjacent to and covering a surface of a second material,
cause the second process gas to flow onto the substrate and thereby remove the modified layer of the first material, and
cause the third process gas to flow onto the substrate to convert, when the surface of the second material is uncovered, the surface to a converted layer of the second material, wherein the first and second process gases are less reactive with the converted layer than with the first material and the second material.

* * * * *